US012421489B2

(12) United States Patent
Elmer et al.

(10) Patent No.: US 12,421,489 B2
(45) Date of Patent: Sep. 23, 2025

(54) BIOLOGICAL CONTROL OF PLANT PATHOGENIC MICROORGANISMS

(71) Applicant: The New Zealand Institute for Plant and Food Research Limited, Auckland (NZ)

(72) Inventors: Philip Elmer, Hamilton (NZ); Stephen Hoyte, Hamilton (NZ)

(73) Assignee: The New Zealand Institute for Plant and Food Research Limited, Auckland (NZ)

(*) Notice: Subject to any disclaimer, the term of this patent is extended or adjusted under 35 U.S.C. 154(b) by 782 days.

(21) Appl. No.: 17/408,169

(22) Filed: Aug. 20, 2021

(65) Prior Publication Data

US 2021/0380931 A1  Dec. 9, 2021

Related U.S. Application Data

(62) Division of application No. 16/331,938, filed as application No. PCT/IB2017/055453 on Sep. 11, 2017, now abandoned.

(60) Provisional application No. 62/393,641, filed on Sep. 12, 2016.

(30) Foreign Application Priority Data

Sep. 13, 2016 (NZ) .................................... 724271
Oct. 28, 2016 (NZ) .................................... 725641

(51) Int. Cl.
C12N 1/14 (2006.01)
A01N 63/32 (2020.01)
C12R 1/645 (2006.01)

(52) U.S. Cl.
CPC ............. C12N 1/145 (2021.05); A01N 63/32 (2020.01); C12R 2001/645 (2021.05)

(58) Field of Classification Search
CPC .......... C12N 1/145; C12N 1/14; A01N 63/32; C12R 2001/645
See application file for complete search history.

(56) References Cited

U.S. PATENT DOCUMENTS

| | | |
|---|---|---|
| PP6,815 P | 5/1989 | Wilkins et al. |
| 5,711,946 A | 1/1998 | Chand-goyal et al. |
| 5,741,699 A | 4/1998 | Wilson et al. |
| PP11,066 P | 9/1999 | Lowe et al. |
| 6,419,922 B1 | 7/2002 | El Ghaouth et al. |
| 6,500,425 B1 | 12/2002 | Mclaughlin et al. |
| 6,562,337 B2 | 5/2003 | Schisler et al. |
| 6,896,883 B2 | 5/2005 | Bergstrom et al. |
| 6,991,930 B1 | 1/2006 | Janisiewicz et al. |
| 6,994,849 B2 | 2/2006 | Droby |
| 7,053,025 B2 | 5/2006 | Sahasrabudhe |
| 7,579,183 B1 | 8/2009 | Hua |
| 7,601,346 B1 | 10/2009 | Schisler et al. |
| 7,906,131 B2 | 3/2011 | Brower |
| 7,935,360 B2 | 5/2011 | Paul |
| 8,460,649 B2 | 6/2013 | Pujos et al. |
| 8,529,964 B1 | 9/2013 | Mann et al. |
| 2007/0141031 A1 | 6/2007 | Kunz |
| 2009/0010905 A1 | 1/2009 | Pujos |
| 2011/0257009 A1 | 10/2011 | Seitz et al. |
| 2012/0015806 A1 | 1/2012 | Paikray et al. |
| 2013/0017949 A1 | 1/2013 | Jabs et al. |

FOREIGN PATENT DOCUMENTS

| | | |
|---|---|---|
| AU | 2002302128 B2 | 11/2004 |
| AU | 2002255715 B2 | 5/2008 |
| BR | PI0804594 A2 | 7/2010 |
| BR | PI0605945 A2 | 7/2012 |
| CN | 1313006 C | 5/2007 |
| CN | 101235293 A | 8/2008 |
| CN | 101270340 A | 9/2008 |
| CN | 101455210 A | 6/2009 |
| CN | 101462897 A | 6/2009 |
| CN | 101412972 B | 9/2010 |
| CN | 101946805 A | 1/2011 |
| CN | 101993829 A | 3/2011 |
| CN | 101173260 B | 4/2011 |
| CN | 102010825 A | 4/2011 |
| CN | 102388955 A | 3/2012 |
| CN | 102432350 A | 5/2012 |
| CN | 101914447 B | 7/2012 |
| CN | 101724558 B | 8/2012 |
| CN | 101899400 B | 8/2012 |
| CN | 102630424 A | 8/2012 |
| CN | 102174398 B | 10/2012 |
| CN | 102224843 B | 11/2012 |
| CN | 102827773 A | 12/2012 |
| EP | 0688169 A1 | 12/1995 |
| EP | 0961548 B1 | 9/2001 |
| EP | 1815742 A1 | 8/2007 |

(Continued)

OTHER PUBLICATIONS

EPA. Blossom Protect. EPA. 2015;1-14.*
Leggett et al. Formulation of microbial biocontrol agents—an industrial perspective. Can. J. Plant Pathol. 2011;33(2):101-107.*
Scortichini et al. *Pseudomonas syringae* pv. actinidiae: a re-emerging, multi-faceted, pandemic pathogen. Molecular Plant Pathology. 2012;13(7):631-640.*
Office Action mailed Jun. 29, 2022 and Response dated Aug. 29, 2022 in corresponding Korean Patent Application KR 2019-7010364.

(Continued)

*Primary Examiner* — Lynn Y Fan
(74) *Attorney, Agent, or Firm* — LEYDIG, VOIT & MAYER, LTD.

(57) ABSTRACT

The present invention relates to the use of an isolated *Aureobasidium pullulans* yeast strain YBCA5 as a biological control agent. Processes and compositions for the biological control of phytopathogenic bacteria and fungi using YBCA5 are also provided.

21 Claims, 15 Drawing Sheets

(56) References Cited

FOREIGN PATENT DOCUMENTS

| | | |
|---|---|---|
| EP | 1802196 B1 | 9/2010 |
| EP | 2269454 A1 | 1/2011 |
| EP | 2269455 A1 | 1/2011 |
| IN | 200500290 P1 | 12/2008 |
| IN | 200803455 P4 | 3/2009 |
| IN | 20090058011 | 1/2011 |
| IN | 201105827 P1 | 12/2012 |
| JP | S63190808 A | 8/1988 |
| JP | 2091010 A | 3/1990 |
| JP | H10248386 A | 9/1998 |
| JP | 2002176969 A | 6/2002 |
| JP | 2002345344 A | 12/2002 |
| JP | 2003192515 A | 7/2003 |
| JP | 2005343772 A | 12/2005 |
| JP | 2006542418 A | 8/2008 |
| JP | 2010215593 A | 9/2010 |
| JP | 04931388 B2 | 5/2012 |
| KR | 20010016397 A | 3/2001 |
| KR | 891843 B1 | 4/2009 |
| KR | 2013055959 A | 5/2013 |
| MX | 223595 B | 10/2004 |
| NZ | 244204 A | 3/1994 |
| NZ | 594123 A | 12/2012 |
| TW | 200621159 A | 7/2006 |
| WO | WO 1998/051155 A1 | 11/1998 |
| WO | WO 2008/114304 A2 | 9/2008 |

OTHER PUBLICATIONS

Andrews et al. (1983) "Microbial antagonism to the imperfect stage of the apple scab pathogen, *Venturia inaequalis*," Phytopathology 73(2): 228-234.

Andrews (1992) "Biological control in the phyllosphere," Annu Rev Phytopathol 30: 603-635.

ATCC. The sodium bicarbonate-carbon dioxide system How does the sodium bicarbonate-carbon dioxide system buffer the pH of cell culture medium?. ATCC. 2014;1-2.

Bajaj et al. (2013) "Killer toxin from a novel killer yeast *Pichia kudriavzevii* RY55 with idiosyncratic antibacterial activity," Journal of Basic Microbiology 53(8): 645-656.

Bajaj et al. (May 2017) "Biology of Killer Yeast and Technological Implications," In; Yeast Diversity in Human Welfare, Springer: 163-190.

Bencheqroun et al. (2007) "In vitro and in situ study of postharvest apple blue mold biocontrol by *Aureobasidium pullulans*: Evidence for the involvement of competition for nutrients," Postharvest Biology and Technology 46(2): 128-135.

Chi et al. (2009) "Bioproducts from *Aureobasidium pullulans*, a biotechnologically important yeast," Appl Microbiol Biotechnol 82(5): 793-804.

Chilean Office Action, dated Jun. 22, 2020, corresponding to Chilean Patent Application No. 201900584, 17 pp.

Collina et al. (Dec. 2016) "Greenhouse assays on the control of the bacterial canker of kiwifruit (*Pseudomonas syringae* pv. actinidiae)," Journal of Berry Research 6(4): 407-415.

Da Rocha et al. (2005) "History and perspectives on the use of disease resistance inducers in horticultural crops," HortTechnology 15(3): 518-529.

De Melo et al. (Feb. 2015) "Efficacy of Yeast in the Biocontrol of Bacterial Fruit Blotch in Melon Plants," Tropical Plant Pathology 40(1): 56-64.

Di Francesco et al. (publicly available Nov. 2014) "Production of volatile organic compounds by *Aureobasidium pullulans* as a potential mechanism of action against postharvest fruit pathogens," Biological Control (Feb. 2015) 81: 8-14.

Di Francesco et al. (publicly available Sep. 10, 2015) "Activities of *Aureobasidium pullulans* cell filtrates against *Monilinia laxa* of peaches," Microbiological Research (Dec. 2015) 181: 61-67.

Di Francesco et al. (publicly available Feb. 17, 2017) "Biocontrol of *Monilinia laxa* by *Aureobasidium pullulans* strains: Insights on competition for nutrients and space," International Journal of Food Microbiology (May 2017) 248: 32-38.

Eshel et al. (2002) "pH regulates endoglucanase expression and virulence of *Alternaria alternata* in persimmon fruit," Molecular Plant-Microbe Interactions 15(8): 774-779.

Extended European Search Report, dated Apr. 14, 2020, corresponding to European Patent Application No. 17848253.5, 9 pp.

Ferraz et al. (publicly available Apr. 2016) "Biocontrol ability and putative mode of action of yeasts against *Geotrichum citri-aurantii* in citrus fruit," Microbiological Research (Jul.-Aug. 2016)(188): 72-79.

Fisher (2013) "New Psa products promising," SunLive, availbable online at http://www.sunlive.co.nz/news/38949-new-psa-products-promising.html, 3 pp.

Fonseca et al. (2006) "Phylloplane Yeasts," Chapter 13 In; Biodiversity and Ecophysiology of Yeasts. G. Péter and C. Rosa. Berlin, Heidelberg, Springer Berlin Heidelberg: 263-301.

Holb et al. (2013) "Integrated control of brown rot blossom blight by combining approved chemical control options with *Aureobasidium pullulans* in organic cherry production," Crop Protection 54:114-120.

International Preliminary Report on Patentability, date Mar. 21, 2019, corresponding to International Patent Application No. PCT/IB2017/055453, 8 pp.

International Search Report and Written Opinion, dated Dec. 5, 2017, corresponding to International Patent Application No. PCT/IB2017/055453, 9 pp.

Ippolito et al. (2000) "Control of postharvest decay of apple fruit by *Aureobasidium pullulans* and induction of defense responses," Postharvest Biology and Technology 19(3): 265-272.

Kiwifruit Vine Health "Your Suggestions and Ideas," available online at http://www.kvh.org.n z/your_ideas, 6 pp. [Accessed Jan. 14, 2014].

Kiwifruit Vine Health (2017/2018) "Annual Update 2017/18," available online at https://www.kvh.o rg.nz/vdb/document/104324, 20 pp.

Klein et al. (publicly available Jul. 2017) "Biofilm production by *Aureobasidium pullulans* improves biocontrol against sour rot in citrus," Food Microbiology (Feb. 2018) 69: 1-10.

Köhl et al. (2011) "Stepwise screening of microorganisms for commercial use in biological control of plant-pathogenic fungi and bacteria," Biological Control 57(1): 1-12.

Köhl et al. (Jul. 2019) "Mode of action of microbial biological control agents against plant diseases: relevance beyond efficacy," Frontiers in plant science 10: 845, pp. 1-19.

Lee et al. (Jan. 2017) "Foliar application of the leaf-colonizing yeast *Pseudozyma churashimaensis* elicits systemic defense of pepper against bacterial and viral pathogens," Scientific Reports 7: 39432, pp. 1-13.

Lima et al., (1997) "Effectiveness of Aureobasidium pullulans and Candida oleophila against postharvest strawberry rots," Postharvest Biology and Technology 10:169-178.

Loncaric et al., (2009) "*Phenotypic and genotypic diversity among strains of Aureobasidium pullulans in comparison with related species*," Antonie van Leeuwenhook, 95:165-178.

Madhupani et al. (Mar. 2017) "Delayed incidence of stem-end rot and enhanced defences in *Aureobasidium pullulans*-treated avocado (*Persea americana* Mill.) fruit," Journal of Plant Diseases and Protection 124: 227-234.

McCormack et al. (1994) "Production of antibacterial compounds by phylloplane-inhabiting yeasts and yeastlike fungi," Applied and Environmental Microbiology 60(3): 927-931.

McCormack et al. (1995) "The influence of moisture on the suppression of *Pseudomonas syringae* by *Aureobasidium pullulans* on an artificial leaf surface," FEMS Microbiology Ecology 16(2): 159-165.

McGillivray (2013) "New hope for kiwifruit against Psa," NZ Herald, 3 pp.

McGrath et al. (2006) "Temporal changes in microscale colonization of the phylloplane by *Aureobasidium pullulans*," Appl Environ Microbiol 72(9): 6234-6241.

(56) References Cited

OTHER PUBLICATIONS

Mounir et al., (2007) "Production, formulation and antagonistic activity of the biocontrol like-yeast Aureobasidium pullulans against Penicillium expansum," Biotechnol. Lett. 29: 553-559.
Parafati et al. (Sep. 2016) "The effect of locust bean gum (LBG)-based edible coatings carrying biocontrol yeasts against Penicillium digitatum and Penicillium italicum causal agents of postharvest decay of mandarin fruit," Food Microbiology 58: 87-94.
Pinto et al. (Dec. 2018) "Understand the potential role of Aureobasidium pullulans, a resident microorganism from grapevine, to prevent the infection caused by Diplodia seriata," Frontiers in microbiology 9: 3047, pp. 1-15.
Prusky et al. (2003) "Pathogenic fungi: leading or led by ambient pH?" Molecular Plant Pathology 4(6): 509-516.
Ravella et al. (2010) "Extracellular polysaccharide (EPS) production by a novel strain of yeast-like fungus Aureobasidium pullulans," Carbohydrate Polymers 82(3): 728-732.
Reglinski et al. (2009) "Induced Resistance for Plant Disease Control," Chapter 4 In; Disease Control in Crops: Biological and Environmentally Friendly Approaches, Wiley-Blackwell, United Kingdom: 62-92.
Rühmann et al. (2013) "Induction of stilbene phytoalexins in grapevine (Vitis vinifera) and transgenic stilbene synthase-apple plants (Malus domestica) by a culture filtrate of Aureobasidium pullulans," Plant Physiol Biochem 72: 62-71.
Singh et al. (2015) "Aureobasidium pullulans—An Industrially Important Pullulan Producing Black Yeast," Int. J. Curr. Microbiol. App. Sci 4(10): 605-622.
Singh et al. (2017) "Production of Pullulan from a high yielding strain of Aureobasidium pullulans in non-stirred flask-type fermentation system," Journal of Microbiology and Biotechnology Research 7(1): 26-32.
Spadaro et al. (publicly available Nov. 2015) "Development of biocontrol products for postharvest diseases of fruit: The importance of elucidating the mechanisms of action of yeast antagonists," Trends in Food Science & Technology (Jan. 2016) 47: 39-49.
Sperandio et al. (Nov. 2015) "Yeasts from native Brazilian Cerrado plants: Occurrence, diversity and use in the biocontrol of citrus green mould," Fungal Biology 119(11): 984-993 (Abstract only).
Sprague et al. (2006) "Eukaryotes learn how to count: quorum sensing by yeast," Genes & Development 20(9): 1045-1049.
Stewart et al. (2011) "Desktop evaluation on commercially available microbial-based products for control or suppression of Pseudomonas syringae pv. Actinidiae," Bio-Protection Research Centre, 33 pp.
Stirling et al. (1995) "Isolation and selection of bacteria and yeasts antagonistic to preharvest infection of avocado by Colletotrichum gloeosporioides," Australian Journal of Agricultural Research 46(5):985-995 (Abstract only).
Sylla et al. (Jul. 2015) "Control of Botrytis cinerea in strawberries by biological control agents applied as single or combined treatments," European Journal of Plant Pathology 143(3): 461-471.
Tang et al. (publicly available May 2015) "Combining an antagonistic yeast with harpin treatment to control postharvest decay of kiwifruit," Biological Control (Oct. 2015) 89: 61-67.

Trevelyan's Kiwifruit News (Aug. 2016) "Zespri, KVH Psa R&D Presentation, The Orchard," available online at https://web.archive.org/web/20170408112638/https://trevelyan.co.nz/files/4814/7258/9002/AugustTrevelyanNewsletter.pdf, pp. 6-7 (8 pp. total).
United States Environmental Protection Agency (Jan. 2015) "Fast-Track Label Amendments to add Spanish text and Update Directions for Use for Enhanced Clarity," available online at https://www3.epa.gov/pesticides/chem_search/ppls/086174-00003-20150129.pdf, 13 pp.
Wachowska et al. (Oct. 2016) "Biofilm of Aureobasidium pullulans var. pullulans on Winter Wheat Kernels and its Effect on Other Microorganisms," Microbiology 85(5): 523-530.
Ward FM. Natural Products Insider. Stabilizers, naturally. 2007;1-10.
Wicaksono et al. (publicly available Mar. 2017) "Biological control of Pseudomonas syringae pv. actinidiae (Psa), the causal agent of bacterial canker of kiwifruit, using endophytic bacteria recovered from a medicinal plant," Biological Control (Jan. 2018) 116: 103-112.
Wurms et al. (2011) "Developing new biologically-based products for control of botrytis bunch rot," Part 1 and Part 2, Wine and Viticulture Journal (Sep./Oct. 2011): 64-78.
Zhang et al. (2010) "Efficacy of the antagonist Aureobasidium pullulans PL5 against postharvest pathogens of peach, apple and plum and its modes of action," Biological Control 54(3): 172-180.
Zhang et al. (2012) "Cloning, characterization, expression and antifungal activity of an alkaline serine protease of Aureobasidium pullulans PL5 involved in the biological control of postharvest pathogens," International Journal of Food Microbiology 153(3): 453-464.
Lima et al. (1997) "Effectiveness of Aureobasidium pullulans and Candida oleophila against postharvest strawberry rots," Postharvest Biology and Technology, vol. 10, Issue 2, 169-178.
Lima et al. (2005) "Integration of Biocontrol Agents and Food-Grade Additives for Enhancing Protection of Stored Apples from Penicillium expansum," Journal of Food Protection 68(10), 2100-2106.
Japanese Official Action, corresponding to Japanese Patent Appln. No. 2019-513906, dated May 28, 2021, 8 pages.
Dake et al. (2014), "Antibacterial activity of Aureobasidium pullulans," Int J Pharm Bio Sci, 5(3): 1026-1048.
Gong et al. (2016), "Control of postharvest gray mold of apple by Aureobasidium pullulans," Chinese Journal of Biological Control, 32(2): 251-257.
Janisiewicz & Korsten (2002), "Biological control of postharvest diseases of fruits," Annu. Rev. Phytopathology 40: 411-441.
Schena et al. (2002), "Molecular detection of strain L47 of Aureobasidium pullulans, a biocontrol agent of postharvest diseases", Plant Dis. 86(1): 54-60.
Cornish et al. (2025), "The biological control agent for bacterial canker of kiwifruit, in Aureo® Gold, is a strain of Aureobasidium pullulans identifiable by novel SCAR marker primers," Biological Control 202: 105709.

* cited by examiner

BIOLOGICAL CONTROL OF PLANT PATHOGENIC MICROORGANISMS

CROSS-REFERENCE TO RELATED APPLICATIONS

This application is a divisional of U.S. Nonprovisional application Ser. No. 16/331,938, filed Mar. 8, 2019, which is a U.S. National Stage Application filed under 35 U.S.C. § 371 of International Application No. PCT/IB2017/055453, filed Sep. 11, 2017, which claims the benefit of U.S. Provisional Application Nol. 62/393,641, filed Sep. 12, 2016; New Zealand Application No. 724271, filed Sep. 13, 2016; and New Zealand Application No. 725641, filed Oct. 28, 2016. All of these applications are hereby incorporated by reference in their entireties.

FIELD OF THE INVENTION

This invention relates generally to methods of using yeasts for the biological control of plant pathogenic bacteria and fungi. In particular, the invention relates to a novel yeast strain having biological control activity, and to methods of using this strain to inhibit the survival, growth and/or proliferation of plant pathogenic bacteria and fungi on fruit or vegetable plants.

BACKGROUND OF THE INVENTION

Plant disease represents a significant economic cost to modern agriculture. Current systems of agriculture often require one or a few crops or plant types to be grown over a large area. Such an ecologically unbalanced system is susceptible to disease.

Traditionally, control of disease causing plant pathogens such as bacteria and fungi has been carried out using chemical pesticides. However, the use of chemicals is subject to a number of disadvantages. Pathogens can and have developed tolerance to chemicals over time, producing increasingly pesticide resistant populations. Chemical residues may also pose environmental hazards as well as raising health concerns. In particular, consumers have become increasingly concerned about chemical residues on plants and in food and wine, and their effects on human health and the environment.

Biological control represents an alternative means of controlling plant disease which reduces dependence on chemicals. Such "natural" methods enjoy greater public acceptance, and may be more effective and sustainable than chemical control methods.

*Pseudomonas* is a genus of Gram-negative, aerobic gammaproteobacteria, belonging to the family Pseudomonadaceae. The genus contains 191 validly described species, of which a number are plant pathogens. Within the genus *Pseudomonas* spp., *P. syringae* is a prolific plant pathogen that exists as over 50 different pathovars (pv.), many of which demonstrate a high degree of host-plant specificity. Numerous other *Pseudomonas* species can also act as plant pathogens, most notably all of the other members of the *P. syringae* subgroup. For example, commercially important diseases caused by *P. syringae* pathovars include bacterial blast of stone fruits, bacterial speck of tomato, and blight in peas.

*Pseudomonas syringae* pv. *actinidiae* (Psa) is a serious bacterial disease affecting kiwifruit. Psa was first recorded in New Zealand in early November 2010, and as of 18 Jul. 2013, 75% of hectares of kiwifruit were on orchards with some Psa infection. The immediate cost of Psa to the New Zealand kiwifruit industry is estimated to be between $310 million and $410m from 2013 to 2018, and more than double that in the long-term for lost development.

As with many bacterial plant diseases, control options are limited. The main solutions currently in use are crop hygiene, chemical based treatment such as copper-based products, and/or plant defence elicitors such as acibenzolar-S-methyl (Actigard/Bion, Syngenta) and antibiotics such as streptomycin sulphate and kasugamycin. However, severe restrictions have been placed on the use of these products and time of the growing season that they can be used (e.g. in New Zealand). In addition, the use of some of these products are prohibited in some key export regions e.g., Streptomycin is not permitted for use on horticulture in Europe.

It has been estimated that in the 2012 season in New Zealand, $13 Million was spent on sprays to protect kiwifruit against Psa. This is the chemical cost alone. Other management costs have not been factored into this estimate. Outside of New Zealand, Psa is also a critical issue in Europe (Italy/France), South America and potentially in China and South Korea.

*Botrytis cinerea* and recently identified *B. pseudocinerea* are phytopathogenic fungi (telemorph *Botryotinia fuckeliana*) and are the causal agents of the grey mold (*Botrytis* blight) disease. Some estimates of global crop losses resulting from *Botrytis* spp. are on the order of 10-100 billion Euros per year (http://www<dot>genoscope<dot>cns<dot>fr). *Botrytis* spp. is also the causative agent of bunch rot of grapes, and is estimated to cause losses of $18 million dollars per annum to the New Zealand wine industry alone. *Botrytis* spp. control has been by way of fungicides. As with the use of chemical treatments to control pathogenic bacteria, this practice is unsustainable because fungicide resistance is widespread in many vineyards and there is consumer pressure for reduction in pesticide residue.

Brown rot on fruit is caused by *Monilinia* spp. fungi. *Monilinia* spp. are pathogens of many economically important crops in the Family Rosaceae including cherries, plums, peaches, apricots, strawberries, raspberries, apples and pears. *Monilinia* spp. are also pathogens of many flowering plants within the Family Ericaceae. Damage caused by *Monilinia* spp. can often cause major losses to crops and valuable ornamental flowers. The genus *Monilinia* contains about thirty described species.

Importantly, the revenues lost due to the impact of phytopathogenic fungi represent a mere fraction of the total economic impact of these pathogens worldwide. As with *Botrytis*, control of *Monilinia* spp. and *Sclerotinia* spp. on economically important crops has traditionally been by way of fungicides. Some estimates consider that the cost of chemical control of *Botrytis* spp. alone can reach $780 million for just one crop with disease on treated plants still resulting in significant production loss (Genescope, 2002); (Laluk, Kristin and Tesfaye Mengiste; 2010 in *Arabidopsis* Book 2010, Vol. 8).

Accordingly, for a number of economic, health and environmental sustainability reasons as discussed above, the use of chemical based treatments, plant defence elicitors and antibiotics has limitations. Therefore, there is a need for new biological control solutions, which do not have similar cost, health or environmental issues to chemical based treatments in order to provide sustainable management of these diseases.

It is an object of the invention to provide at least one yeast biological control agent and/or a composition comprising at least one yeast biological control agent and/or methods of using such an agent and/or such a composition for controlling *Pseudomonas* spp. bacteria on at least one plant or part thereof, preferably *Pseudomonas syringae* pv. *actinidiae* (Psa); and/or to at least to provide the public with a useful choice.

SUMMARY OF THE INVENTION

In one aspect the invention relates to isolated *Aureobasidium pullulans* yeast strain YBCA5 (CBS Accession #141880).

In another aspect the invention relates to a composition comprising isolated *Aureobasidium pullulans* yeast strain YBCA5 (CBS Accession #141880) and an agriculturally acceptable carrier.

In another aspect the invention relates to a composition consisting essentially of isolated *Aureobasidium pullulans* yeast strain YBCA5 (CBS Accession #141880) and an agriculturally acceptable carrier.

In another aspect the invention relates to a method of controlling *Pseudomonas* spp. bacteria on a plant or part thereof, the method comprising contacting the plant or part thereof with YBCA5, or a composition comprising YBCA5.

In another aspect the invention relates to the use of YBCA5, or a composition comprising YBCA5 for controlling *Pseudomonas* spp. bacteria on a plant or part thereof.

In another aspect the invention relates to YBCA5, or a composition comprising YBCA5 for use in, or when used, for controlling *Pseudomonas* spp. bacteria on a plant or part thereof.

In another aspect the invention relates to a method for controlling *P. syringae* pv. *actinidiae* (Psa) on a kiwifruit plant or part thereof, the method comprising contacting the kiwifruit plant or part thereof with YBCA5, or a composition comprising YBCA5.

In another aspect the invention relates to a method for increasing the yield of a kiwifruit plant infected, or susceptible to infection with Psa, the method comprising applying YBCA5 or a composition comprising YBCA5 to the kiwifruit plant or part thereof, and growing the kiwifruit plant or part thereof.

In another aspect the invention relates to the use of YBCA5, or a composition comprising YBCA5 for controlling Psa on a kiwifruit plant or part thereof.

In another aspect the invention relates to the use of YBCA5, or a composition comprising YBCA5 for increasing the yield of a kiwifruit plant infected, or susceptible to infection with Psa.

In another aspect the invention relates to YBCA5, or a composition comprising YBCA5 for use in, or when used, for controlling Psa on a kiwifruit plant or part thereof.

In another aspect the invention relates to YBCA5, or a composition comprising YBCA5 for use in, or when used, for increasing the yield of a kiwifruit plant infected, or susceptible to infection with Psa.

In another aspect the invention relates to a method of controlling at least one phytopathogenic fungus on a plant or part thereof, the method comprising contacting the plant or part thereof with YBCA5, or a composition comprising YBCA5.

In another aspect the invention relates to a method for increasing the yield of a fruit or vegetable plant infected with, or susceptible to infection by a phytopathogenic fungus, the method comprising applying YBCA5 or a composition comprising YBCA5 to the fruit or vegetable plant or part thereof YBCA5, and growing the plant or part thereof.

In another aspect the invention relates to the use of YBCA5, or a composition comprising YBCA5 for controlling a phytopathogenic fungus on a fruit or vegetable plant or part thereof.

In another aspect the invention relates to the use of YBCA5, or a composition comprising YBCA5 for increasing the yield of a fruit or vegetable plant or part thereof infected with, or susceptible to infection by a phytopathogenic fungus.

In another aspect the invention relates to YBCA5, or a composition comprising YBCA5 for use in, or when used, for controlling at least one phytopathogenic fungus on a plant or part thereof.

In another aspect the invention relates to YBCA5, or a composition comprising YBCA5 for use in, or when used, for controlling at least one phytopathogenic fungus on a fruit or vegetable plant or part thereof.

In another aspect the invention relates to YBCA5, or a composition comprising YBCA5 for use in, or when used, for increasing the yield of a fruit or vegetable plant susceptible to infection by at least one phytopathogenic fungus.

In another aspect the invention relates to at least one plant or part thereof treated with YBCA5, or a composition comprising YBCA5.

In another aspect the invention relates to at least one fruit or vegetable plant or part thereof treated with YBCA5, or a composition comprising YBCA5.

In another aspect the invention relates to at least one plant or part thereof treated with YBCA5, or a composition comprising YBCA5. In some embodiments the plant is a fruit or vegetable plant or part thereof. In one embodiment the plant is a kiwifruit vine, a cherry tree or a grape vine.

While various embodiments of certain aspects of the invention are set out above, the invention is not limited thereto. Additional embodiments of the aspects of the invention set out above are further described in the Detailed Description and set out in the claims of the application.

Other aspects and embodiments of the invention may become apparent from the following description which is given by way of example only and with reference to the accompanying drawings.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

BRIEF DESCRIPTION OF THE DRAWINGS

The invention will now be described by way of example only and with reference to the drawings in which.

DETAILED DESCRIPTION OF THE INVENTION

Definitions

Figure 1:
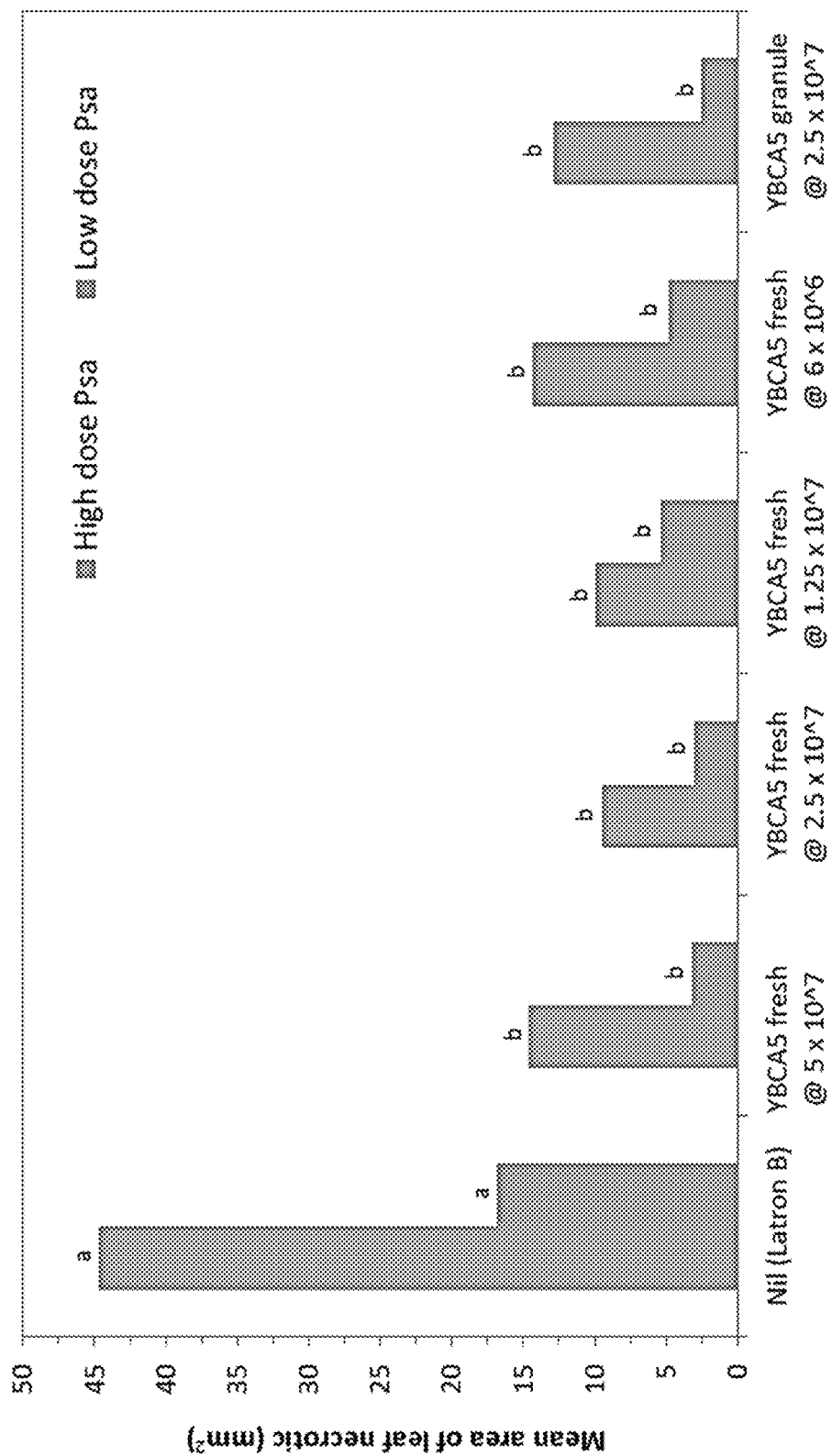
FIG. 1. Psa severity (mean area of leaf necrosis) on potted 'Hayward' seedlings treated with different concentrations of freshly fermented YBCA5, compared with a water soluble granule formulation (YBCA5 granule) and inoculated with two doses ($5\times10^6$ per droplet and $2\times10^5$ per 10 ul droplet) of Psa. Three 10 ul droplets of each dose of Psa were used per side of the leaf. Treatments were applied eight and one day (1 d) prior to inoculation with Psa on 18 Sep. 2014 and assessed after 28 days.

The following definitions are presented to better define the present invention and as a guide for those of ordinary skill in the art in the practice of the present invention.

Unless otherwise specified, all technical and scientific terms used herein are to be understood as having the same meanings as is understood by one of ordinary skill in the relevant art to which this disclosure pertains.

Examples of definitions of common terms in botany, microbiology, molecular biology and biochemistry can be found in Biology of Plants, Raven et al. (eds.), W.H. Freeman and Company, (2005); Plant Physiology, Taiz et al. (eds.), Sinauer Associates, Incorporated, (2010); Botany: An Introduction to Plant Biology, J. D. Mauseth, Jones & Bartlett Learning, (2003); Methods for General and Molecular Microbiology, 3rd Edition, C. A. Reddy, et al. (eds.), ASM Press, (2008); Encyclopedia of Microbiology, 2nd ed., Joshua Lederburg, (ed.), Academic Press, (2000); Microbiology By Cliffs Notes, I. Edward Alcamo, Wiley, (1996); Dictionary of Microbiology and Molecular Biology, Singleton et al. (2d ed.) (1994); Biology of Microorganisms 11$^{th}$ ed., Brock et al., Pearson Prentice Hall, (2006); Biodiversity of Fungi: Inventory and Monitoring Methods, Mueller et al., Academic Press, (2004); Genes IX, Benjamin Lewin, Jones & Bartlett Publishing, (2007); The Encyclopedia of Molecular Biology, Kendrew et al. (eds.), Blackwell Science Ltd., (1994); and Molecular Biology and Biotechnology: a Comprehensive Desk Reference, Robert A. Meyers (ed.), VCH Publishers, Inc., (1995).

It is also believed that practice of the present invention can be performed using standard botanical, microbiological, molecular biology and biochemistry protocols and procedures as known in the art, and as described, for example in Environmental Microbiology: Methods and Protocols, J. F. T. Spencer et al., Humana Press, (2004); Environmental Microbiology, P. D. Sharma, Alpha Science International, (2005); Environmental Microbiology, J. R. Leadbetter, Gulf Professional Publishing, (2005) and other commonly available reference materials relevant in the art to which this disclosure pertains, and which are all incorporated by reference herein in their entireties.

The term "plant" as used herein encompasses whole plants and all parts of a plant from all stages of a plant lifecycle including but not limited to vegetative and reproductive cells and tissues, propagules, seeds, embryos, fruits, shoots, stems, leaves, leaf sheaths and blades, inflorescences, roots, anthers, ligules, palisade, mesophyll, epidermis, auricles, palea, lemma and tillers.

The term "kiwifruit" is used herein as the common name for all commercially grown fruit from the genus *Actinidia*. The most common kiwifruit is the green-fleshed kiwifruit, from the species *Actinidia chinensis* var. *deliciosa*. Other species that are commonly eaten include golden kiwifruit (*A. chinensis* var. *chinensis*), Chinese egg gooseberry (*A. coriacea*), baby kiwifruit (*A. arguta*), Arctic kiwifruit (*A. kolomikta*), red kiwifruit (*A. melanandra; A. chinensis* var. *chinensis*), silver vine (*A. polygama*), and purple kiwifruit (*A. purpurea*).

The term "biological control agent" as used herein refers to agents which act as an antagonist of one or more plant pathogens. Antagonists may take a number of forms. In one form, the biological control agent may out-compete the pathogen for available nutrients and/or space of the host plant. In another form the biological control agent may render the environment unfavourable for the pathogen. Accordingly, the antagonist mechanisms include but are not limited to antibiosis, mycoparasitism, nutrient competition and physical displacement.

The terms "control", "controlling", "biocontrol" or "biological control" are used interchangeably herein to refer to the reduction of the amount of inoculum or disease-producing activity of a pathogen accomplished by or through one or more microorganisms. Generally comprehended is the prevention or reduction of infection by plant pathogenic bacteria or fungi, particularly plant pathogenic *Pseudomonas* spp., *Botrytis* spp., *Alternaria* spp., *Colletotrichum* spp., *Penicillium* spp., *Phomopsis* spp., *Cryptosporiopsis* spp., *Monilinia* spp., and *Sclerotinia* spp., particularly or inhibition of the rate or extent of such infection, including any reduction in the survival, growth and/or proliferation of the bacteria or fungi. Curative treatment is also contemplated.

The term "statistically significant" as used herein refers to the likelihood that a result or relationship is caused by something other than random chance. A result may be found to be statistically significant using statistical hypothesis testing as known and used in the art. Statistical hypothesis testing provides a "P-value" as known in the art, which represents the probability that the measured result is due to random chance alone. It is believed to be generally accepted in the art that levels of significance of 5% (0.05) or lower are considered to be statistically significant.

The term "effective amount" as used herein means an amount effective to protect against, delay, reduce, stabilise, improve or treat plant pathogenic bacterial or fungal infection in and/or on a plant.

The terms "increasing the yield of a fruit or vegetable plant" and "increasing the yield of a kiwifruit plant" as used herein generally comprehends increasing the rate of production of harvestable fruit and/or kiwifruit, the total number of harvestable fruit and/or kiwifruit (including due to absolute increase in fruit and/or kiwifruit numbers or reduction in disease symptoms leading to increased numbers of saleable fruits), and any increase in size of individual fruits and/or kiwifruits produced on a fruit or vegetable plant or kiwifruit plant treated according to the invention. Increase is generally determined as compared to an equivalent plant that is untreated with the strain or the composition of the invention.

An "agriculturally acceptable adjuvant" as used herein refers to a compound or material that is generally comprehended in the art of agriculture as a useful additive in agricultural formulations or carried out with agricultural treatments.

An "additional active agent" as used herein means any compound or material that is capable of contributing to the control (as defined herein) of plant pathogenic *Pseudomonas* spp. bacteria or phytopathogenic fungi *Botrytis* spp., *Alternaria* spp., *Colletotrichum* spp., *Penicillium* spp., *Phomopsis* spp., *Cryptosporiopsis* spp., *Monilinia* spp., and *Sclerotinia* spp. by the yeasts useful in the present invention, or that is capable of potentiating the effects of the yeasts useful in this invention in controlling plant disease caused by plant pathogenic bacteria and fungi A "formulation agent" as used herein refers to any compound or material that facilitates or optimizes the production, handling, storage, transport, application and/or persistence of the composition of, or for use in the invention on plants (as defined herein), but not limited thereto.

An "agriculturally acceptable carrier" is used herein as is generally comprehended in the art. A preferred agriculturally acceptable carrier is water, but not limited thereto.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

The present invention relates generally to a novel *Aureobasidium pullulans* yeast strain YBCA5 and to compositions comprising YBCA5 and an agriculturally acceptable carrier. In some embodiments the compositions also comprise an agriculturally acceptable adjuvant. The novel strain and compositions of the invention are useful for the biocontrol of plant disease caused by plant pathogenic bacteria and phytopathogenic fungi, particularly *Pseudomonas* spp. bacteria and *Botrytis* spp., *Sclerotinia* spp., *Alternaria* spp., *Colletotrichum* spp., *Penicillium* spp., *Phomopsis* spp., *Cryptosporiopsis* spp., and *Monilinia* spp. fungi. The invention also relates to methods of controlling phytopathogenic bacteria and/or fungi selected from the group consisting of *Pseudomonas* spp. bacteria, *Botrytis* spp., *Sclerotinia* spp., *Penicillium* spp., *Colletotrichum* spp., *Alternaria* spp., *Phomopsis* spp., *Cryptosporiopsis* spp., and *Monilinia* spp. fungi on a plant or part thereof by contacting the plant or part thereof with YBCA5.

The applicants are the first to provide the isolated yeast strain YBCA5, and compositions comprising YBCA5 and an agriculturally acceptable carrier that are effective at controlling *Pseudomonas* spp. bacteria and phytopathogenic fungi on plants. In some embodiments YBCA5 or the composition comprising YBCA5 may also be formulated with an agriculturally acceptable adjuvant. The applicants are also the first to provide methods of using the yeast, *A. pullulans* for biological control of *Pseudomonas* spp. bacteria. In particular, the applicants are the first to show that a strain of *A. pullulans* yeast, or a composition comprising a strain of *A. pullulans* yeast is effective at inhibiting the survival, growth and/or proliferation of *Pseudomonas syringae* pv. *actinidiae* (Psa) on fruit or vegetable plants, particularly fruit or vegetable vines, particularly kiwifruit vines.

Without wishing to be bound by theory the applicants believe that the efficacy of the yeast strain and compositions of the invention relates to either the ability of the yeast strain to competitively exclude Psa and/or phytopathogenic fungi, by excretion of an anti-microbial compound or compounds, or by elicitation of plant defence mechanisms, or a combination of the above. Irrespective of the particular mode of action, the inventors have surprisingly found that YBCA5 is efficacious for treating Psa disease on kiwifruit vines, for treating *Botrytis* spp. and *Monilinia* spp. infection on cherries and grapes, and for treating *Alternaria* spp., *Colletotrichum* spp., *Penicillium* spp., *Phomopsis* spp., *Cryptosporiopsis* spp, on apples and kiwifruit.

YBCA5 is a particularly effective biological control agent against *Pseudomonas* spp. bacteria and phytopathogenic fungi. YBCA5 demonstrates the ability to survive formulation and application protocols, rapidly colonise treated plants, and suppress growth of *Pseudomonas* spp. bacteria and of phytopathogenic fungi on treated plants and parts thereof. YBCA5 has been found to be particularly effective at controlling *P. syringae* bacteria, particularly *P. syringae* pv. *actinidiae* (Psa) bacteria, on kiwifruit vines, and at reducing and/or controlling, to varying degrees, post-harvest fruit rot due to *Botrytis* spp., *Sclerotinia* spp., *Penicillium* spp., *Colletotrichum* spp., *Alternaria* spp., *Phomopsis* spp., *Cryptosporiopsis* spp, and *Monilinia* spp.

YBCA5 and Compositions

Accordingly, in one aspect the invention relates to isolated *Aureobasidium pullulans* yeast strain YBCA5 (CBS Accession #141880).

The particular isolated *A. pullulans* strain YBCA5 of the invention was deposited on 26 Sep. 2016 for the purpose of patent procedure under the Budapest Treaty at the Westerdijk Fungal Biodiversity Institute (formerly the Centraalbureau voor Schimmelcultures (CBS)), Uppsalalaan 8, 3584, CT Utrecht, The Netherlands. This isolate has been accorded deposit number CBS Accession #141880. Upon grant of a patent, all restrictions imposed by the depositor on the availability to the public of the deposited biological material will be irrevocably removed.

The isolated *A. pullulans* yeast strain YBCA5 is a unicellular fungi of the Order Dothideales, Family Aureobasidiaceae, and genus *Aureobasidum*. Cells display a wide range of morphological variability. *A. pullulans* cultivated on potato dextrose agar produces smooth, faint pink, yeast-like colonies. Older colonies can be somewhat darker due to the production of chlamydospores. Primary conidia of *A. pullulans* are single celled, hyaline, smooth, ellipsoidal, and variable in shape and size. *A. pullulans* conidiophores are undifferentiated, intercalary or terminal, or arising as short lateral branches. Endoconidia are produced by *A. pullulans* intercalary cells. Hyphae are thin-walled, hyaline and smooth, with transverse septa. Growth occurs at 10-35° C. with optimal growth being 22-25° C.

In another aspect the invention relates to a composition comprising YBCA5 (CBS Accession #141880) and an agriculturally acceptable carrier.

In another aspect the invention relates to a composition consisting essentially of YBCA5 (CBS Accession #141880) and an agriculturally acceptable carrier.

In one embodiment the agriculturally acceptable carrier is water.

Again, without wishing to be bound by theory, the inventors believe that the when used as a biological control agent, YBCA5 must be in a reproductively viable form. For most purposes YBCA5 desirably incorporated into a composition in the form of reproductively viable cells. Preferably YBCA5 is incorporated into the composition as dried cells.

The concentration of cells in a composition of the invention will depend on the utility to which the composition is put. Optimizing the concentration of cells for a particular application is believed to be within the skill in the art.

In some embodiments the concentration of YBCA5 viable cells in a composition of the invention ranges from about $1 \times 10^3$ to about $1 \times 10^{14}$, preferably about $1 \times 10^5$ to about $1 \times 10^{11}$, preferably about $1 \times 10^6$ to about $1 \times 10^9$, preferably about $1 \times 10^7$ to about $1 \times 10^8$, preferably about $2 \times 10^7$ to about $2 \times 10^8$ CFU, preferably about $2 \times 10^9$ to about $2 \times 10^{10}$ CFU per gram for solid compositions, and about $1 \times 10^7$ to about $1 \times 10^8$ CFU per millilitre for liquid compositions.

In some embodiments the concentration of YBCA5 viable cells in a composition of the invention ranges from $1 \times 10^3$ to about $1 \times 10^{14}$, preferably $1 \times 10^5$ to about $1 \times 10^{11}$, preferably from $1 \times 10^6$ to about $1 \times 10^9$, preferably $1 \times 10^7$ to about $1 \times 10^8$, preferably from $2 \times 10^7$ to about $2 \times 10^8$ CFU, preferably from $2 \times 10^9$ to about $2 \times 10^{10}$ CFU per gram for solid compositions, and from $1 \times 10^7$ to about $1 \times 10^8$ CFU per millilitre for liquid compositions.

In some embodiments the concentration of YBCA5 viable cells in a composition of the invention ranges from about $1 \times 10^3$ to $1 \times 10^{14}$, preferably about $1 \times 10^5$ to $1 \times 10^{11}$, preferably about $1 \times 10^6$ to $1 \times 10^9$, preferably about $1 \times 10^7$ to $1 \times 10^8$, preferably about $2 \times 10^7$ to $2 \times 10^8$ CFU, preferably about $2 \times 10^9$ to $2 \times 10^{10}$ CFU per gram for solid compositions, and about $1 \times 10^7$ to $1 \times 10^8$ CFU per millilitre for liquid compositions.

In some embodiments the concentration of YBCA5 viable cells in a composition of the invention ranges from $1 \times 10^3$ to $1 \times 10^{14}$, preferably $1 \times 10^5$ to $1 \times 10^{11}$, preferably $1 \times 10^6$ to $1 \times 10^9$, preferably $1 \times 10^7$ to $1 \times 10^8$, preferably $2 \times 10^7$ to $2 \times 10^8$ CFU, preferably $2 \times 10^9$ to $2 \times 10^{10}$ CFU per gram for solid compositions, and $1 \times 10^7$ to $1 \times 10^8$ CFU per millilitre for liquid compositions.

In some embodiments the concentration of YBCA5 viable cells in a composition of the invention is about $2 \times 10^{10}$ CFU per gram for solid compositions, and about $2 \times 10^7$ CFU per millilitre for liquid compositions.

In some embodiments the concentration of YBCA5 viable cells in a composition of the invention is at least $2 \times 10^{10}$ CFU per gram for solid compositions, and at least $2 \times 10^7$ CFU per millilitre for liquid compositions, preferably the concentration of YBCA5 viable cells in a composition of the invention is $2 \times 10^{10}$ CFU per gram for solid compositions, and $2 \times 10^7$ CFU per millilitre for liquid compositions.

The composition of the invention may comprise or consist essentially of YBCA5.

Concentrations of YBCA5 that are effective as a biological control agent in the composition of the invention may vary depending on the form the yeast is used in, physiological condition of the plant; type, concentration and degree of pathogen infection; temperature; season; humidity; soil type; stage in the growing season; age of the plant; number and type of conventional pesticides and fungicides being applied and plant treatments (such as pruning, but not limited thereto). All factors may be taken into account in formulating YBCA5 in the composition of the invention or in a composition for use in a method of the invention.

YBCA5 may be prepared for use in the invention using standard liquid fermentation techniques known in the art and as described in the examples herein. Growth is commonly effected under aerobic conditions in a bioreactor at suitable temperatures and pH for growth. Typical growth temperatures are from 10 to 30° C., preferably 15 to 28° C., preferably 25° C. Yeasts with optimal growth temperatures in the range of about 36-38° C. are not preferred for use due to the potential for human health risk. The pH of the growth medium is usually slightly acidic to neutral at pH 4.0 to 7.0, preferably 6.0.

Growth medium may be any known art medium suitable for culture of *Aureobasidium* species. In one embodiment the growth medium is potato dextrose agarose (PDA). Other suitable growth media include Malt Yeast Extract Agar; a proprietary liquid broth culture media comprising molasses and urea; and a proprietary liquid growth media comprising sugar, urea, yeast extract and mono ammonium phosphate (MAP).

The cells of YBCA5 may be harvested using conventional filtering or sedimentary techniques such as centrifugation, or may be harvested dry using continuous centrifugation. Cells can be used immediately or stored under chilled conditions (1° C. to 7° C., preferably 2° C.), or may be dried. Preferably, cells are dried and formulated as dry yeast granules. For example, cells may be dried using a fluidized bed drier, but not limited thereto. Preferably the dry yeast granules comprise at least 90% solids, preferably at least 95% solids, preferably about 96% solids. Preferably cells have a shelf life of at least two years. In one embodiment shelf life is at least six months, preferably at least one year, preferably at least two years wherein the cells are maintained under chilled conditions. Preferably chilled conditions are 10° C. or less, but greater than 0° C. Preferably chilled conditions are selected from the group consisting of 1° C., 2° C., 3° C., 4° C., 5° C., 6° C., 7° C., 8° C., 9° C. and 10° C. or variations within such temperatures from about 1° C. to about 10° C.

In one embodiment the composition comprises an agriculturally acceptable adjuvant. In one embodiment the agriculturally acceptable adjuvant is selected from the group consisting of an additional active agent and a formulation agent.

In one embodiment the agriculturally acceptable adjuvant is one or more additional active agents. In one embodiment the agriculturally acceptable adjuvant is one or more formulation agents.

In one embodiment the composition comprises a combination of one or more additional active agents and one or more formulation agents. In some embodiments the composition is formulated as pre-prepared composition or in a concentrated form. In some embodiments the composition comprises a solid or a liquid formulation.

In one embodiment composition of the invention comprises one or more agriculturally acceptable adjuvants. In one embodiment the agriculturally acceptable adjuvants are selected from the group of additional active agents and formulation agents. Preferably the one or more agriculturally acceptable adjuvant is an additional active agent. Preferably the one or more agriculturally acceptable adjuvant is a formulation agent.

In one embodiment the composition of the invention comprises a combination of one or more additional active agents and one or more formulation agents.

In some cases it may also be desirable to include one or more additional active agents in the compositions of the invention where such additional active agents are capable of contributing to the control (e.g., treatment and/or prevention) of plant pathogenic *Pseudomonas* spp. bacteria or plant pathogenic fungi including *Botrytis* spp., *Sclerotinia* spp., *Penicillium* spp., *Colletotrichum* spp., *Alternaria* spp., *Phomopsis* spp., *Cryptosporiopsis* spp., and *Monilinia* spp., but not limited thereto.

Suitable additional active agents for use in the present invention may be capable of controlling *Pseudomonas* spp., particularly Psa directly, or plant pathogenic fungi including *Botrytis* spp., *Sclerotinia* spp., *Penicillium* spp., *Colletotrichum* spp., *Alternaria* spp., *Phomopsis* spp., *Cryptosporiopsis* spp. and *Monilinia* spp. (but not limited thereto), or may be capable of potentiating the biocontrol effect of YBCA5 for controlling *Pseudomonas* spp., particularly Psa. Additional active agents may be included directly in the composition of or useful in the invention, or may be applied separately, either simultaneously or sequentially as appropriate according to a method of the invention.

Suitable additional active agents include, but are not limited to plant defence elicitors including acibenzolar-S-methyl (Actigard/Bion, Syngenta), Azelaic acid, Pipecolinic acid, Jasmonic acid, Seaweed Mix, Lema oil, Foodcoat (DOMCA), Fungicover (bioDURACAL agricultura) and Ibuprofen, antagonistic microorganisms, inorganic salts including calcium, potassium or sodium salts, stimulating agents including uronic acids, amnnans, and p 1-3 glucans, antibiotics, and other antibacterial and antifungal compounds including small organic and inorganic molecules.

By way of non-limiting example, one additional active agent that may be included in the composition of or for use in the invention is the plant defence elicitor acibenzolar-S-methyl (Actigard/Bion, Syngenta). Actigard is a plant activator with a unique mode of action which stimulates the natural systemic acquired resistance response found in most plant species. Applied via foliar application, Actigard has no direct activity against target pathogens, but helps to reduce Psa symptoms in Kiwifruit by inducing host plant resistance. Actigard is a composition comprising 500 g/kg acibenzolar-S-methyl in the form of a water dispersible granule.

In one embodiment the composition of the invention comprises one or more formulation agents.

In one embodiment the composition of the invention comprises a combination of one or more additional active agents and one or more formulation agents.

In one embodiment, the composition of the invention is formulated as a solid or a liquid formulation.

In one embodiment the composition of the invention may comprise one or more solid or liquid formulation agents. Any suitable formulation agent(s) may be used as known in the art. It is believed that the selection of a suitable formulation agent is within the skill of those in the art. For example, a suitable formulation agent may be a compound or other material that facilitates or optimizes the production, handling, storage, transport, application and/or persistence of the composition of, or for use in the invention on plants or on parts thereof, but not limited thereto.

Formulation agents can be specifically adapted for particular uses such as, but not limited to, preservation and maintenance of the biological control activity of the yeasts comprised in the composition of or for use in the invention during transportation from production facilities, storage on site, or during preparation of a final treatment mixture. Formulation agents may also be used for other purposes such as facilitating adhesion and persistence on plants or penetration into plant tissues, but not limited thereto. A suitable formulation may be solid, liquid, alone or in combination. Particularly suitable formulation agents include surfactants, dispersants, preservatives, wetting agents, emulsifiers, humectants, stickers, spreaders, stabilizers, penetrants, adhesion agents, pH buffers, and nutrients, either alone or in various combinations as may be determined by the skilled worker.

The composition of the invention may be provided as a pre-prepared composition ready for use, or in a concentrated, solid or liquid form.

In one embodiment, the composition is a pre-prepared composition having a solid or liquid formulation. In one embodiment the pre-prepared composition is a solid formulation selected from powders, pellets, granules and prills. In one embodiment the pre-prepared composition is a liquid formulation.

The composition of or for use in the invention may be provided in a pre-prepared form, or in a concentrated form. If provided in a dry form, the pre-prepared composition may be provided as a powder, granule, pellet or prill, but not limited thereto. In the case of a dry form, YBCA5 in the composition is preferably in dehydrated, dried and/or encapsulated form. In some embodiments, the dehydrated, dried and/or encapsulated forms include additional protective agents as known in the art; e.g., lyoprotectants and the like.

In one embodiment, YBCA5 may be provided in granule form. For example, YBCA5 may be provided in a granule having at least $0.5 \times 10^{10}$ CFU/gm, preferably $1 \times 10^{10}$ CFU/gm, preferably $2 \times 10^{10}$ CFU/gm. Where the pre-prepared composition is provided in a liquid form, particularly an aqueous form the composition may be provided as a dispersion, a suspension, a slurry, a cream, a paste or a gel, but not limited thereto. Preferably the pre-prepared form is provided as an aqueous liquid form that is suitable for and/or is adapted for spraying. In one embodiment a pre-prepared liquid form can be used per se for example as a dip to inoculate fruits, vegetables, seeds or plants, including plant cuttings.

In the pre-prepared composition of the invention, YBCA5 is formulated for use on plants, particularly kiwifruit vines. For example, the yeasts are mixed with an agriculturally acceptable carrier liquid that enables spray applications, a fertilizer, an elicitor, an adjuvant, a wetting agent, or any other suitable additional agent as required. In the pre-prepared composition for use according to the methods of the invention, YBCA5 may also be mixed with an agriculturally acceptable carrier liquid that enables spray applications, a fertilizer, an elicitor, an adjuvant, a wetting agent, or any other suitable additional agent as required.

The formulation of YBCA5 into a pre-prepared composition of the invention and the final form of the pre-prepared composition for application to the plant or part thereof is believed to be within the skill in the art. For example, the final form of the composition is formulated with an agriculturally acceptable carrier such as water to form a spray, foam, drench, injectable, gel, dip or paste, but not limited thereto. In one embodiment, a composition of the invention may be applied to plants or parts thereof by spraying, dipping, rubbing or brushing, or a combination thereof. Preferably the composition is formulated as an aqueous suspension or dispersion for spray or mist application to kiwifruit vines, cherry trees and/or fruit and grape vines and/or fruit and/or vegetables.

In one embodiment the composition of the invention is in concentrated form. In one embodiment the concentrated form is a solid form selected from cakes, powders, granules, pellets and prills. In one embodiment the concentrated form is a liquid formulation.

Where the composition of the invention is provided in a concentrated form it may require additional formulation by the user to produce a composition ready for application to a plant or part thereof. For example, the concentrated form can be mixed with various formulation agents to form a final composition for plant application. A preferred formulation is agent is water or an aqueous solution in which an appropriate amount of the concentrated from of the composition is dissolved (e.g., granules or powders) or diluted (e.g., liquid suspensions or dispersions) to obtain a final composition for application to a plant.

If the YBCA5 is dehydrated in the concentrated form then rehydration as known in the art will be required if the composition for application to the plant is intended to be in liquid form. Rehydration may be carried out using customary precautions for rehydrating the yeast as known in the art; for example rehydration may be achieved advantageously at temperatures between 20 and 25° C., but not limited thereto.

Methods—*Pseudomonas* Spp.

In another aspect the invention relates to a method of controlling *Pseudomonas* spp. bacteria on a plant or part thereof, the method comprising contacting the plant or part thereof with YBCA5, or a composition comprising YBCA5.

In another aspect the invention relates to the use of YBCA5, or a composition comprising YBCA5 for controlling *Pseudomonas* spp. bacteria on a plant or part thereof.

In one embodiment the method or use comprises contacting the plant or part thereof with reproductively viable cells of YBCA5.

In some embodiments the concentration of YBCA5 viable cells in a composition of the invention ranges from about $1 \times 10^3$ to about $1 \times 10^{14}$, preferably about $1 \times 10^5$ to about $1 \times 10^{11}$, preferably about $1 \times 10^6$ to about $1 \times 10^9$, preferably about $1 \times 10^7$ to about $1 \times 10^8$, preferably about $2 \times 10^7$ to about $2 \times 10^8$ CFU, preferably about $2 \times 10^9$ to about $2 \times 10^{10}$ CFU per gram for solid compositions, and about $1 \times 10^7$ to about $1 \times 10^8$ CFU per millilitre for liquid compositions.

In some embodiments the concentration of YBCA5 viable cells in a composition of the invention ranges from $1 \times 10^3$ to about $1 \times 10^{14}$, preferably $1 \times 10^5$ to about $1 \times 10^{11}$, preferably from $1 \times 10^6$ to about $1 \times 10^9$, preferably $1 \times 10^7$ to about $1 \times 10^8$, preferably from $2 \times 10^7$ to about $2 \times 10^8$ CFU, preferably from $2 \times 10^9$ to about $2 \times 10^{10}$ CFU per gram for solid compositions, and from $1 \times 10^7$ to about $1 \times 10^8$ CFU per millilitre for liquid compositions.

In some embodiments the concentration of YBCA5 viable cells in a composition of the invention ranges from about $1 \times 10^3$ to $1 \times 10^{14}$, preferably about $1 \times 10^5$ to $1 \times 10^{11}$, preferably about $1 \times 10^6$ to $1 \times 10^9$, preferably about $1 \times 10^7$ to $1 \times 10^8$, preferably about $2 \times 10^7$ to $2 \times 10^8$ CFU, preferably about $2 \times 10^9$ to $2 \times 10^{10}$ CFU per gram for solid compositions, and about $1 \times 10^7$ to $1 \times 10^8$ CFU per millilitre for liquid compositions.

In some embodiments the concentration of YBCA5 viable cells in a composition of the invention ranges from $1 \times 10^3$ to $1 \times 10^{14}$, preferably $1 \times 10^5$ to $1 \times 10^{11}$, preferably $1 \times 10^6$ to $1 \times 10^9$, preferably $1 \times 10^7$ to $1 \times 10^8$, preferably $2 \times 10^7$ to $2 \times 10^8$ CFU, preferably $2 \times 10^9$ to $2 \times 10^{10}$ CFU per gram for solid compositions, and $1 \times 10^7$ to $1 \times 10^8$ CFU per millilitre for liquid compositions.

In some embodiments the concentration of YBCA5 viable cells in a composition of the invention is about $2 \times 10^{10}$ CFU per gram for solid compositions, and about $2 \times 10^7$ CFU per millilitre for liquid compositions.

In some embodiments the concentration of YBCA5 viable cells in a composition of the invention is at least $2 \times 10^{10}$ CFU per gram for solid compositions, and at least $2 \times 10^7$ CFU per millilitre for liquid compositions, preferably the concentration of YBCA5 viable cells in a composition of the invention is $2 \times 10^{10}$ CFU per gram for solid compositions, and $2 \times 10^7$ CFU per millilitre for liquid compositions.

In one embodiment the at least one strain of *Pseudomonas* spp. is selected from the group consisting of *P. syringae*, *P. amygdalia*, *P. avellanae*, *P. caricapapayae*, *P. cichorii*, *P. coronafaciens*, *P. ficuserectae*, *P. helianthi*, *P. lemiae*, *P. savastanoi*, and *P. viridiflava*, or a pathovar thereof, or combinations thereof. Preferably the at least one strain is *P.*

*syringae* or a pathovar thereof, more preferably the at least one strain is *P. syringae* pv. *actinidiae* (Psa).

In one embodiment the plant or part thereof is selected from the group of monocotyledonous plants, dicotyledonous plants, annual, biannual and perennial plants, vegetable plants or harvested vegetables, fruit plants or trees or harvested fruits, flower bearing plants or trees or harvested flowers, cereal plants, oleaginous plants, proteinous plants, ligneous plants, and ornamental plants.

In one embodiment the plant or part thereof is an agriculturally important plant, cultivar thereof, or product thereof selected from the group consisting of agriculturally important vines, agriculturally important vegetables and agriculturally important fruit plants, and cultivars and products thereof. Preferably the agriculturally important vine is a kiwifruit vine or cultivar thereof, and the product is kiwifruit.

In one embodiment the kiwifruit vine is selected from the group consisting of species of green-fleshed kiwifruit (*A. chinensis* var. *deliciosa*), golden kiwifruit (*A. chinensis* var. *chinensis*), Chinese egg gooseberry (*A. coriacea*), baby kiwifruit (*A. arguta*), Arctic kiwifruit (*A. kolomikta*), red kiwifruit (*A. melanandra, A. chinensis* var. *chinensis*), silver vine (*A. polygama*), and purple kiwifruit (*A. purpurea*) or a cultivar thereof. Preferably the kiwifruit are selected from the group consisting of *A. chinensis* var. *deliciosa* and *A. chinensis* var. *chinensis*, species or a cultivar thereof. Preferably the kiwifruit is a species of *A. chinensis* var. *chinensis*. Preferably the kiwifruit is *A. chinensis* var. *chinensis* Planch. Preferably the cultivar is a 'Hayward' or 'Hort16A' or 'zesy002', informally known as Gold3 or 'Hongyang'.

In one embodiment the cultivar is *A. chinensis* var. *chinensis* Planch, 'Hort16A'. In one embodiment the cultivar is 'Hort16A' as disclosed in USPP11066, the entirety of which is incorporated by reference herein.

In one embodiment the cultivar is *A. chinensis* var. *deliciosa* 'Hayward'. In one embodiment the cultivar is 'Hayward' as disclosed in USPP6815, the entirety of which is incorporated by reference herein.

In one embodiment cultivar is *A. chinensis* var. *chinensis* Planch. 'Hongyang'. In one embodiment the cultivar is 'Hongyang' as disclosed in Wang 2011 and in Li et al 2015, the entirety of which are incorporated by reference herein.

In another aspect the invention relates to YBCA5, or a composition comprising YBCA5 for use in, or when used, for controlling *Pseudomonas* spp. bacteria on a plant or part thereof.

The use of YBCA5, or a composition comprising YBCA5 for controlling *Pseudomonas* spp., bacteria and/or for increasing the yield of a kiwifruit plant is carried out in accordance with the methods of the invention as described herein. For example, YBCA5 and compositions thereof may be prepared, formulated for and applied to a plant, or part thereof, particularly a kiwifruit plant, or part thereof, according to the invention as described herein.

In another aspect the invention relates to a method of controlling at least one phytopathogenic fungus on a plant or part thereof, the method comprising contacting the plant or part thereof with YBCA5, or a composition comprising YBCA5.

In another aspect the invention relates to a method for increasing the yield of a fruit or vegetable plant susceptible to infection by a phytopathogenic fungus, the method comprising applying YBCA5, or a composition comprising YBCA5 to the fruit or vegetable plant or part thereof, and growing the plant or part thereof. In one embodiment the composition consists essentially of YBCA5.

In one embodiment the at least phytopathogenic fungus is selected from the group consisting of *Botrytis* spp., *Monilinia* spp., *Sclerotinia* spp., *Colletotrichum* spp., *Alternaria* spp., *Cryptosporiopsis* spp., *Phomopsis* spp., and *Penicillium* spp.

In one embodiment the plant or part thereof is selected from the group of monocotyledonous plants, dicotyledonous plants, annual, biannual and perennial plants, vegetable plants or harvested vegetables, fruit plants or trees or harvested fruits, flower bearing plants or trees or harvested flowers, cereal plants, oleaginous plants, proteinous plants, ligneous plants, and ornamental plants.

In one embodiment the plant or part thereof is an agriculturally important plant, cultivar thereof, or product thereof selected from the group consisting of agriculturally important vines and agriculturally important fruit trees, agriculturally important vegetables and cultivars and products thereof. In one embodiment the agriculturally important vine is a kiwifruit vine or cultivar thereof, and the product is kiwifruit.

In one embodiment the plant or part thereof is a fruit or vegetable plant or part thereof, the method comprising contacting the fruit or vegetable plant or part thereof with YBCA5, or a composition comprising YBCA5. In some embodiments the fruit or vegetable plant is a cherry tree or a grape vine. In some embodiments the fruit plant is an apple tree.

In one embodiment the cherry tree is a *Prunus* spp., or a cultivar thereof, preferably a *P. avium*, or cultivar thereof. Preferably the *P. avium* is a "Sweet Valentine" variety. In one embodiment the part thereof is a flower or part thereof or a fruit or part thereof. In one embodiment the fruit is a cherry.

In one embodiment the grape vine is a *Vinus* spp., or a cultivar thereof, preferably a *V. vinifera*, or cultivar thereof. Preferably the *V. vinifera* is a "Thompson Seedless" variety. In one embodiment the part thereof is a flower or part thereof or a fruit or part thereof. In one embodiment the fruit is a grape.

In one embodiment the apple tree is a *Malus* spp., or a cultivar thereof, preferably *M. pumila* or cultivar thereof. Preferably the *M. pumila* or a cultivar thereof is a 'Pacific Rose' variety. In one embodiment the part thereof is a flower or part thereof, or a fruit or part thereof. In one embodiment the fruit is an apple.

Psa Control

In another aspect the invention relates to a method for controlling *P. syringae* pv. *actinidiae* (Psa) on a kiwifruit plant or part thereof, the method comprising contacting the kiwifruit plant or part thereof with YBCA5, or a composition comprising YBCA5.

In another aspect the invention relates to a method for increasing the yield of a kiwifruit plant infected, or susceptible to infection with Psa, the method comprising applying YBCA5 or a composition comprising YBCA5 to the kiwifruit plant or part thereof, and growing the kiwifruit plant or part thereof.

In another aspect the invention relates to the use of YBCA5, or a composition comprising YBCA5 for controlling Psa on a kiwifruit plant or part thereof.

In another aspect the invention relates to the use of YBCA5, or a composition comprising YBCA5 for increasing the yield of a kiwifruit plant infected, or susceptible to infection with Psa.

In one embodiment the composition consists essentially of YBCA5.

In one embodiment, the kiwifruit plant is a species of *A. chinensis* var. *deliciosa* or *A. chinensis* var. *chinensis*, or a cultivar thereof, preferably a species of *A. chinensis* var. *chinensis*, or cultivar thereof. In one embodiment the kiwifruit plant is 'Hort16A'.

In one embodiment cultivar is *A. chinensis* var. *chinensis* 'Hongyang'. In one embodiment the cultivar is 'Hongyang' as disclosed in Wang 2011 and in Li et al 2015, the entirety of which are incorporated by reference herein.

In one embodiment a plant or part thereof is contacted for a time sufficient to control Psa.

In one embodiment, contacting comprises applying YBCA5 or a composition comprising or consisting essentially of YBCA5 to the plant or part thereof by applying to the seeds, leaves, stems, flowers, fruits, trunks and/or roots of the plant or part thereof. Preferably application is by spraying, misting, dipping, dripping, dusting or sprinkling. Applications can be made once only, or repeatedly as required. Also contemplated herein is application at various times of year and/or during various stages of the plant life cycle, as determined appropriate by the skilled worker.

YBCA5 may be applied at the appropriate time during the year and at the appropriate stage of plant development as may be determined by a skilled worker. For example YBCA5 may be applied from bud-burst to flowering, during flowering and post flowering/fruit set period but not limited thereto.

In one embodiment, applying is by spraying onto leaf surfaces and/or onto flowers and/or onto fruit and/or onto vegetables.

In one embodiment, applying to the roots is by ground spraying, mechanical incorporation or by mixing with enriching agents or fertilizers prior to application in the usual way.

In one embodiment the plant or part thereof is selected from monocotyledonous plants, dicotyledonous plants, annual, biannual and perennial plants, vegetable plants or harvested vegetables, fruit plants or trees or harvested fruits, flower bearing plants or trees or harvested flowers, cereal plants, oleaginous plants, proteinous plants, ligneous plants, and ornamental plants.

In one embodiment, a plant or part thereof is an agriculturally important crop plant, cultivar or product thereof selected from corn plants, tobacco plants, wheat plants, sugar cane plants, rapeseed plants, barley plants, rice plants, sorghum plants, millet plants, soya bean plants, lettuce plants, and cabbage plants.

In one embodiment the plant or part thereof is an agriculturally important plant, cultivar thereof, or product thereof selected from the group consisting of agriculturally important vines and agriculturally important fruit trees, and cultivars and products thereof. Preferably the agriculturally important fruit trees or cultivars thereof are selected from olive trees, apple trees, pear trees, citrus fruit trees, banana trees, pineapple trees, peach trees, apricot trees, cherry trees, walnut trees and hazelnut trees and the products thereof are olives, apples, pears, citrus fruits, bananas, pineapples, peaches, apricots, cherries, walnuts and hazelnuts respectively. Preferably the agriculturally important vines or cultivars thereof are selected from potato vines, beetroot vines, bean vines, pea vines, tomato vines, cucumber vines, melon vines, berry vines, grape vines and kiwifruit vines and the products thereof are potatoes, beetroots, beans, peas, tomatoes, cucumbers, melons, berries, grapes and kiwifruits respectively. Preferably the agriculturally important vine is a kiwifruit vine or cultivar thereof, and the product is kiwifruit.

Kiwifruit are within the plant order Ericales and the family Actinidiaceae. In one embodiment the kiwifruit vine is selected from the group consisting of species of fuzzy kiwifruit (*A. chinensis* var. *deliciosa*), golden kiwifruit (*A. chinensis* var. *chinensis*), Chinese egg gooseberry (*A. coriacea*), baby kiwifruit (*A. arguta*), Arctic kiwifruit (*A. kolomikta*), red kiwifruit (*A. melanandra, A. chinensis* var. *chinensis*), silver vine (*A. polygama*), and purple kiwifruit (*A. purpurea*) or a cultivar thereof. Preferably the kiwifruit are selected from the group consisting of *A. chinensis* var. *deliciosa, A. chinensis* var. *chinensis* species or a cultivar thereof. Preferably the kiwifruit is a species of *A. chinensis* var. *chinensis*. Preferably the preferably kiwifruit is *A. chinensis* var. *chinensis* Planch. Preferably the cultivar is a 'Hayward' or 'Hort 16A' or 'Zesy002' or 'Zesy004' or 'Hongyang' variety cultivar.

In one embodiment the cultivar is *A. chinensis* var. *chinensis* Planch, 'Hort 16A'. In one embodiment the cultivar is 'Hort 16A' as disclosed in USPP11066, the entirety of which is incorporated by reference herein.

In one embodiment cultivar is *A. chinensis* var. *deliciosa* 'Hayward'. In one embodiment the cultivar is 'Hayward' as disclosed in USPP6815, the entirety of which is incorporated by reference herein.

In one embodiment cultivar is *A. chinensis* var. *chinensis* 'Hongyang'. In one embodiment the cultivar is 'Hongyang' as disclosed in Wang 2011 and in Li et al 2015, the entirety of which are incorporated by reference herein.

In another aspect the invention relates to YBCA5, or a composition comprising YBCA5 for use in, or when used, for controlling Psa on a kiwifruit plant or part thereof.

In another aspect the invention relates to YBCA5, or a composition comprising YBCA5 for use in, or when used, for increasing the yield of a kiwifruit plant infected, or susceptible to infection with Psa.

The use of YBCA5, or a composition comprising YBCA5 for controlling Psa and/or for increasing the yield of a kiwifruit plant is carried out in accordance with the methods of the invention as described herein. For example, YBCA5 and compositions thereof may be prepared, formulated for and applied to a plant, or part thereof, particularly a kiwifruit plant, or part thereof, according to the invention as described herein.

In another aspect the invention relates to at least one plant or part thereof treated with YBCA5, or a composition comprising YBCA5. In some embodiments the plant is a fruit or vegetable plant or part thereof. In one embodiment the plant is a kiwifruit vine, a cherry tree or a grape vine.

Phytopathogenic Fungal Control

In another aspect the invention relates to a method of controlling at least one phytopathogenic fungus on a plant or part thereof, the method comprising contacting the plant or part thereof with YBCA5, or a composition comprising YBCA5.

In another aspect the invention relates to a method for increasing the yield of a fruit or vegetable plant susceptible to infection by a phytopathogenic fungus, the method comprising applying YBCA5, or a composition comprising YBCA5 to the fruit or vegetable plant or part thereof, and growing the plant or part thereof.

In another aspect the invention relates to the use of YBCA5, or a composition comprising YBCA5 for controlling a phytopathogenic fungus on a fruit or vegetable plant or part thereof.

In another aspect the invention relates to the use of YBCA5, or a composition comprising YBCA5 for increasing the yield of a fruit or vegetable plant or part thereof susceptible to infection by a phytopathogenic fungus.

In another aspect the invention relates to YBCA5, or a composition comprising YBCA5 for use in, or when used, for controlling at least one phytopathogenic fungus on a plant or part thereof.

In another aspect the invention relates to YBCA5, or a composition comprising YBCA5 for use in, or when used, for controlling at least one phytopathogenic fungus on a fruit or vegetable plant or part thereof.

In another aspect the invention relates to YBCA5, or a composition comprising YBCA5 for use in, or when used, for increasing the yield of a fruit or vegetable plant susceptible to infection by at least one phytopathogenic fungus.

The following embodiments are also specifically contemplated for those aspects of the invention that relate to the use of YBCA5, or to a composition comprising or consisting essentially of YBCA5, for controlling phytopathogenic fungi and/or for increasing the yield of a plant or part thereof, or of a fruit or vegetable plant or part thereof, susceptible to infection by a phytopathogenic fungus.

In one embodiment the phytopathogenic fungus is selected from the group consisting of *Botrytis* spp., *Monilinia* spp., *Sclerotinia* spp., *Colletotrichum* spp., *Alternaria* spp., *Cryptosporiopsis* spp., *Phomopsis* spp., and *Penicillium* spp.

In one embodiment the plant or part thereof is selected from the group of monocotyledonous plants, dicotyledonous plants, annual, biannual and perennial plants, vegetable plants or harvested vegetables, fruit plants or trees or harvested fruits, flower bearing plants or trees or harvested flowers, cereal plants, oleaginous plants, proteinous plants, ligneous plants, and ornamental plants.

In one embodiment the plant or part thereof is an agriculturally important plant, cultivar thereof, or product thereof selected from the group consisting of agriculturally important vines and agriculturally important fruit trees, agriculturally important vegetables and cultivars and products thereof. In one embodiment the agriculturally important vine is a kiwifruit vine or cultivar thereof, and the product is kiwifruit.

In one embodiment the plant or part thereof is a fruit or vegetable plant or part thereof, the method comprising contacting the fruit or vegetable plant or part thereof with YBCA5, or a composition comprising YBCA5. In some embodiments the fruit or vegetable plant is a cherry tree or a grape vine. In some embodiments the fruit plant is an apple tree.

In one embodiment the cherry tree is a *Prunus* spp., or a cultivar thereof, preferably a *P. avium*, or cultivar thereof. Preferably the *P. avium* is a "Sweet Valentine" variety. In one embodiment the part thereof is a flower or part thereof or a fruit or part thereof. In one embodiment the fruit is a cherry.

In one embodiment the grape vine is a *Vinus* spp., or a cultivar thereof, preferably a *V. vinifera*, or cultivar thereof. Preferably the *V. vinifera* is a "Thompson Seedless" variety. In one embodiment the part thereof is a flower or part thereof or a fruit or part thereof. In one embodiment the fruit is a grape.

In one embodiment the apple tree is a *Malus* spp., or a cultivar thereof, preferably *M. pumila* or a cultivar thereof. Preferably the *M. pumila* is a 'Pacific Rose' variety. In one embodiment the part thereof is a flower or part thereof, or a fruit or part thereof. In one embodiment the fruit is an apple.

In another aspect the invention relates to at least one plant or part thereof treated with YBCA5, or a composition comprising YBCA5.

In another aspect the invention relates to at least one fruit or vegetable plant or part thereof treated with YBCA5, or a composition comprising YBCA5.

In one embodiment the composition consists essentially of YBCA5.

The use of YBCA5, or a composition comprising or consisting essentially of YBCA5 for controlling phytopathogenic fungi and/or for increasing the yield of a plant or part thereof, or of a fruit or vegetable plant or part thereof is carried out in accordance with the methods and uses of the invention as described herein. For example, YBCA5 and compositions thereof may be prepared, formulated for and applied to a plant, or part thereof, particularly a fruit or vegetable plant, or part thereof, particularly a cherry tree or grape vine, according to the invention as described herein.

Various aspects of the invention will now be illustrated in non-limiting ways by reference to the following examples.

EXAMPLES

Example 1—Identification of Yeasts with Biocontrol Activity

Yeast Screening

YBCA5 was isolated from Apricots ("Clutha Gold") from central Otago in the early 2000s as follows. Fresh, harvested apricots were frozen overnight at −20° C. and then incubated at 20° C. for up to 5 days. Yeast or yeast-like colonies growing on the surface of selected apricots were isolated using standard protocols on a general culturing medium suitable for yeast propagation.

Example 2—Yeast Biocontrol of *Pseudomonas syringae* Var. *Actinidiae* (Psa)

General Methodologies

Plant-based screening assays were conducted in laboratories and glasshouses at the Ruakura Research Centre, Hamilton and at the Te Puke Research Orchard, Te Puke, New Zealand. Plant and Food (PFR) assays focused on foliar application of biological control agents (BCAs), particularly YBCA5 and other PFR proprietary yeast strains.

Zespri Assay 26—Dose Rate of YBCA5

The aim of this assay was to compare several dose rates of freshly fermented YBCA5 with a formulated and dried preparation of YBCA5 for their efficacy against Psa.

Plant Material

Zespri Assay 26 was carried out in the PC1 glasshouse at Ruakura using tissue cultured *A. chinensis* var. *deliciosa* 'Hayward' plants grown in 1 L pots. Plants were 30-50 cm high, each with at least 4-5 useable leaves per plant and the time of treatment and there were 10 replicate plants per treatment.

Yeast Preparation

Freshly fermented YBCA5 was obtained by fermenting the yeast for 3 days in a 10 L bioreactor (Labfors) using sterile liquid media (4% molasses and 1.2 g/L urea). The fermentate was spun in a centrifuge (Sorvall RC-5C) at 5000 rpm for 15 min (rotor no. SLC-4000, rotorcode 33) to achieve a wet pellet of cell concentrate after discarding the supernatant. A sub-sample of wet pellet was re-suspended and the cell density determined with the aid of a haemocytometer and appropriate dilutions made to achieve final spray concentrations of $6 \times 10^6$, $1.25 \times 10^7$, $2.5 \times 10^7$ and $5.0 \times 10^7$ CFU/mL.

YBCA5 granules were prepared by mixing the wet pellet from a previous fermentation in the 10 L fermenter, with approximately 30% (w/w) cornstarch to form a stiff dough consistency and this was extruded through a steel mesh (3 mm hole size) and dried in a laminar flow hood overnight (20-25° C.) to form dried granules.

The number of CFU in the dried granules of YBCA5 was calculated by thoroughly dissolving 0.2 g granule into 20 mL of PBSTw. Serial dilutions of this stock were carried out (to 10-6) and three 10 µl droplets of each dilution were transferred onto MYA. The number of yeast colonies growing from each droplet were counted after 24 h incubation at 25° C. followed by a further 24 h incubation in a fridge (4-6° C.). A spray concentration of $2.5\times10^7$ CFU/mL was prepared be weighing the appropriate quantity of granules into 500 mL water.

Psa Inoculum Preparation

A Psa culture (isolate code 10627, biovar 3), which had been isolated from an infected *Actinidia chinensis* var. *chinensis* 'Hort16A' kiwifruit vine located in the Te Puke region during 2010, was used for all stab and spray inoculation assays included in this report (Vanneste et al. 2013). Psa inoculum was prepared by growing this strain of Psa for 2-3 days on King's B (KB) medium and harvesting the bacteria by washing the plate with sterile distilled water (SDW) to make a stock suspension of inoculum that was visually determined to be c.>$1\times10^9$ CFU/mL. A subsample of this Psa stock was serially diluted and 10-μL droplets placed onto fresh KB medium so that the number of CFU/mL could be counted after two days' incubation. To facilitate droplet inoculation in the glasshouse (Ruakura), Psa inoculum (stock solution c.$\times10^9$ CFU/mL) optical density was determined using a spectrophotometer (600 nm) and then the solution was diluted with sterile PBS to give resultant suspensions of $5\times10^8$ CFU/mL and $2\times10^7$ CFU/mL, based on a previously developed calibration curve. The adjuvant, Du-Wett was then added to the suspension to give a final concentration of 0.03% (v/v).

Leaf Spray Inoculation Assay

On 11 and 18 Sep. 2014, spray treatments of each freshly fermented YBCA5 concentration and the granule preparation were applied to run-off to all leaves on each plant that had been grown in pots in a glasshouse, 7 and 1 days before inoculation (dbi) with the two doses of Psa and plants were allowed to dry in a spray containment shed. Once dried, the spray treated plants were returned to the glasshouse. One day after the second spray treatment with YBCA5, on 19 Sep. 2014 the Psa inoculum was pipetted (10 μL) onto the underside of each leaf in pairs on either side of the mid-rib of four or five selected leaves (avoiding the oldest and the youngest leaves). Plants were then placed into high-humidity tents in containment glasshouses at PFR Ruakura after inoculation with Psa for up to three weeks and then scored for Psa severity.

Measurement of Psa Symptoms

The area ($mm^2$) of necrosis caused by Psa was visually estimated for each inoculation point 21 days after Psa droplet inoculation. In order to ensure consistency, only two staff members carried out Psa leaf severity assessments with regular cross-checking of the severity scores.

Statistical Analysis

All data were analysed using GenStat following natural log transformation. Raw data means are presented and statistical differences are based on the log transformed analysis.

KR/P-BCA Assay 39

The aim of this assay was to investigate the fermentation, formulation and efficacy against Psa of different isolates of *Aureobasidium pullulans* compared with YBCA5.

Plant Material

KRIP-BCA Assay 39 was carried out in the PC1 glasshouse at Ruakura using tissue cultured *A. chinensis* var. *deliciosa* 'Hayward' plants grown in 1.5 L pots. Plants were 30-50 cm high, each with at least 4-5 useable leaves per plant and the time of treatment and there were 10 replicate plants per treatment.

Yeast Preparation

YBCA5 granules were prepared by fermenting the yeast for 3 days in a 10 L bioreactor (Labfors) using sterile liquid media (4% molasses and 1.2 g/L urea). The fermentate was spun in a centrifuge (Sorvall RC-5C) at 5000 rpm for 15 min (rotor no. SLC-4000, rotorcode 33) to achieve a wet pellet of cell concentrate after discarding the supernatant. This wet pellet was mixed with approximately 30% (w/w) cornstarch to form a stiff dough consistency and this was extruded through a steel mesh (3 mm hole size) and dried in a laminar flow hood overnight (20-25° C.) to form dried granules.

Twelve *A. pullulans* isolates selected from a large culture collection were fermented for 3 days in flask culture (200 mL of 4% molasses 1.2 g/L urea sterile liquid media in 500 mL conical flasks). The number of viable colony forming units (CFU) was determined by sub-sampling 1 mL of fermentate and carrying out serial dilutions (to 10-7) in 0.05M phosphate buffered saline+0.05% Tween80 (PBSTw). For each dilution three 10 μl droplets were transferred onto Malt Yeast Extract Agar (MYA). This number of yeast colonies growing from each droplet were counted after 24 h incubation at 25° C. followed by a further 24 h incubation in a fridge (4-6° C.). The fermentate was then processed as described above for YBCA5 to form dried formulated granules.

The number of CFU in the dried granules for each *A. pullulans* isolate was calculated by thoroughly dissolving 0.2 g granule into 20 mL of PBSTw. Serial dilutions of this stock were carried out (to 10-6) and three 10 μl droplets of each dilution were transferred onto MYA. This number of yeast colonies growing from each droplet were counted after 24 h incubation at 25° C. followed by a further 24 h incubation in a fridge (4-6° C.). Compositions for spray applications were prepared by weighing the appropriate quantity of granules into 500 mL water.

Psa Inoculum Preparation

A Psa culture (isolate code 10627, biovar 3), which had been isolated from an infected *Actinidia chinensis* var. *chinensis* 'Hort16A' kiwifruit vine located in the Te Puke region during 2010, was used for all stab and spray inoculation assays included in this report (Vanneste et al. 2013). Psa inoculum was prepared by growing this strain of Psa for 2-3 days on King's B (KB) medium and harvesting the bacteria by washing the plate with sterile distilled water (SDW) to make a stock suspension of inoculum that was visually determined to be c.>$1\times10^1$ CFU/mL. A subsample of this Psa stock was serially diluted and 10-μL droplets placed onto fresh KB medium so that the number of CFU/mL could be counted after two days' incubation. To facilitate droplet inoculation in the glasshouse (Ruakura), Psa inoculum (stock solution c.$\times10^9$ CFU/mL) optical density was determined using a spectrophotometer (600 nm) and then the solution was diluted with sterile PBS to give resultant suspensions of $1\times10^8$ CFU/mL, based on a previously developed calibration curve. The adjuvant, Du-Wett was then added to the suspension to give a final concentration of 0.03% (v/v).

Leaf Spray Inoculation Assays

On 9 May 2016, spray treatments of each *A. pullulans* isolate and YBCA5 were applied to run-off to all leaves on each plant that had been grown in pots in a glasshouse, 7 days before inoculation (dbi) with Psa ($1\times10^8$ CFU/mL). All *A. pullulans* treatments, including YBCA5 were applied at a final concentration of $2\times10^7$ CFU/mL and plants were allowed to dry in a spray containment shed. Once dried, the spray treated plants were returned to the glasshouse. Seven days after spray treatment, on 16 May 2016 the Psa inoculum dose was pipetted (10 µL) onto the underside of each leaf in pairs on either side of the mid-rib of four or five selected leaves (avoiding the oldest and the youngest leaves). Plants were then placed into high-humidity tents in containment glasshouses at PFR Ruakura after inoculation with Psa for up to three weeks and then scored for Psa severity.

Measurement of Psa Symptoms

The area ($mm^2$) of necrosis caused by Psa was visually estimated for each inoculation point 21 days after Psa droplet inoculation. In order to ensure consistency, only two staff members carried out Psa leaf severity assessments with regular cross-checking of the severity scores.

Statistical Analysis

All data were analysed using GenStat following natural log transformation. Raw data means are presented and statistical differences are based on the log transformed analysis.

Results—Dose Rate Assay

FIG. 1 shows that YBCA5 is very effective at reducing the severity of Psa symptoms on 'Hayward' kiwifruit leaves. All dose rates used in this experiment significantly reduced ($P<0.001$) the severity of leaf necrosis compared with the untreated control. There was not difference in efficacy in the YBCA5 granule preparation compared with freshly fermented YBCA5.

Results—Fermentation and Formulation

The fermentation yield for the 12 flask grown *A. pullulans* isolates ranged from $1.3\times10^8$ CFU/mL to $2.3\times10^9$ CFU/mL and the fermentation yield for flask grown YBCA5 was $3.3\times10^8$ CFU/mL (Table 1), indicating that some isolates are capable of producing higher fermentation yields compared with YBCA5, while others produce lower fermentation yields.

The number of CFU/g for dried granules of YBCA5 (from 10 L fermentation) was $2.3\times10^{10}$ and for the 12 isolates of *A. pullulans* the number of CFU/g for dried granules ranged from a low of $3.1\times10^9$ CFU/g to $2.0\times10^{10}$ CFU/g (Table 1), indicating that most *A. pullulans* isolates produced a lower yield of viable CFU/g than YBCA5.

A comparison of the number of CFU in the granules per mL of fermentation liquid (to allow a more direct comparison of the 10 L fermentation of YBCA5 and the flask culture of the 12 *A. pullulans* isolates) shows that the YBCA5 has the highest yield ($4\times10^8$ CFU/mL) and for the other *A. pullulans* isolates this ranged from as low as $4.2\times10^7$ CFU/mL to $2.4\times10^8$ CFU/mL (Table 1).

TABLE 1

Fermentation yield and formulation yield for a range of *Aureobasidium pullulans* isolates, including YBCA5.

| *A. pullulans* culture code | Conical flask yield (spores/mL) | Granules dried weight (g) | Granule CFU/g | Total spores | Granule CFU/mL of fermentation liquid |
|---|---|---|---|---|---|
| YBCA5 | 3.3E+08 | 174* | 2.30E+10* | 4.04E+12* | 4.0E+08* |
| CG173 | ND** | 9 | 2.00E+10 | 1.80E+11 | 2.2E+08 |
| HB 229 | ND | 9.4 | 1.40E+10 | 1.30E+11 | 1.6E+08 |
| HRY 212 | ND | 7.6 | 1.80E+10 | 1.40E+11 | 1.7E+08 |
| HB 228 | ND | 9.8 | 1.90E+10 | 1.90E+11 | 2.4E+08 |
| HB226 | 2.3E+09 | 12 | 1.60E+10 | 1.90E+11 | 2.4E+08 |
| HB201 | 1.4E+08 | 9.9 | 6.10E+09 | 6.00E+10 | 7.5E+07 |
| FOR 5-8-1 | 2.3E+09 | 10 | 1.60E+10 | 1.60E+11 | 2.0E+08 |
| GIS 08 4/1 | 2.3E+09 | 13.7 | 5.30E+09 | 7.30E+10 | 9.1E+07 |
| HB 303 | 8.8E+09 | 10.8 | 3.10E+09 | 3.40E+10 | 4.2E+07 |
| FOR6-1-1 | 1.3E+08 | 10.7 | 9.80E+09 | 1.10E+11 | 1.4E+08 |
| HBR018 | 2.3E+08 | 7.9 | 1.50E+10 | 1.20E+11 | 1.5E+08 |
| MSB 8-6-2 | 2.6E+08 | 8 | 1.10E+10 | 8.80E+10 | 1.1E+08 |

*For YBCA5 this data is the mean of three batches fermented using the 10 L fermenter.
**ND = No data.

Results—Leaf Droplet Inoculation Assay—Efficacy (KRIP-BCA 39)

Figure 2:
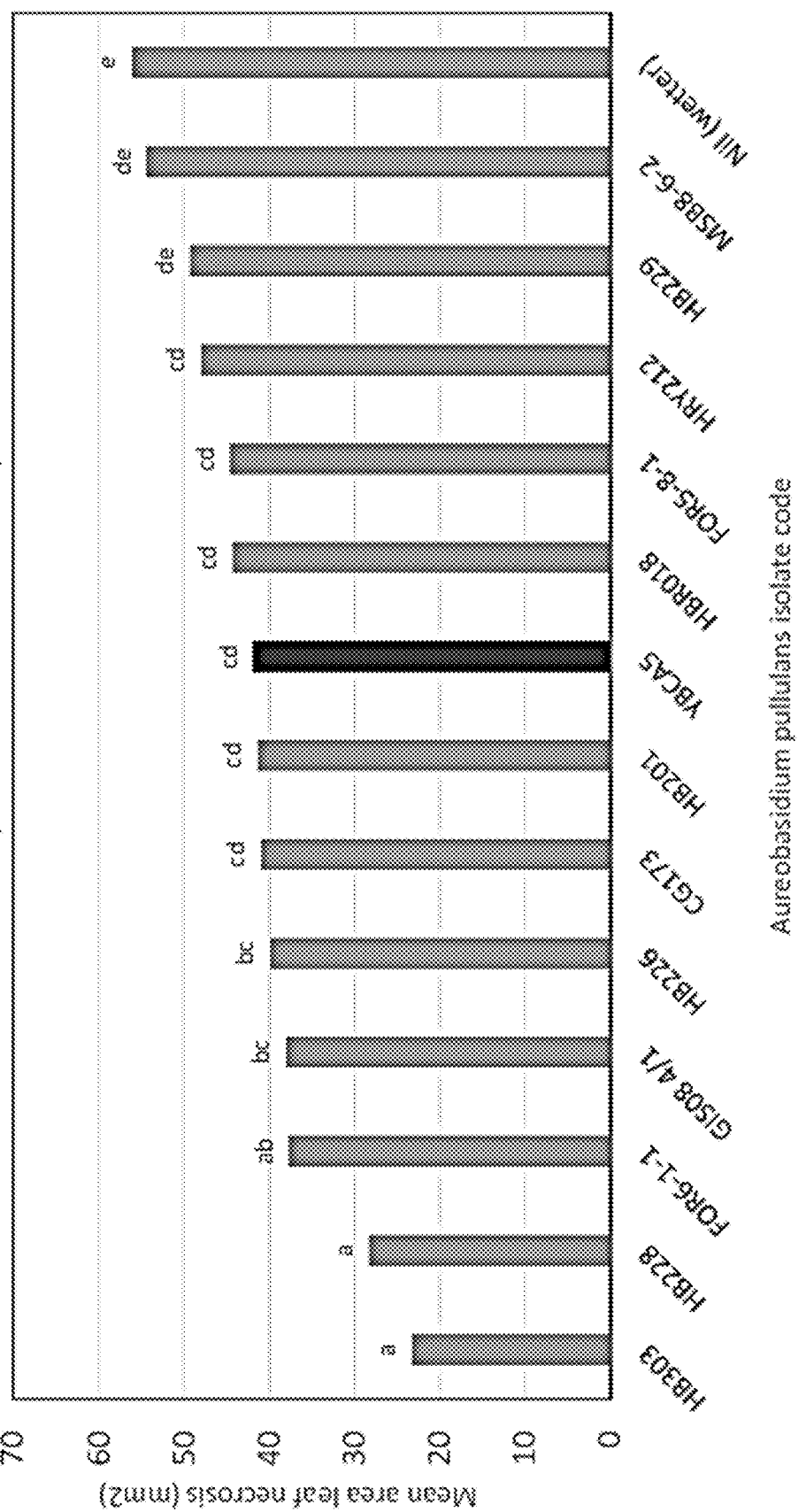
FIG. 2. The effect of different isolates of *Aureobasidium pullulans* on the severity of Psa leaf spot lesions on potted kiwifruit plants ('Hayward') compared to the untreated (Nil) in April 2016.

In the Nil (wetter only) treatment, the average Psa lesion area was 57 $mm^2$ (FIG. 2). One isolate (MSB8-6-2) did not significantly reduce ($P>0.05$) Psa severity (lesion size=54 $mm^2$) compared to the Nil control. YBCA5 significantly reduced Psa lesion area to 43 mm2 (efficacy=25%). This assay demonstrated that not all *Aureobasidium pullulans* isolates have the ability to significantly reduce Psa severity on potted kiwifruit plants and efficacy against Psa is dependent upon the isolate selected.

Zespri Assay 31

The aim of this assay was to compare the efficacy of YBCA5 applied alone and integrated with copper or Actigard for control of Psa on potted plants exposed to natural Psa inoculum in a research orchard.

Plant Material

This assay was carried out in the shadehouse structure (Block 20) at Te Puke Research Orchard. The plants were originally grown at the Ruakura glasshouse using tissue cultured *A. chinensis* var. *deliciosa* 'Hayward' plants grown in 1.5 L pots. Once the plants were 25 cm in height they were re-potted onto 2.5 L pots and moved to the Ruakura shade house and connected up to dripper irrigation on 30 Oct. 2015. At the time of treatment on 3 Nov. 2015, each plant had at least 4 useable leaves per plant and there were 15 replicate plants per treatment. Treatments and foliar spray dates are described in Table 2.

TABLE 2

Treatment schedule for potted 'Hayward' plants exposed to natural Psa inoculum at the Te Puke Research Orchard.

| TRT No. | $1^{st}$ Foliar treatment | $2^{st}$ Foliar Treatment (+10 d) | $3^{rd}$ Foliar Treatment (+10 d) | $4^{th}$ Foliar Treatment (+10 d) | Rationale |
|---|---|---|---|---|---|
| Site | Ruakura | TPRO | TPRO | TPRO | |
| Spray date | Nov. 3, 2015 | Nov. 13, 2015 | Nov. 23, 2015 | Dec. 3, 2015 | |
| 1. | Nu-Film* | Nu-Film | Nu-Film | Nu-Film | Wetter control |
| 2. | Kocide** | Kocide | Kocide | Kocide | Copper based std |
| 3. | YBCA5 | YBCA5 | YBCA5 | YBCA5 | YBCA5 |
| 4. | Kocide | YBCA5 | Kocide | YBCA5 | Integrated programme I |
| 5. | Actigard | YBCA5 | Actigard | YBCA5 | Integrated programme II |

*Miller Chemical & Fertilizer Corporation, USA
**DuPont USA

Yeast Preparation

YBCA5 granules were prepared by fermenting the yeast for 3 days in a 10 L bioreactor (Labfors) using sterile liquid media (4% molasses and 1.2 g/L urea). The fermentate was spun in a centrifuge (Sorvall RC-5C) at 5000 rpm for 15 min (rotor no. SLC-4000, rotorcode 33) to achieve a wet pellet of cell concentrate after discarding the supernatant. This wet pellet was mixed with approximately 30% (w/w) cornstarch to form a stiff dough consistency and this was extruded through a steel mesh (3 mm hole size) and dried in a laminar flow hood overnight (20-25° C.) to form dried granules.

All YBCA5 treatments were applied at a final concentration of $2\times10^7$ CFU/mL and plants were allowed to dry. The final volume that was prepared ranged from 500 mL to one litre depending on the size of the plants being treated.

Psa Inoculum Preparation

The aim of this project was to expose potted plants to Psa inoculum in at the Te Puke Research Orchard (Block 20). This block was surrounded by mature kiwifruit vines with a history of Psa and this provided the inoculum over the period of time for this assay.

Leaf Sprays

The first spray treatments were applied at Ruakura on 3 Nov. 2016 and at 10-14 day intervals thereafter. (Details are described in Table 2 above). All treatments were applied to just prior to run-off with a hand held pump sprayer. Copper hydroxide (Kocide Opti) as applied at 0.7 g/L and Actigard was applied at 0.1 g/L. YBCA5 was applied with the wetter/sticker adjuvant, Nu-Film (250 ul per 500 ml).

Disease assessments were carried out on 17 Dec. 2015 by estimating the percentage area of leaf necrosis on all treated leaves.

Results—Assay Zespri 31

Figure 3:
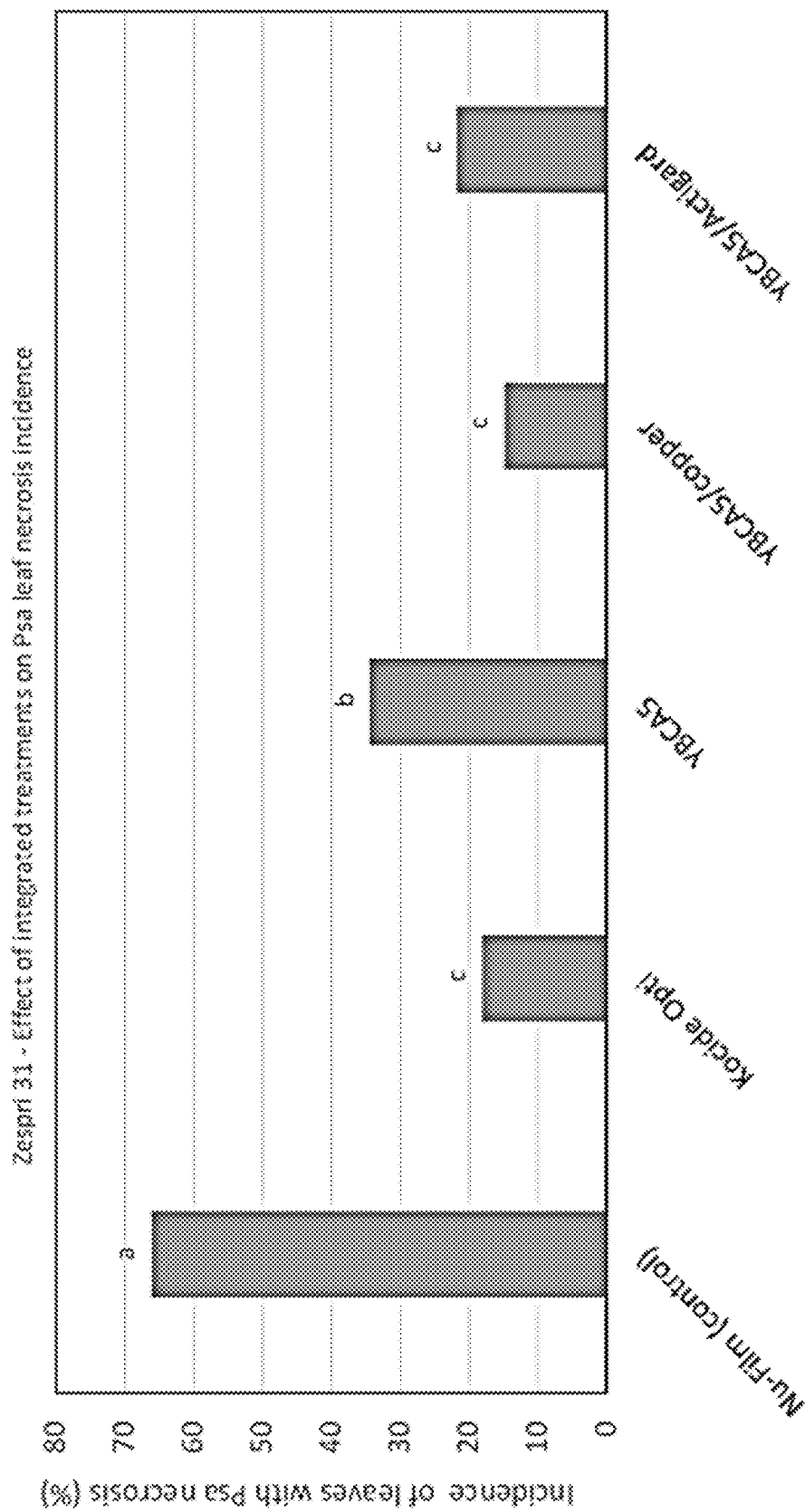
FIG. 3. Incidence of leaves with Psa necrosis on potted 'Hayward' plants exposed to natural Psa inoculum at Te Puke Research Orchard and with treatment applied on four occasions over a 30 day period. Leaf necrosis assessment was carried out 44 days after the first treatment application.
Figure 4:
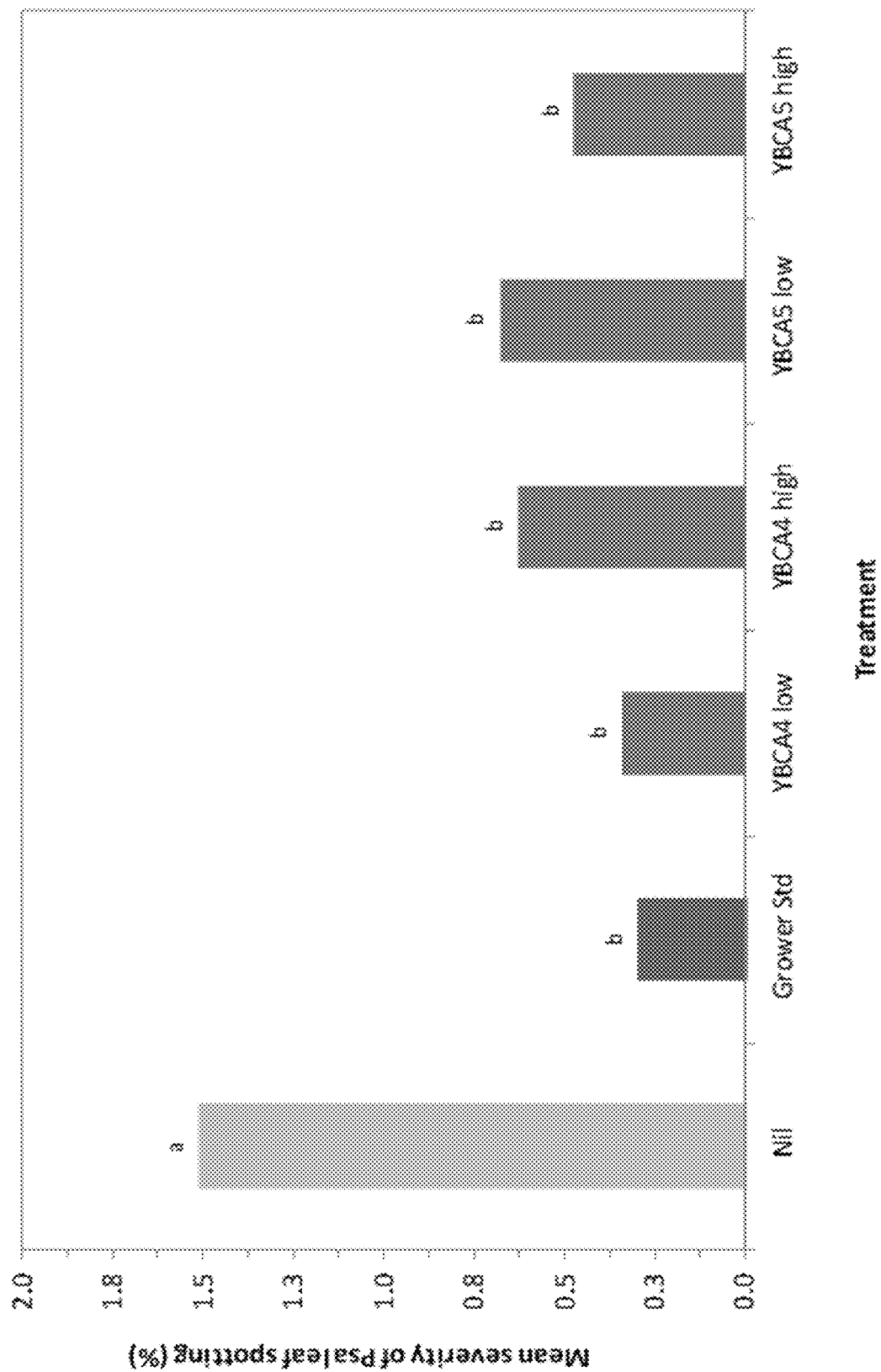
FIG. 4. Field testing the efficacy of YBCA5. Nil is observed incidence of leaf spotting on untreated control plants. Grower Std is the observed incidence of Psa leaf spotting on plants treated with Actigard and copper. Low and high refer to the amount of YBCA4 and YBCA5 respectively that was applied to the plants. Field site was Maketu. The kiwifruit variety was 'Hayward'. All treatments were applied between bud burst and pre-flowering. A total of 5 spray treatments were carried out between 6 and 12 days apart. For each of FIGS. 4-8, High rate is $2 \times 10^7$ cells/mL and low rate is $1 \times 10^7$.
Figure 5:
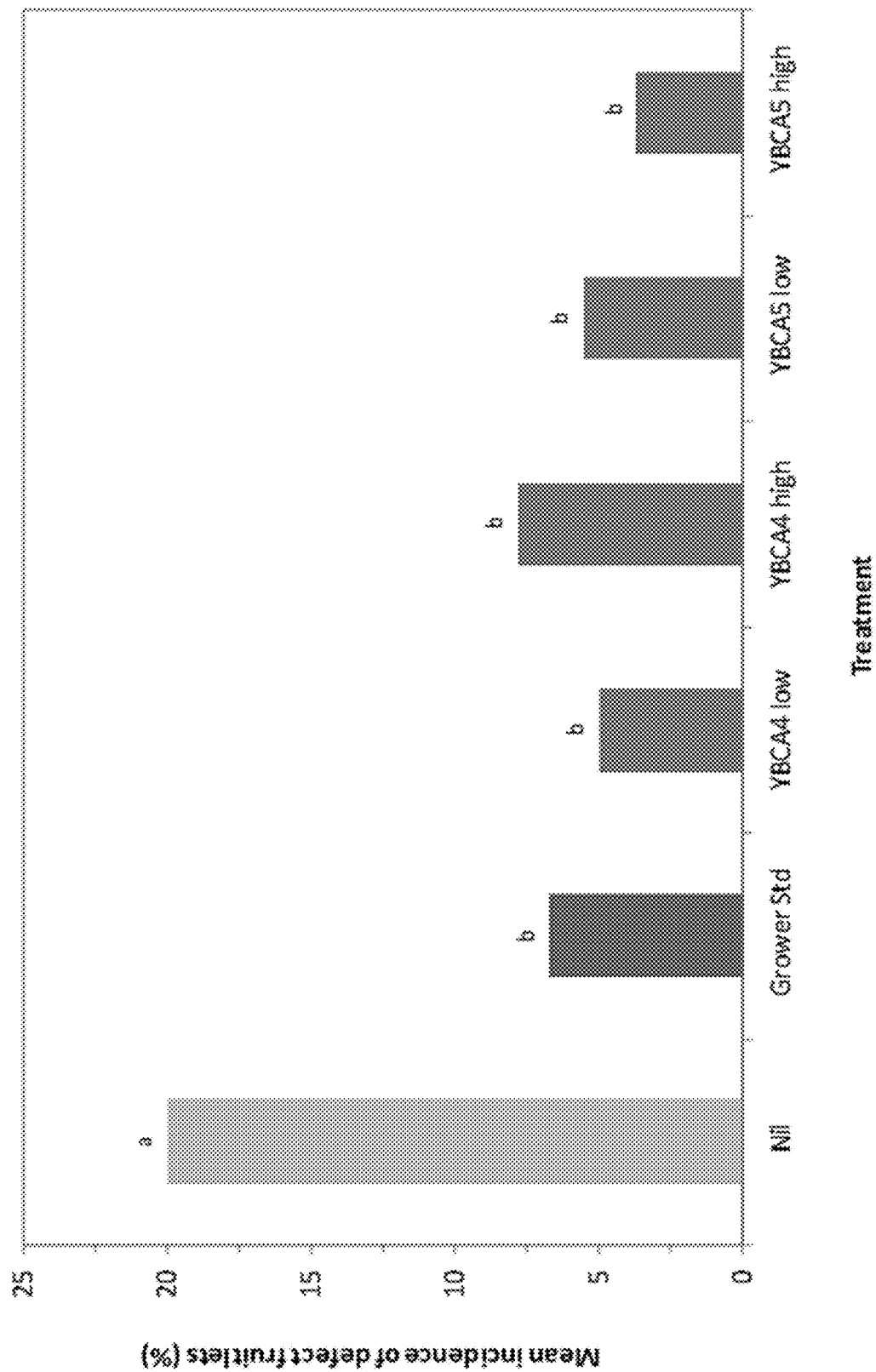
FIG. 5. Field testing the efficacy of YBCA5. Nil is observed incidence of defects on untreated control plants. Grower Std is the observed incidence of Psa leaf spotting on plants treated with Actigard and copper. Low and high refer to the amount of YBCA4 and YBCA5 respectively that applied to the plants. Field site was Maketu. The kiwifruit variety was 'Hayward'. All treatments were applied between bud burst and pre-flowering. A total of 5 spray treatments were carried out between 6 and 12 days apart.
Figure 6:
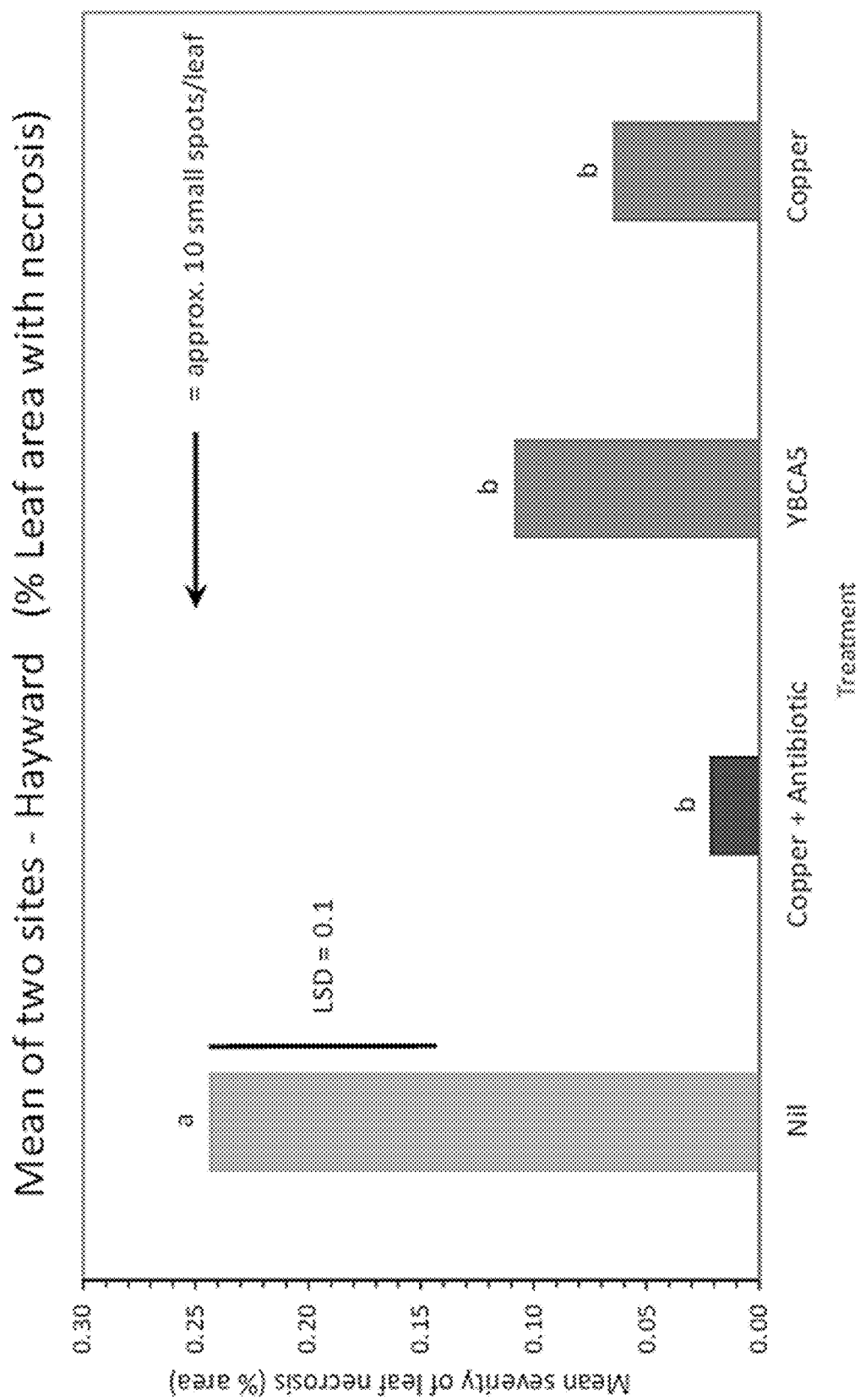
FIG. 6. Field testing the efficacy of YBCA5 showing the mean severity of leaf necrosis. Kiwifruit variety was 'Hayward'. Grower std. is copper+antibiotic. Treatments were applied from bud burst to first flowering at two sites in Maketu. 6 treatments (sprays) were applied in total, each 7-14 days apart.
Figure 7:
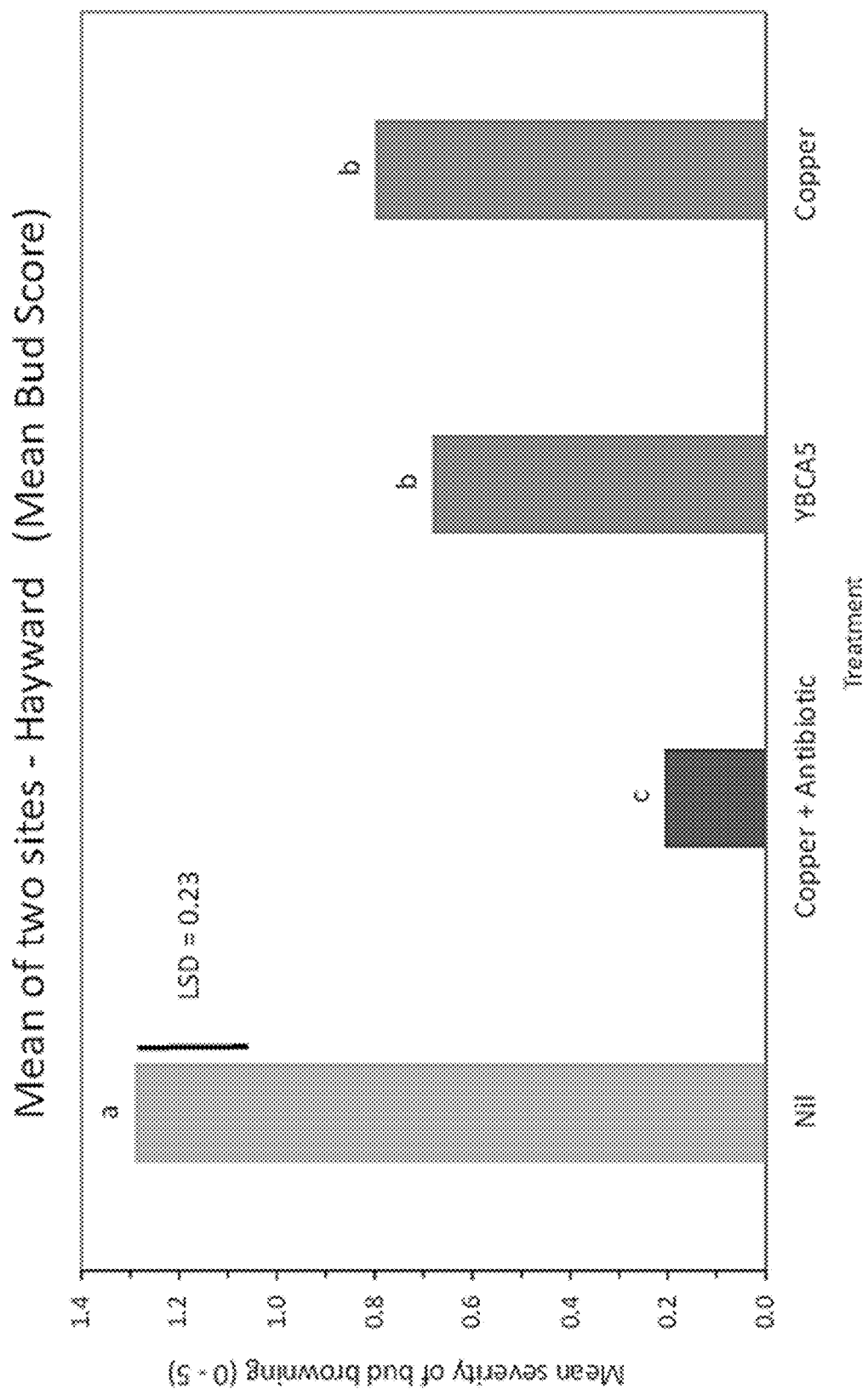
FIG. 7. Field testing the efficacy of YBCA5 showing the mean severity of bud browning. Kiwifruit variety was 'Hayward'. Grower std. is copper+antibiotic. Treatments were applied from bud burst to first flowering at two sites in Maketu. 6 treatments (sprays) were applied in total, each 7-14 days apart.
Figure 8:
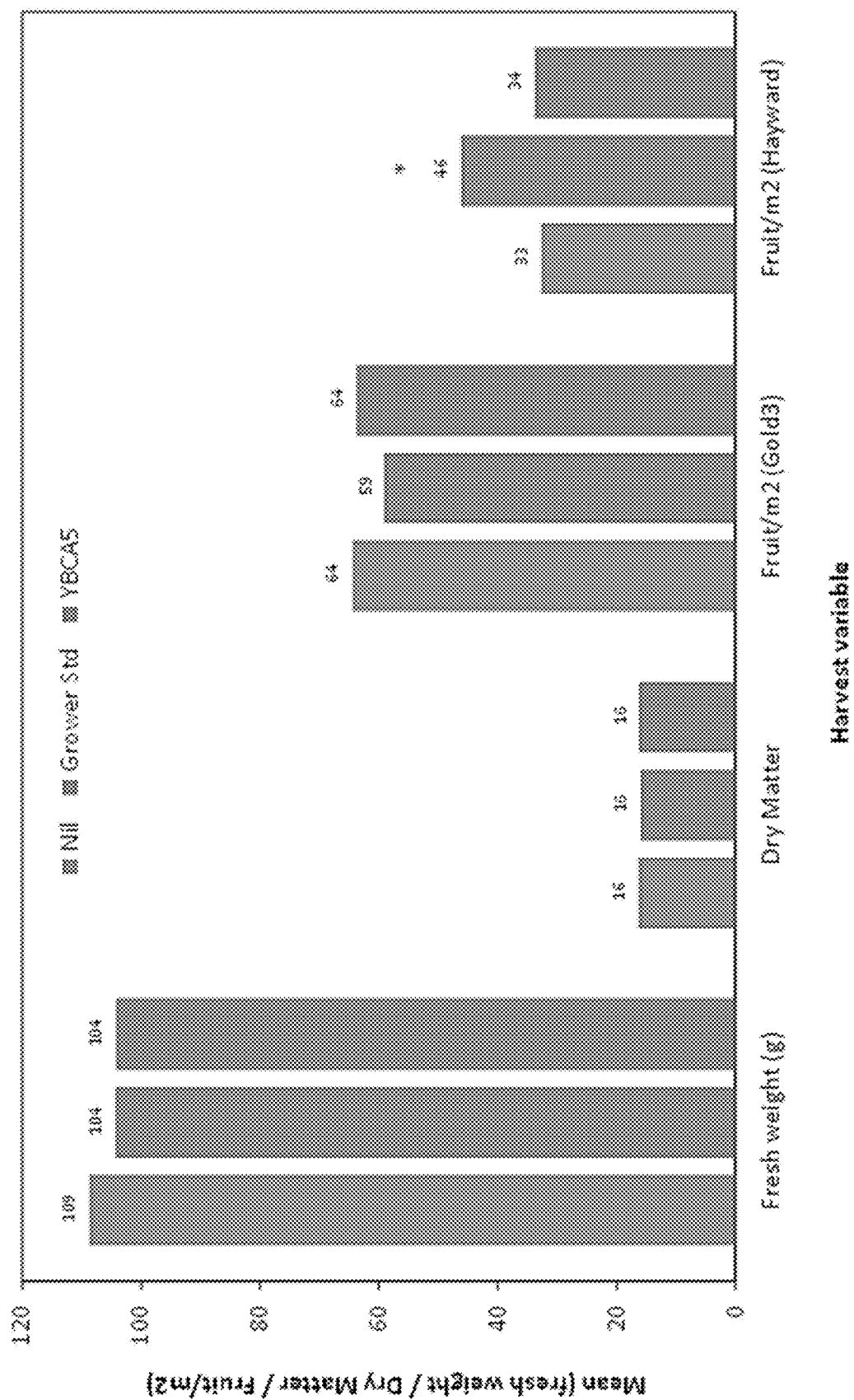
FIG. 8. Field testing the efficacy of YBCA5 showing the mean increase in yield (fresh weight/dry matter/fruit/m$^2$. Kiwifruit variety was 'Hayward'. Grower std. is copper+antibiotic. Treatments were applied from bud burst to first flowering, once during flowering and once post fruit set. 7 treatments (sprays) were applied in total, each 7-14 days apart. In each category: fresh weight, dry matter, fruit/m$^2$ (Gold3) and fruit/m$^2$ ('Hayward') the bars on the graph from left to right depict nil treatment, grower standard treatment (copper and antibiotic) and YBCA5.

In the absence of any treatment (Nu-film only, control), Psa leaf spot incidence was 66% and this was significantly reduced by Kocide Opti (18%), YBCA5 (35%), YBCA5 and Kocide Opti (Integrated programme I) (15%), YBCA5 and Actigard (Integrated programme II) (22%) (FIG. 3).

This assay demonstrated that YBCA5 significantly reduced (P<0.05) the incidence of Psa leaf spotting on potted plants under a shaded structure when exposed to natural Psa inoculum. Although the level of disease control was not as effective as the Kocide Opti based programme, the assay demonstrated that YBCA5 could be successfully integrated with a copper based product and with Actigard with no significant loss of efficacy compared with the copper only treatment.

Example 3—Yeast Biocontrol of Phytopathogenic Fungi

YBCA5 Biocontrol of *Monilinia fructicola* and *Botrytis* Spp.

Methods

Fruit-based screening assays were conducted in laboratories at the Plant and Food Research Ruakura Research Centre, Hamilton, New Zealand (PFR). PFR assays focused on dip treatment application of YBCA5 and fungicide controls.

Fruit Material (Assays 1 to 4)

Fruit for *Monilinia fructicola* and *Botrytis* spp. inoculation assays were carried out on sweet cherries (*Prunus avium* 'Sweet Valentine') that were picked at the harvest mature stage and sourced from the PFR Clyde Research Orchard in Central Otago on 8 Jan. 2016 for fruit based assays 1 and 2. A second harvest was carried out on 13 Jan. 2016 for fruit based assays 3 and 4.

Each cherry was then subjected to a double wash process. Wash one consisted of 10 minutes in tap water on a rotary shaker (110 rpm) followed by a five minute wash in SDW (Wash 2). All cherries were placed onto sterile black plastic grids in a sterile plastic meat tray with two sterile paper towels and were allowed to dry in a laminar flow hood. Each cherry was dipped in the treatments for 60 seconds and again allowed to dry, as described above. 40 ml deionised water was added to the paper towels to ensure high relative humidity, and then enclosed in a plastic bag to incubate at 23° C. for 24 h (Assay 1) and 48 hours (Assay 2) to allow the YBCA5 treatment to become established on the fruit surface.

Assay 5 Fruit Material

Fruit assays were carried out on detached white table grape berries ('Thompson seedless'—Assay 5), imported from California that were sourced from a local supermarket in Hamilton. Each berry was detached from the bunch with 3-4 mm of pedicel remaining and then subjected to a double wash process. Wash one consisted of 10 minutes in tap water on a rotary shaker (110 rpm) followed by a five minute wash in SDW (Wash 2). All berries were placed onto sterile black plastic grids in a sterile plastic meat tray with two sterile paper towels and were allowed to dry in a laminar flow hood. Each berry was lightly wounded with the aid of fine sandpaper, Grade P220, then dipped in the treatments for 60 seconds and again allowed to dry.

YBCA5 Preparation (Assays 1 to 5)

YBCA5 granules were prepared by fermenting the yeast for 3 days in a 10 L bioreactor (Labfors) using sterile liquid media (4% molasses and 1.2 g/L urea). The fermentate was spun in a centrifuge (Sorvall RC-5C) at 5000 rpm for 15 min (rotor no. SLC-4000, rotorcode 33) to achieve a wet pellet of cell concentrate after discarding the supernatant. This wet pellet was mixed with approximately 30% (w/w) cornstarch to form a stiff dough consistency and this was extruded through a steel mesh (3 mm hole size) and dried in a laminar flow hood overnight (20-25° C.) to form dried granules.

The YBCA5 treatments were prepared from these water dispersible granules that had been stored at 5-7° C. in a refrigerator and a suspension prepared by adding 1 g per litre of deionised water (final concentration=$2 \times 10^7$ CFU/ml) and gently stirred to form a suspension. To ensure all cells were evenly dispersed and remained in suspension, a wetting agent (Nu-Film) was added at 0.5 ml per litre.

Fungicides (Assays 1 to 5)

For assays 1 and 2, a liquid suspension containing 500 g/L) was prepared at the recommended field rate of 0.85 mL/L (an average of the recommended field rates of 0.75 mL/L for Monilinia in stonefruit and 1.0 mL/L for Botrytis in berryfruit). No wetting agent was used.

For assays 3 and 4, a liquid suspension of captan was prepared from Captan Flo (Nufarm NZ) (containing captan at 600 g/L) at the recommended field rate for use in stone fruit of 160 mL/litre. No wetter was used.

Monilinia Inoculum Preparation (Assays 1 and 3)

A Monilinia fructicola culture (isolate code MFGQ3), which had been originally isolated from an infected peach tree located in the Hamilton region during 1998, was used for the spray inoculation assays included in this section (Ruakura based assay). Monilinia inoculum was prepared by growing this strain of Monilinia for 7 days on PDA (Difco, Fort Richard) medium and harvesting the conidia by washing the plate with SDW plus Tween 80 (0.05%) to make a stock suspension of inoculum. This stock suspension was then filtered using a 70 µm cell strainer (to remove mycelial fragments), the concentration determined using a haemocytometer and then adjusted, by dilution with SDW+Tw 80 (0.05%) to a final concentration of $1 \times 10^4$ conidia/mL.

Botrytis Spp. Inoculum Preparation (Assay 2 and 4)

A Botrytis spp. culture (isolate code 09-2), which had been originally isolated from an infected kiwifruit located in the Bay of Plenty region during the 2000s, was used for the spray inoculation assays included in this section carried out on cherries. Botrytis spp. inoculum was prepared by growing this strain of Botrytis spp. for 5-7 days on PDA (DIFCO, Fort Richard) medium and harvesting the conidia by washing the plate with SDW plus Tween 80 (0.05%) to make a stock suspension of inoculum. This stock suspension was then filtered using a 70 µm cell strainer (70 µm mesh) to remove mycelial fragments, the concentration determined using a haemocytometer and then adjusted, by dilution with SDW+Tw 80 (0.01% v/v) to a final concentration of $1 \times 10^5$ conidia/mL.

Botrytis Inoculum Preparation (Assay 5)

Two Botrytis spp. cultures (isolate codes 189 and 547), which had been originally isolated from infected tomatoes, Auckland region during 2010, were used for the droplet inoculation assays included in this assay. One isolate was sensitive to two commonly used fungicides (dicarboximide and carbendazim) and the other isolate was resistance to each of these same fungicides.

Botrytis spp. inoculum was prepared by growing each isolate of Botrytis spp. for 5-7 days on PDA (DIFCO, Fort Richard) medium and harvesting the conidia by washing the plate with SDW plus Tween 80 (0.01%) to make a stock suspension of inoculum. This stock suspension was then filtered using a cell strainer (70 µm mesh, Falcon) to remove mycelial fragments, the concentration determined using a haemocytometer and adjusted to the required concentration ($2 \times 10^4$ conidia/mL) equivalent to 200 conidia in each 10 µL droplet. To ensure the conidial suspension remained on the wounded berry surface, paraffin 'wax bunds' were created around the wound surface by smearing a 1-2 mm thick layer of paraffin wax onto a glass slide lightly dabbing the base of a 1 mL pipette tip onto the paraffin wax layer and then transferring this 'paraffin wax ring' onto the wound surface. This effectively created a 5-6 mm diameter ring of paraffin wax ('bund') that retained the conidial suspension and prevented it from rolling off the rounded berry surface. Wounded and treated berries were then inoculated with 10 µL droplets of Botrytis spp. conidial suspension.

After pathogen inoculation, all inoculated fruit samples in a tray were enclosed in a plastic bag for 48 hours on the lab bench at 23° C. (Assays 1-4) or 21° C. (Assay 5). For all cherry and berry assays, two sterile paper towels were placed beneath the plastic grids, on which the berries lay, then moistened with 40 mL SDW and each tray was enclosed in a clean plastic bag and then sealed to maintain high relative humidity over the first 72 h. Thereafter, the bags were removed, folded over the trays (to ensure each end of the tray was open for adequate air flow), to allow the relative humidity to decline over a 15-h period (5 µm in the late afternoon to 8 am the next morning) after which, they were resealed. This process of alternating the relative humidity within the incubation chambers was repeated over the duration of the experiment and is a method that has been shown to avoid excessive mycelial growth. After 5 days incubation, fruit with typical Monilinia spp. or Botrytis spp. symptoms were recorded and removed from each replicate tray. Rots were recorded daily and the incidence (%) of cumulative Monilinia spp. or Botrytis spp. rots, after 13 days (Assay 1 and 2), 16 days (Assay 3 and 4) and 9 days (Assay 5). In assay 5, the severity of Botrytis spp. infection was determined for each treatment by visually scoring the proportion of the berry surface covered in Botrytis spp. conidiophores.

YBCA5 Biocontrol of Colletotrichum Spp. and Penicillium Spp. in Apples

Apple Assays 6 and 7

Apple fruit ('Pacific Rose') were sourced from an organic orchard in Hawkes Bay and were washed in running tap water in a 10 L bucket. Apples were then dried in a biohazard hood for approximately 1.5 h, turning them after 45 min and then wiped with a tissue soaked in ethanol and allowed to dry once more. Apples were then placed onto moistened paper towels lining the bottom of plastic clam shell containers, two apples per container. There were 10 replicate apples for each treatment in assays 6 and 7.

There were five treatments: a Nil control (0.05% Tween80), Fungicide (0.5 mL/L of Prolific (containing 500 g/L carbendazim)), YBCA5 applied at $1 \times 10^7$ CFU/mL 24 hours prior to the pathogen, YBCA5 applied at $1 \times 10^7$ CFU/mL 2 hours prior to the pathogen and pathogen only (Colletotrichum spp. for assay 6 and Penicillium spp. for assay 7). YBCA5 granules were prepared by fermenting the yeast for 3 days in a 10 L bioreactor (Labfors) using sterile liquid media (4% molasses and 1.2 g/L urea). The fermentate was spun in a centrifuge (Sorvall RC-5C) at 5000 rpm for 15 min (rotor no. SLC-4000, rotorcode 33) to achieve a wet pellet of cell concentrate after discarding the supernatant. This wet pellet was mixed with approximately 30% (w/w) corn-starch to form a stiff dough consistency and this was extruded through a steel mesh (3 mm hole size) and dried in a laminar flow hood overnight (20-25° C.) to form dried granules.

The YBCA5 treatments were prepared from these water dispersible granules that had been stored at 5-7° C. in a refrigerator and a suspension prepared by adding 0.5 g per litre of deionised water (final concentration=$1\times10^7$ CFU/mL) and gently stirred to form a suspension.

The pathogen spore suspensions were prepared from cultures of *Colletotrichum* spp. and *Penicillium* spp. grown on PDA. One third of the culture was removed from the PDA Petri dish and transferred into a 50 mL Falcon tube containing 30 mL of SDW (with 0.05% Tween80). This was shaken vigorously for 1 min to dislodge spores into the suspension and then passed through a 70µ cell strainer to remove any mycelial fragments. The spore concentration was calculated using the aid of a haemocytometer and dilutions made to achieve a final concentration of $1\times10^5$ spores/mL On the day the apples were washed and prepared (day 1), a small wound (3 mm diameter×2-3 mm deep) were made in the side of each apple and numbered as treatment 3. A 10 µL aliquot of YBCA5 suspension was added to the wound, enough to fill the wound. On the following day (day 2) four more wounds were made and numbered as treatments 1, 2, 4 and 5. Treatments 1, 2 and 4 were applied to the wounds by adding 10 µL aliquots of each solution to the respective wounds. Two hours later the pathogen was applied by adding 10 µL aliquots of *Colletotrichum* spp. to each wound (treatments 2, 3, 4 and 5) for assay 6 and adding 10 µL aliquots of *Penicillium* spp. to each wound (treatments 2, 3, 4 and 5) for assay 7. Thirty mL of additional SDW was added to the paper towel in each clam shell container to maintain relative humidity and the containers were incubated in a Sanyo incubator at 23° C. for 1-2 weeks to allow rots to develop.

The lesion diameter of rots were measured using digital callipers after 8 days. Lesion size was corrected for the diameter of the wound by subtracting 3 mm from each measurement and then ANOVA was carried out using Genstat to test for treatment differences based on least significant differences.

Experimental Design

The cherry assays (assays 1-4) consisted of 10 cherries per replicate and there were six replicates (assays 1 and 2) and eight replicates (assays 3 and 4) for each treatment in a randomised block layout.

The grape berry assay (assay 5) consisted of five berries per replicate and there were four replicates for each treatment in a randomised block layout.

Statistical Analysis

Data were analysed using GenStat, 13th edition, with a randomised block experimental design and analysis of variance. Average fruit infection (% incidence) were log-transformed to equalise the variance to better meet the normality assumptions of the analysis. Raw data means and Least Significant Differences (LSDs) are presented, however all statistical comparisons are based on the log analysis.

Results of Cherry Inoculation Assays

Assay 1

Figure 9:
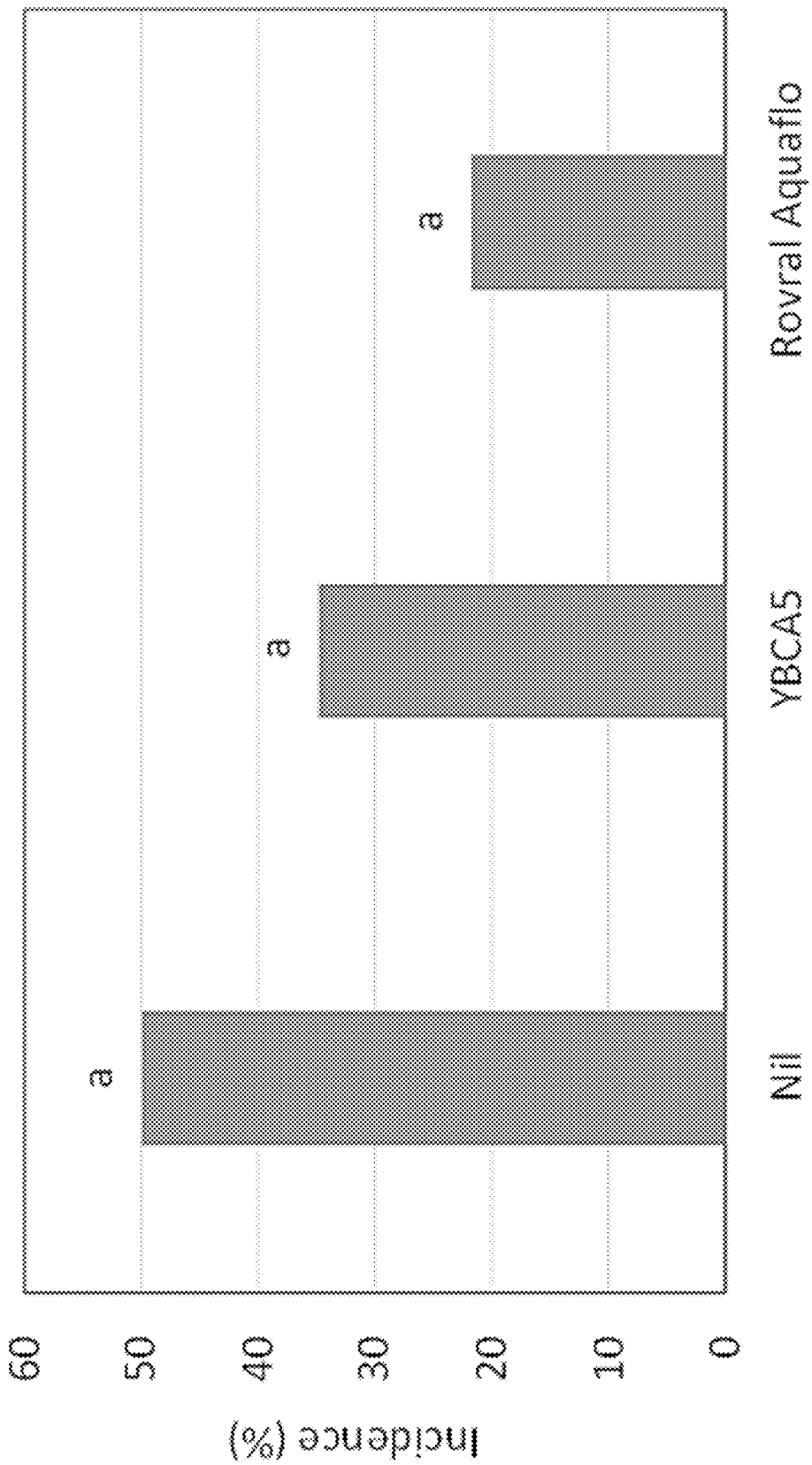
FIG. 9. The effect of YBCA5 on the incidence of *Monilinia* fruit rot of cherries ('Sweet Valentine') compared to the fungicide iprodione (Rovral® Aquaflo) in a lab based assay (Assay 1) in January-February 2016.

FIG. 9 summarises the effect of YBCA5 against *Monilinia* fruit rot in cherries. The incidence of *Monilinia* fruit rot in the Nil treatment was 50% and although the YBCA5 (34%) and iprodione treatments (22%) had a lower incidence of *Monilinia*, these were not significant reductions compared with the Nil treatment (FIG. 9).

Assay 2

Figure 10:
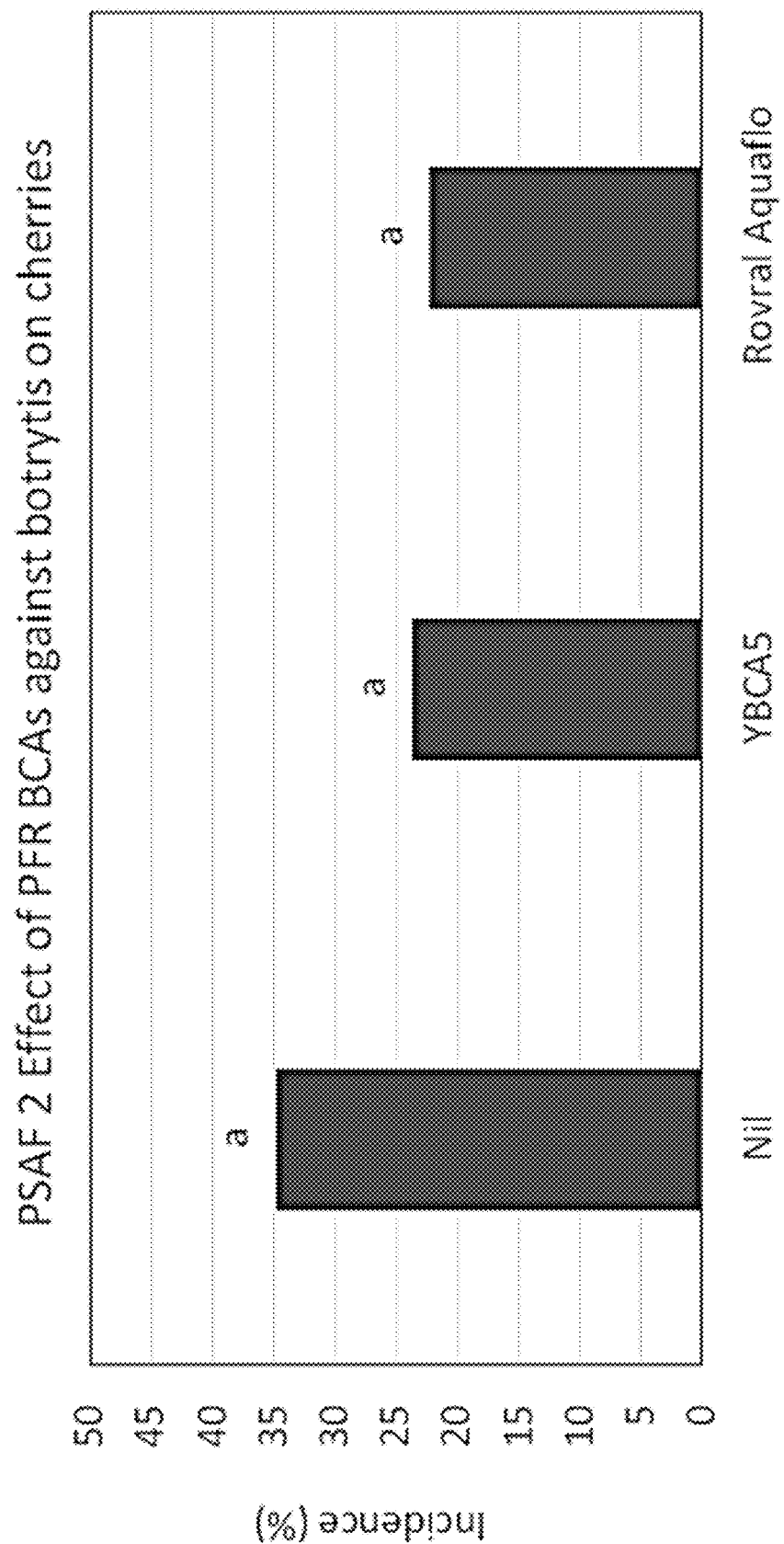
FIG. 10. The effect of YBCA5 on the incidence of *Botrytis* spp. fruit rot of cherries ('Sweet Valentine') compared to the fungicide iprodione in a lab based assay (Assay 2) in January-February 2016.

FIG. 10 summarises the effect of YBCA5 against *Botrytis* spp. fruit rot in cherries. The incidence of *Botrytis* spp. fruit rot in the nil treatment was 35% and this was not significantly (P>0.05) reduced in the YBCA5 (24%) and iprodione treatment (22%) (FIG. 10).

Assay 3

Figure 11:
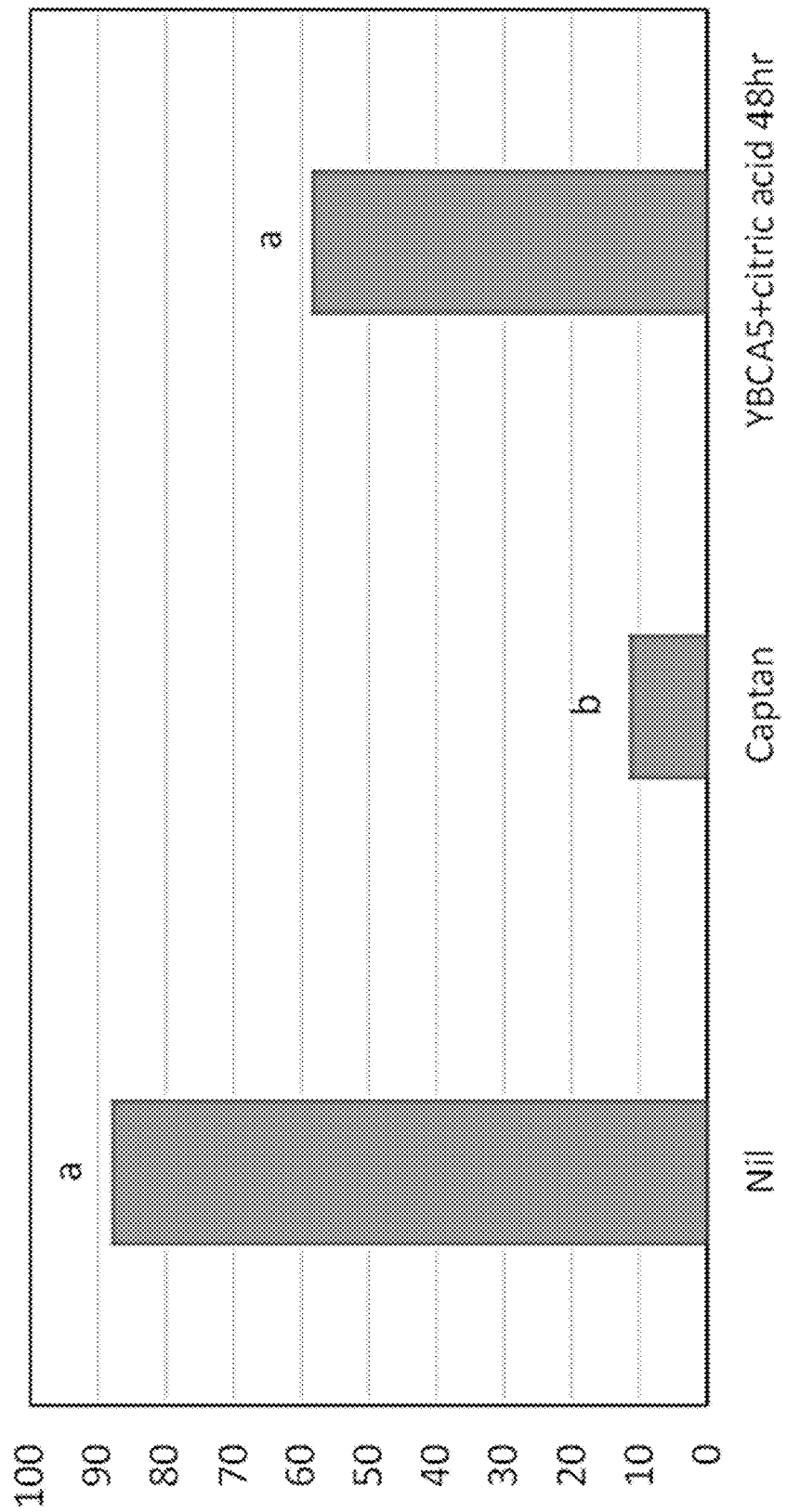
FIG. 11. The effect of YBCA5 on the incidence of *Monilinia* fruit rot of cherries ('Sweet Valentine') compared to the fungicide captan in a lab based assay (Assay 3) in February-March 2016.

FIG. 11 summarises the effect of YBCA5 against *Monilinia* fruit rot in cherries in another assay (Assay 3). The incidence of *Monilinia* fruit rot in the nil treatment was 88% and this was not significantly (P>0.05) reduced by the YBCA5 (59%). The captan fungicide treatment (12%) significantly reduced (P<0.001) the incidence of *Monilinia* fruit rot compared with the Nil treatment (FIG. 11).

Assay 4

Figure 12:
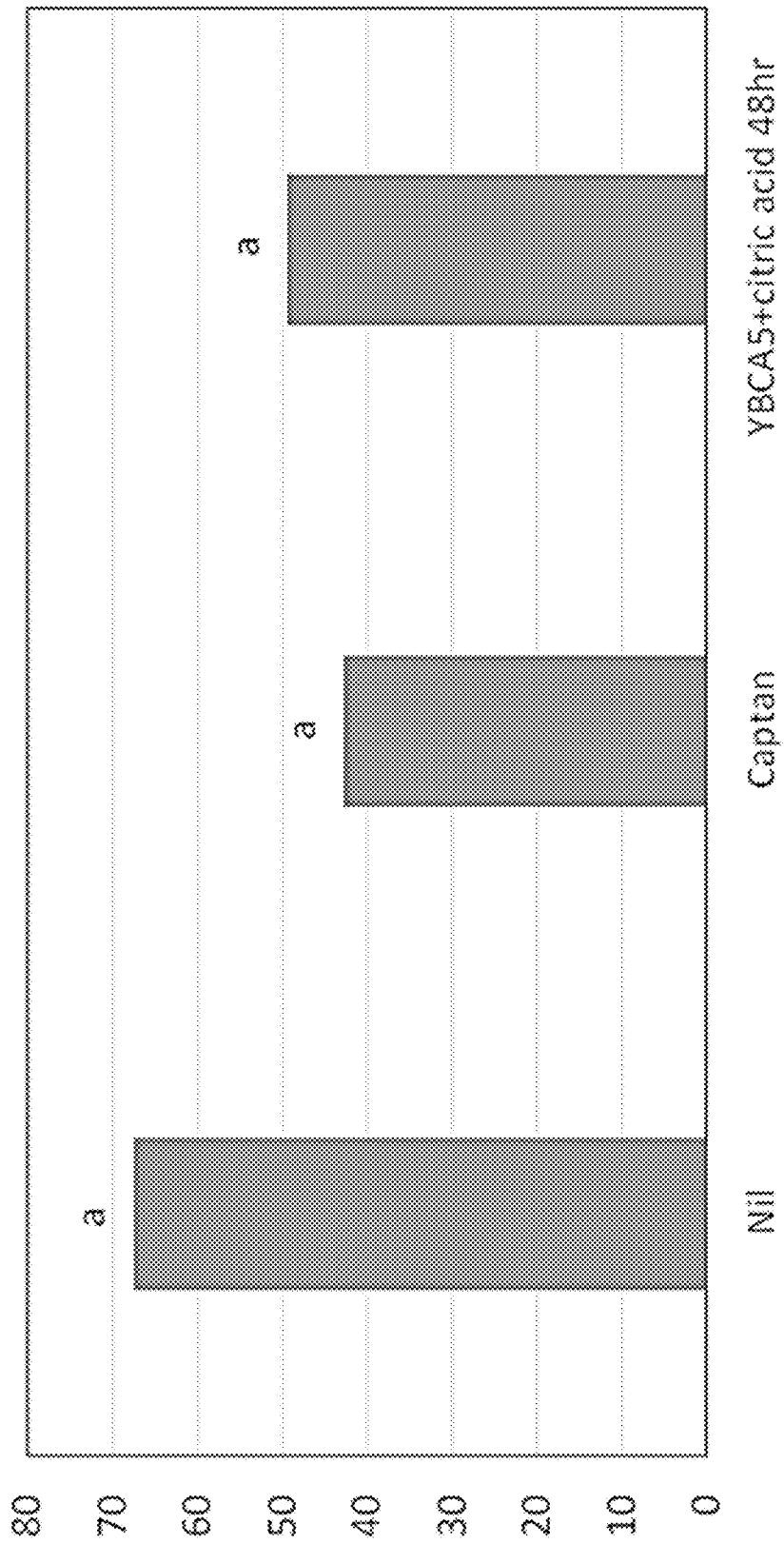
FIG. 12. The effect of YBCA5 on the incidence of *Botrytis* spp. fruit rot of cherries ('Sweet Valentine') compared to the fungicide captan in a lab based assay (Assay 2) in February-March 2016.

FIG. 12 summarises the effect of YBCA5 against *Botrytis* spp. fruit rot in cherries in another assay. The incidence of *Botrytis* spp. fruit rot in the nil treatment was 67% and this was not significantly reduced (P>0.05) in the YBCA5 (49%) and captan treatment (43%) (FIG. 12).

Results of Grape Inoculation Assay

Assay 5

Figure 13:
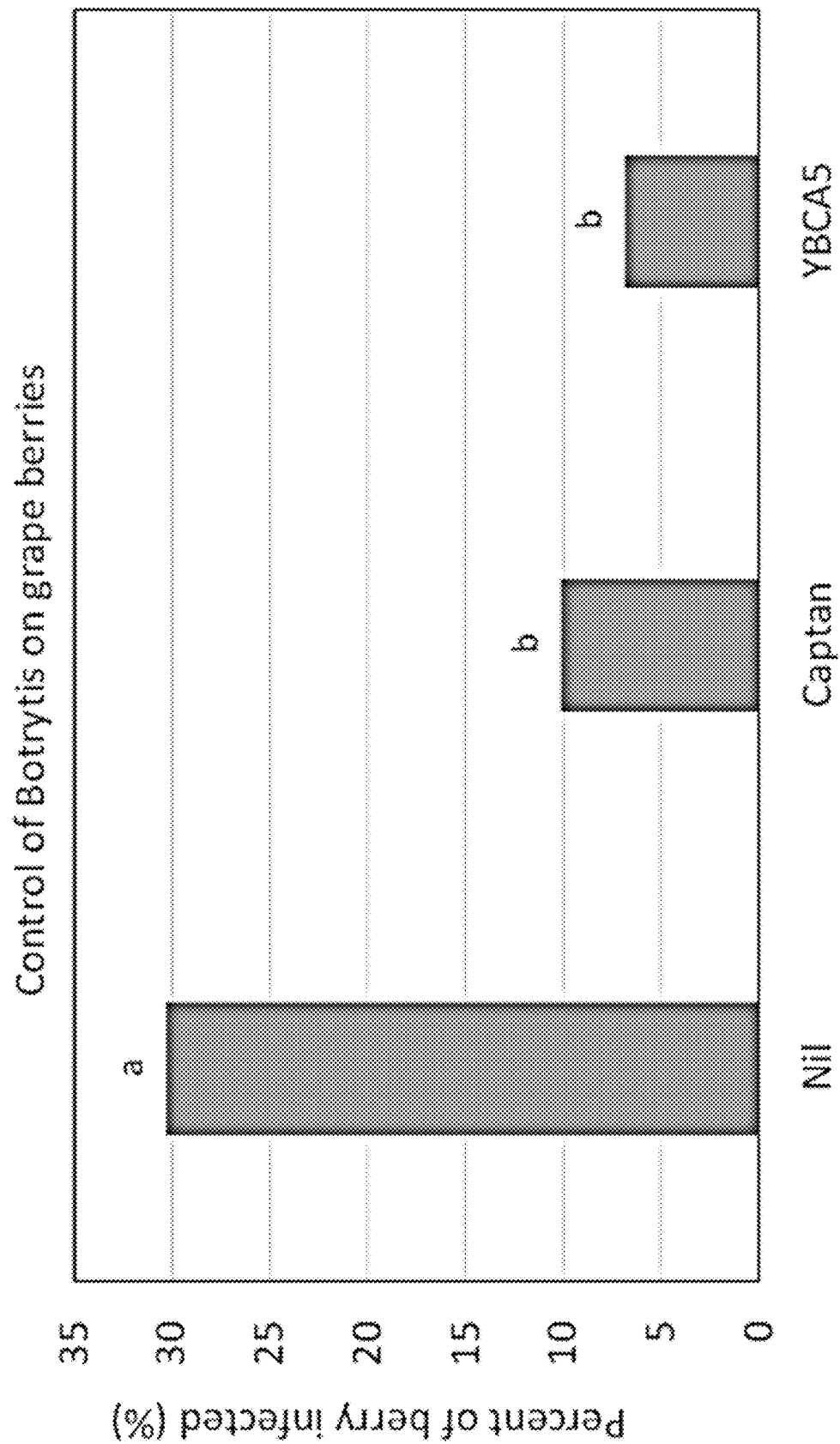
FIG. 13. The effect of YBCA5 on the severity of *Botrytis* spp. rot of table grapes ('Autumn King') compared to the fungicide captan in a lab based assay (Assay 5) in October-November 2015. Data is the mean of two *Botrytis* spp. isolates.

FIG. 13 summarises the effect of YBCA5 against *Botrytis* spp. fruit rot in table grapes in another assay (Assay 5). The incidence of *Botrytis* spp. fruit rot in the nil treatment 30% and this was significantly (P<0.001) reduced by the YBCA5 (7%) and captan treatment (10%) (FIG. 13).

Treatment of Other Diseases—Apple Results for Apple Assays 6 and 7

Assay 6

The mean lesion size in the untreated *Colletotrichum* control was 10.1 mm and this was significantly (P<0.05) reduced in the fungicide and both of the YBCA5 treatments (Table 3).

Applying YBCA5 24 hrs before the pathogen provided better protection than applying 2 hrs before the pathogen.

TABLE 3

Average lesion size on wounded apples ("Pacific Rose") treated with fungicide and YBCA5 prior to inoculation with *Colletotrichum* spp. spores ($1 \times 10^5$ spores/mL) and assessed after 8 days incubation at 23° C.

| Treatment | Average lesion (day 8) | Significance |
| --- | --- | --- |
| Nil (No Colletotrichum) | 0.3 | d |
| Fungicide (Prolific) | 1.1 | cd |

TABLE 3-continued

Average lesion size on wounded apples ("Pacific Rose") treated with fungicide and YBCA5 prior to inoculation with *Colletotrichum* spp. spores ($1 \times 10^5$ spores/mL) and assessed after 8 days incubation at 23° C.

| Treatment | Average lesion (day 8) | Significance |
|---|---|---|
| YBCA5 (24 hr) | 2.2 | c |
| YBCA5 (2 hr) | 5.7 | b |
| Nil + Colletotrichum | 10.1 | a |
| LSD (5%) | 1.42 | |
| P value | <0.001 | |

Treatment means followed by different letters show significant difference.

Assay 7:

The mean lesion size in the untreated *Penicillium* control was 15.2 mm and this was significantly (P<0.05) reduced in the fungicide and both of the YBCA5 treatments (Table 4). Similar to the previous assay, applying YBCA5 24 h before the pathogen provided significantly better protection than applying YBCA5 2 h before the pathogen.

TABLE 4

Average Lesion size on wounded apples ("Pacific Rose" treated with fungicide and YBCA5 prior to inoculation with *Penicillium* spp. spores ($1 \times 10^5$ spores/mL) and assessed after 8 days incubation at 23° C.

| Treatment | Average lesion | Significance |
|---|---|---|
| Nil (no *Penicillium*) | 0.3 | c |
| Fungicide (Prolific) | 0.4 | c |
| YBCA5 24 h | 0.4 | c |
| YBCA5 2 h | 3.8 | b |
| Nil + *Penicillium* | 15.2 | a |
| LSD (5%) | 3.51 | |
| P value | <0.001 | |

Treatment means followed by different letters show significant difference.

Assay 8: Post-Harvest Rot Due to Phytopathogenic Fungi on 'Hongyang' Kiwifruit

The most important export cultivar from China is 'Hongyang' and this red and yellow-fleshed cultivar is attacked by a range of postharvest pathogens including *Penicillium* spp. *Phomopsis* spp., *Alternaria* spp., *Colletotrichum* spp., *Cryptosporiopsis* spp. and *Botrytis* spp.

We investigated the efficacy of YBCA5 applied as a wound protectant against a range of postharvest fungal pathogens of fruits, particularly: *Penicillium* spp. *Phomopsis* spp., *Alternaria* spp., *Colletotrichum* spp., *Cryptosporiopsis* spp. and *Botrytis* spp.

Preliminary tests were carried out to establish the concentration of each pathogen that was required to rot the fruit after wounding in the absence of any treatment.

Methods

The kiwifruit 'Hongyang'-based screening assays (assays 8 and 9) were conducted in laboratories at the Plant and Food Research Ruakura Research Centre, Hamilton, New Zealand (PFR). PFR assays focused on wound application of YBCA5 treatment, a commercial biological control treatment and a fungicide were used as comparative controls.

Fruit Material (Assays 8)

The 'Hongyang' kiwifruit were sourced from the PFR Riwaka Research Orchard in Motueka on 12 Apr. 2017 for fruit based assays 8 and 9. *Penicillium* spp. *Phomopsis* spp., *Alternaria* spp., *Colletotrichum* spp., *Cryptosporiopsis* spp. and *Botrytis* spp. inoculation assays were carried out on 'Hongyang' kiwifruit that were picked at the harvest mature stage.

After removal from cool storage at 1° C., each fruit was subjected to a triple wash process. Wash one consisted of 30 seconds in 70% ethanol then a wash in tap water for 10 minutes on a rotary shaker (80 rpm—Wash 2) followed by a final wash for five minutes in SDW—Wash 3). All fruit were placed onto sterile black plastic grids in a sterile plastic meat tray with two sterile paper towels and were allowed to dry overnight in a laminar flow hood.

Just prior to wound treatment, each fruit was wounded on the side with a sterile stainless steel spike (4 mm deep×3 mm wide) and 10 μl of each treatment suspension was pipetted into the wound and allowed to dry.

Treatments and rates are detailed below

| Treatment | Recommended rate | gm or mL/Litre |
|---|---|---|
| YBCA5* | $1 \times 10^7$ | 0.5 g/L |
| Serenade Opti* | 125 g/100 L | 1.25 g/L |
| Rovral Aquaflo | 75 mL/100 L | 0.75 mL/L |

*YBCA5 and Serenade Opti prepared in Tween 80 (0.05%), Rovral Aquaflo was prepared in deionized water.

For assays 8 and 9, two sterile paper towels were placed beneath Plix cut-outs, moistened with 40 mL SDW and each fruit placed in disposable lunch boxes (Plix Extra Deep 45/45, containing five Plix fruit cut-outs to prevent fruit from moving), sealed, then placed into large (40 L) plastic bins which were closed to ensure high relative humidity for the first 24 h and incubated on the lab bench at 24° C. After 24 h, the Plix lunch boxes were removed from the bins and a 10 ul suspension of each fungal pathogen was pipetted into the treated wounds. All lunch boxes were resealed and placed back into the large plastic bins to ensure high relative humidity for the next 48 h. After this time, the Plix lunch boxes were removed from the large plastic bins, and a pin placed between the Plix box lid and base to allow some air to circulate and the relative humidity to decline over a 15 h period (5 µm in the late afternoon to 8 am the next morning) after which, they were resealed again. This process of alternating the relative humidity within the incubation chambers was repeated over the duration of the experiment and is a method that has been shown to avoid excessive mycelial growth. After 6 days, (*Alternaria* spp. *Botrytis* spp., *Penicillium* spp., *Phomopsis* spp., *Colletotrichum* spp.) and 7 days (*Cryptosporiopsis* spp.), the severity of fungal rot was assessed for each treatment by measuring the lesion length (mm) along the axis of the fruit. Data were expressed as the average lesion length, minus the initial width of the wound (3 mm).

YBCA5 Preparation (Assay 8 and 9)

YBCA5 granules were prepared by fermenting the yeast for 3 days in a 10 L bioreactor (Labfors) using sterile liquid media (4% molasses and 1.2 g/L urea). The fermentate was spun in a centrifuge (Sorvall RC-5C) at 5000 rpm for 15 min (rotor no. SLC-4000, rotorcode 33) to achieve a wet pellet of cell concentrate after discarding the supernatant. This wet pellet was mixed with approximately 30% (w/w) corn-starch to form a stiff dough consistency and this was extruded through a steel mesh (3 mm hole size) and dried in a laminar flow hood overnight (20-25° C.) to form dried granules.

The YBCA5 treatments were prepared from these water dispersible granules that had been stored at 5-7° C. in a refrigerator and a suspension prepared by adding 0.5 g per litre of deionised water (final concentration=$1\times10^7$ CFU/ml) and gently stirred to form a suspension.

Postharvest Pathogen Preparation

*Alternaria* Spp. Inoculum Preparation (Assay 8)

The *Alternaria* spp. culture (isolate code='*Alternaria* ex cherry'), which had been originally isolated from an infected cherry fruit from Central Otago during 2016, was used for the wound inoculation part of this assay. *Alternaria* spp. inoculum was prepared by growing this strain of *Alternaria* spp. for 21 days on Oat Meal Agar) medium and harvesting the conidia by washing the plate with SDW plus Tween 80 (0.05%) to make a stock suspension of inoculum. This stock suspension was then filtered using a 70 µm cell strainer (to remove mycelial fragments), the concentration determined using a haemocytometer and then adjusted, by dilution with SDW+Tw 80 (0.05%) to a final concentration of $2\times10^4$ conidia/mL.

*Botrytis* Spp. Inoculum Preparation (Assay 8)

A *Botrytis* spp. culture (isolate code 09-2), which had been originally isolated from an infected kiwifruit located in the Bay of Plenty region during the 2000s, was used for the spray inoculation assays included in this section carried out on cherries. *Botrytis* spp. inoculum was prepared by growing this strain of *Botrytis* spp. for 12 days on Oat Meal Agar medium and harvesting the conidia by washing the plate with SDW plus Tween 80 (0.05%) to make a stock suspension of inoculum. This stock suspension was then filtered using a 70 µm cell strainer (70 µm mesh) to remove mycelial fragments, the concentration determined using a haemocytometer and then adjusted, by dilution with SDW+Tw 80 (0.01% v/v) to a final concentration of $1\times10^5$ conidia/mL.

*Colletotrichum* Spp. Inoculum Preparation (Assay 8)

The *Colletotrichum* spp. culture (isolate code='ex G3'), which had been originally isolated from an infected Gold3 kiwifruit from the Ruakura research orchard during 2017, was used for the wound inoculation part of this assay. *Colletotrichum* spp. inoculum was prepared by growing this strain of *Colletotrichum* spp. for 21 days on PDA (Difco, Fort Richard) medium and harvesting the conidia by washing the plate with SDW plus Tween 80 (0.05%) to make a stock suspension of inoculum. This stock suspension was then filtered using a 70 µm cell strainer (to remove mycelial fragments), the concentration determined using a haemocytometer and then adjusted, by dilution with SDW+Tw 80 (0.05%) to a final concentration of $2\times10^4$ conidia/mL.

*Penicillium* Spp. Inoculum Preparation (Assay 8)

The *Penicillium* spp. culture (isolate code='*Penicillium* ex lemon'), which had been originally isolated from an infected lemon fruit from a supermarket in 2017, was used for the wound inoculation part of this assay. *Penicillium* spp. inoculum was prepared by growing this strain of *Penicillium* spp. for 12 days on PDA (Difco, Fort Richard) medium and harvesting the conidia by washing the plate with SDW plus Tween 80 (0.05%) to make a stock suspension of inoculum. This stock suspension was then filtered using a 70 µm cell strainer (to remove mycelial fragments), the concentration determined using a haemocytometer and then adjusted, by dilution with SDW+Tw 80 (0.05%) to a final concentration of $2\times10^4$ conidia/mL.

*Phomopsis* Spp. Inoculum Preparation (Assay 8)

The *Phomopsis* spp. culture (isolate code='*Phomopsis* ex G3'), which had been originally isolated from an infected Gold3 kiwifruit from the Ruakura research orchard during 2017, was used for the wound inoculation part of this assay. *Phomopsis* spp. inoculum was prepared by growing this strain of *Phomopsis* spp. for 21 days on PDA (Difco, Fort Richard) medium and harvesting the conidia by washing the plate with SDW plus Tween 80 (0.05%) to make a stock suspension of inoculum. This stock suspension was then filtered using a 70 µm cell strainer (to remove mycelial fragments), the concentration determined using a haemocytometer and then adjusted, by dilution with SDW+Tw 80 (0.05%) to a final concentration of $2\times10^4$ conidia/mL.

*Cryptosporiopsis* Spp. Inoculum Preparation (Assay 9 Only)

The *Cryptosporiopsis* spp. culture (isolate code='*Cryptosporiopsis* ex G3'), which had been originally isolated from an infected Gold3 kiwifruit from the Te Puke Research Orchard was used for the wound inoculation in assay 9. *Cryptosporiopsis* spp. inoculum was prepared by growing this strain of *Cryptosporiopsis* spp. for 28 days on PDA (Difco, Fort Richard) medium and harvesting the conidia by washing the plate with SDW plus Tween 80 (0.05%) to make a stock suspension of inoculum. This stock suspension was then filtered using a 70 µm cell strainer (to remove mycelial fragments), the concentration determined using a haemocytometer and then adjusted, by dilution with SDW+Tw 80 (0.05%) to a final concentration of $2\times10^4$ conidia/mL.

After pathogen inoculation in assay 8 and 9, all inoculated fruit samples were placed in disposable lunch boxes (Plix Extra Deep 45/45), containing five Plix fruit cut-outs to prevent fruit from moving), and 40 mL SDW added to two sterile paper towels that were placed beneath the Plix cut-outs, then placed into large (40 L) plastic bins which were closed to ensure high relative humidity for the first 48 h and incubated on the lab bench with natural and fluorescent light at 24° C. for up to three days. After 48 h, the Plix lunch boxes were removed from the bins and a pin placed between the lid and base to allow air to circulate and the relative humidity to decline over a 15 h period (5 µm in the late afternoon to 8 am the next morning) after which, they were resealed again. This process of alternating the relative humidity within the incubation chambers was repeated over the duration of the experiment and is a method that has been shown to avoid excessive mycelial growth. After 6 to 7 days the severity of fungal rot infection was assessed for each treatment by measuring the lesion length (mm) along the axis of the fruit. Data were expressed as the average lesion length, minus the initial width of the wound (3 mm).
Experimental Design The kiwifruit 'Hongyang' assay 8 consisted of 4 'Hongyang' kiwifruit per replicate and there were five replicates for each treatment in a randomised block layout. In total there were 22 treatments, including a Nil (no wound and no treatment) no pathogen inoculation) control, and a Nil (plus wound then SDW+Tw80) no pathogen inoculation control.
In Assay 9

The kiwifruit 'Hongyang' assay 9 consisted of 4 'Hongyang' kiwifruit per replicate and there were four replicates for each treatment in a randomised block layout. In total there were 5 treatments, including a Nil (no wound and no treatment) no pathogen inoculation control, and a Nil (plus wound then SDW+Tw80) no pathogen inoculation control.
Statistical Analysis Data were analysed using GenStat, 13th edition, with a randomised block experimental design and analysis of variance. Average lesion diameter did not require data transformation to equalise the variance and raw data means and Least Significant Differences (LSDs) are presented.
Results
Assay 8

YBCA5 treated fruit had significantly smaller lesions in 'Hongyang' fruit than the Rovral Aquaflo, Serenade Opti treatments and the untreated control when the fruit were inoculated with *Alternaria, Colletotrichum, Penicillium* and *Phomopsis*. YBCA5 treated fruit had lesions not significantly smaller than Rovral Aquaflo when the fruit were inoculated with *Botrytis* spp., but they were significantly smaller than the Serenade Opti treatment and untreated control.

Figure 14:
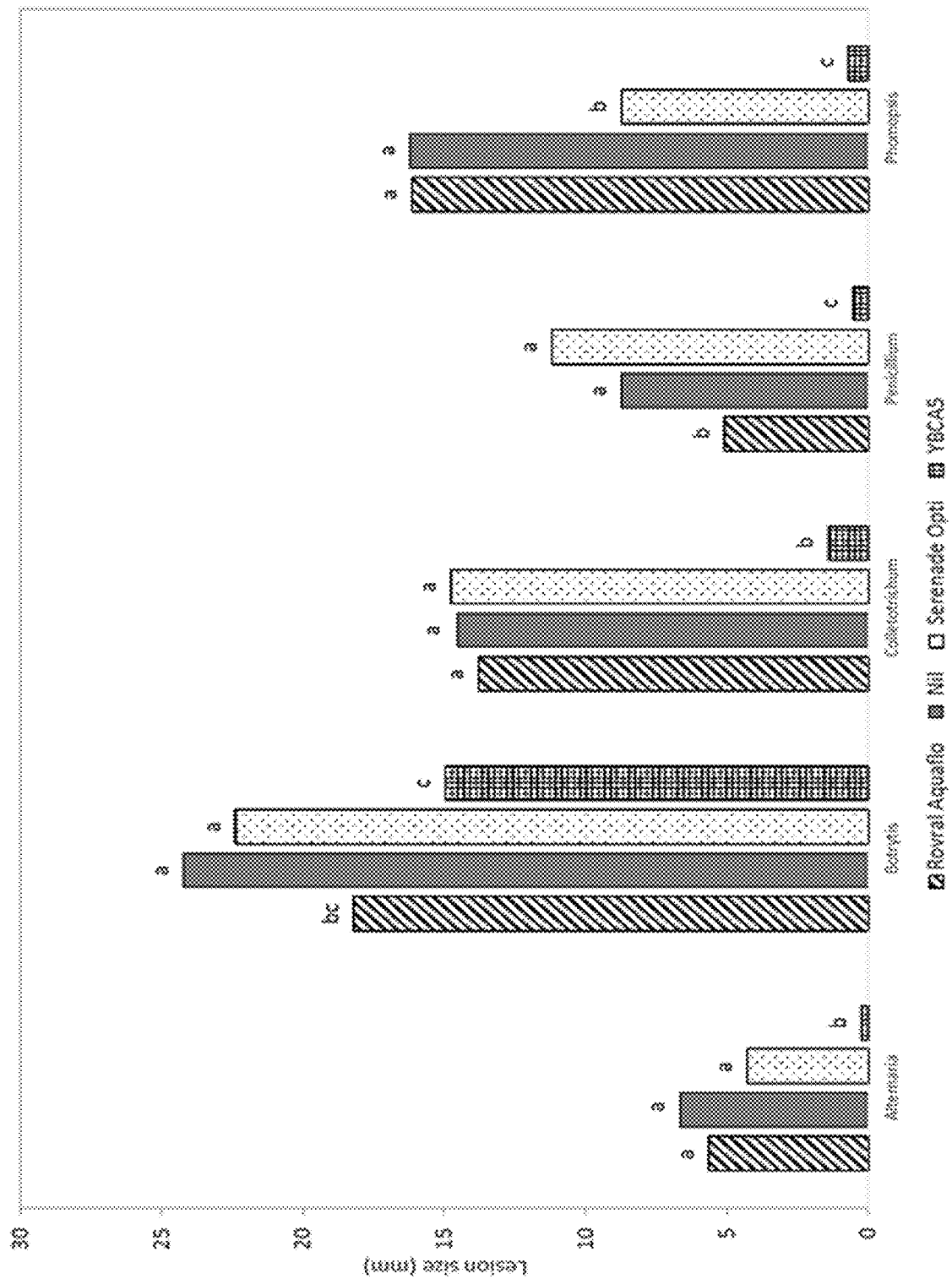
FIG. 14. The effect of YBCA5 on the severity of kiwifruit rot due to phytopathogenic fungal infection post-harvest. Lesion size (mm) of wounded 'Hongyang' kiwifruit after inoculation with *Alternaria* spp, *Botrytis* spp., *Colletotrichum* spp., *Penicillium* spp. or *Phomopsis* spp. and 6 days incubation. LSD (5%)=3.482, P fr=<0.001.

Rovral Aquaflo treated fruit had lesions significantly smaller than the untreated control when fruit were inoculated with *Botrytis* spp. and *Penicillium* spp. Serenade Opti treated fruit had lesions significantly smaller than the Untreated control when fruit were inoculated with *Phomopsis* (FIG. 14).

Figure 15:
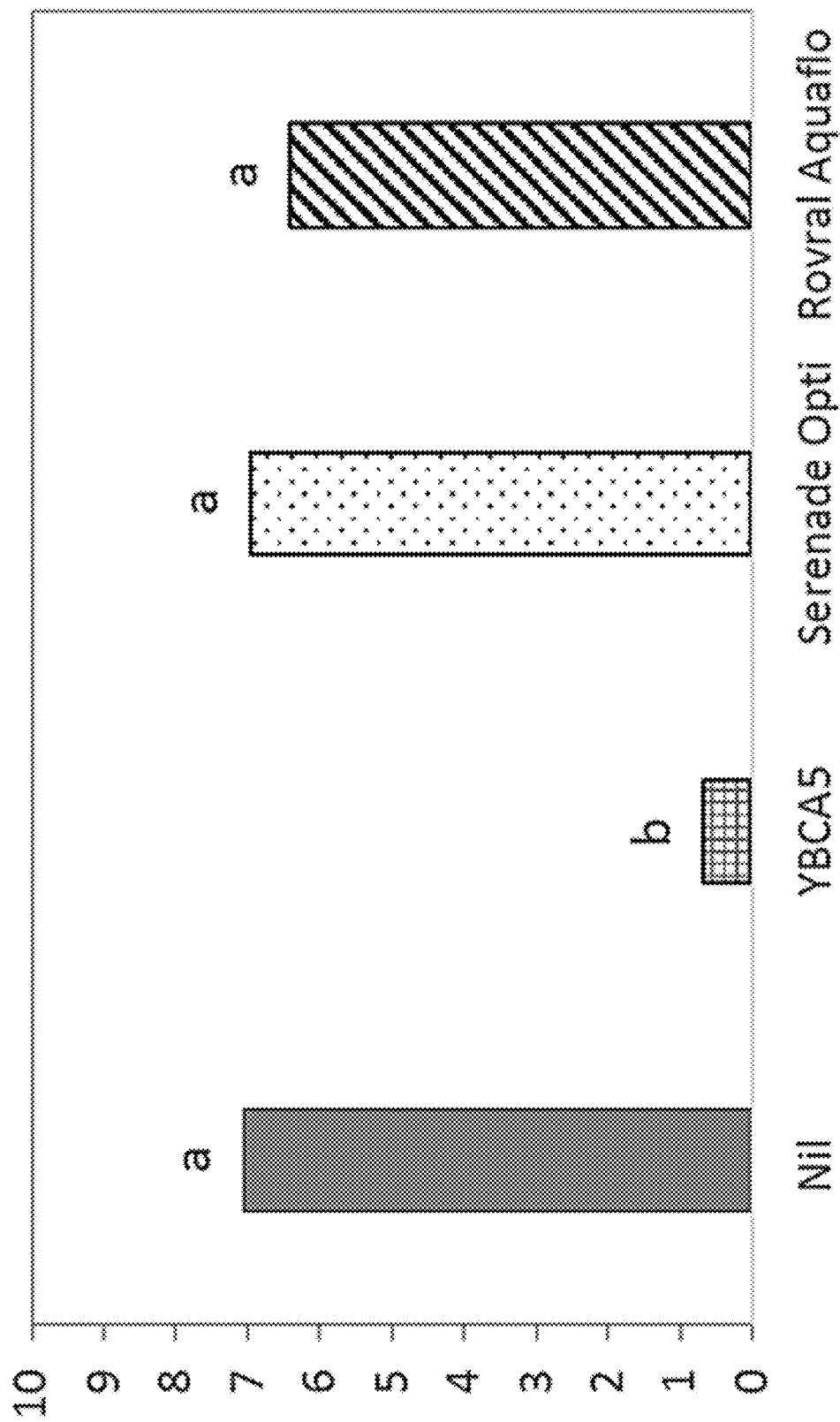
FIG. 15. The effect of YBCA5 on the severity of kiwifruit rot due to phytopathogenic fungal infection post-harvest. Lesion size (mm) of wounded 'Hongyang' kiwifruit after inoculation with *Cryptosporiopsis* spp. and 7 days incubation. LSD (5%)=1.945, P fr=<0.001.

In assay 9, YBCA5 treated fruit also had significantly smaller lesions in 'Hongyang' fruit than the Rovral Aquaflo, Serenade Opti treatments and the untreated control when the fruit were inoculated with *Cryptosporiopsis* (FIG. 15).
Discussion YBCA5 demonstrated activity against a range of postharvest kiwifruit fruit pathogens when it was allowed to colonise a wound site 24 hours before a pathogen was introduced to the same wound. Wounding works well as an experimental technique to demonstrate the activity of some biopesticides.

Overall, Rovral Aquaflo performed poorly in these experiments, and this agrichemical may be unsuitable for wound protection assays and against the pathogens used in this study.

Serenade Opti performed poorly in these assays, and this biopesticide may be unsuitable as a wounded fruit wound protectant against the pathogens used in these assays.

Example 5—Yeast Biocontrol of PSA in the Field

Summary
Grower standard treatment: Kocide Opti+1×Kasumin

| 1 | Product: | 2 | Active Ingredient (AI) |
|---|---|---|---|
| 3 | Kocide: | 4 | Copper Hydroxide |
| 5 | Kasumin: | 6 | Kasugamycin |
| 7 | ActiGard: | 8 | Acibenzolar-S-methyl |

Methodology: all plants had an application of copper at bud break, the treatment group then received the yeast treatment while the controls received no treatment and grower standard respectively.
Field Trials 2015-16
Methods Two field trial sites were established during spring 2015 with the intention of running across two consecutive seasons. The two 'Hayward' blocks (coded Block B and C) were located in separate orchards, near Maketu, Bay of Plenty. Block C was the same orchard as the 2014-15 trial, but a different area in the blocks was used. Vines in all blocks were pergola trained with a single vine per bay. The vines generally looked healthy at the commencement of the trial, but had suffered from significant Psa symptoms 2-3 years previously, according to the grower.

The spray treatments were applied to individual vines (eight replicates per treatment) laid out in a randomised block design. The treatments were:

1. Nil—no Psa control products applied during the growing season
2. Grower standard—copper-based foliar spray programme, including up to one antibiotic spray
3. YBCA5—yeast-based foliar spray programme ($2 \times 10^7$ CFU/mL)

Spray applications in the Grower standard and YBCA5 treatments were applied according to the schedule in Table 5. Common agricultural adjuvants were added to the Grower standard (0.04% Du-Wett®) and YBCA5 (0.03% Nu-Film-17@) applications.

TABLE 5

Application dates in Blocks B and C for the Grower standard and YBCA5 treatment to kiwifruit against *Pseudomonas syringae* pv. *actinidiae* (Psa) from bud burst to post flowering during the 2015-16 season.

| | Block B | | Block C | |
|---|---|---|---|---|
| Date Treatment | Grower standard | YBCA5 | Grower standard | YBCA5 |
| Oct. 6, 2015 | Kocide Opti[1] | YBCA5[2] | — | — |
| Oct. 7, 2015 | — | — | Kocide Opti | YBCA5 |
| Oct. 16, 2015 | Kasumin[3] | YBCA5 | Kasumin | YBCA5 |
| Oct. 27, 2015 | Kocide Opti | YBCA5 | Kocide Opti | YBCA5 |
| Nov. 4, 2015 | — | — | Kocide Opti | YBCA5 |

TABLE 5-continued

Application dates in Blocks B and C for the Grower standard and YBCA5 treatment to kiwifruit against Pseudomonas syringae pv. actinidiae (Psa) from bud burst to post flowering during the 2015-16 season.

| Date Treatment | Block B | | Block C | |
| --- | --- | --- | --- | --- |
| | Grower standard | YBCA5 | Grower standard | YBCA5 |
| Nov. 6, 2015 | Kocide Opti | YBCA5 | — | — |
| Nov. 19, 2015 | Nil (flowering) | YBCA5 | Nil (flowering) | YBCA5 |
| Dec. 21, 2015 | Nil (post fruit set) | YBCA5 | Nil (post fruit set) | YBCA5 |

[1]Kocide ® Opti ™ applied at 70 g/100 L with Du-Wett ® (0.04%)
[2]YBCA5 applied at 100 g/100 L with Nu-Film-17 ® (0.03%)
[3]Kasumin ® applied at 500 g/100 L (no adjuvant).

The YBCA5 yeast was produced by liquid fermentation, sourced from three separate production facilities: PFR (Ruakura), AgResearch (Lincoln) and Callaghan Innovation (Lower Hutt). A concentrated yeast pellet after centrifugation was supplied to the laboratory at Ruakura and this was mixed with an inert carrier and extruded to form granules which were air dried overnight in a laminar flow hood. The number of colony forming units/g was calculated by dissolving 0.2 g samples into 20 mL phosphate buffered saline amended with 0.05% Tween 80 (PBSTw). This was serially diluted and 10-µL droplets of each dilution were transferred to Petri dishes with malt yeast extract agar amended with chloramphenicol. Petri dishes were incubated for 24 h at 25° C. and then 4-6° C. for a further 24 h, prior to counting the number of colonies. The concentration of YBCA5 in the granules was $2.1 \times 10^{10}$ CFU/g. All granules were stored in airtight containers in a refrigerator (4-6° C.) and were weighed out at a rate of 100 g/100 L to achieve the target spray concentration of $2 \times 10^7$ CFU/mL.

Psa disease assessments were carried out in the 'Hayward' blocks just prior to flowering on 11 Nov. 2015 by visually assessing leaves for Psa spotting severity (% leaf area with necrosis). Assessments were carried out on leaves positioned between the second and third wire out from the main cordon. Assessments were commenced after taking one step (i.e. 1 m) from the edge of the plot and a set of 25 leaves were scored. This process was repeated after taking another step down the plot. This was then repeated down the other side of the vine so that four sets of 25 leaves (total=100) were scored within each plot. Similarly, 100 buds/plot were scored for the severity of bud-browning, as described above.

Data were expressed as Psa incidence (based on the proportion of leaves with Psa spotting/proportion of buds with brown sepals) and average Psa severity (mean % leaf area necrotic/mean number of brown sepals on buds). Data were log-transformed and analysed by ANOVA using Genstat (ver. 16) to determine treatment differences. Raw data are presented with statistical differences indicated based on the log-transformed data. Analysis was also carried out by combining data from both orchard sites, after checking for any significant site×treatment interaction.

Results

Analysis of the incidence and severity of leaves with leaf spotting (necrosis), and similarly for bud symptoms, indicated that there was no significant Treatment×Orchard interaction; therefore data are presented as the mean of the two orchards (Blocks B and C).

The nil control had a mean incidence of leaves with necrosis of 50% and this was significantly reduced (P<0.05) by the Kocide Opti and two YBCA5 treatments (Table 6). The efficacy of the YBCA5 was 33%. The Grower standard treatment (Kocide Opti+Kasumin) had an efficacy of 74% and resulted in a further significant reduction in the incidence of leaves with necrosis, compared with the YBCA5 and Kocide Opti treatments.

The mean severity of leaf spotting was only 0.24% in the nil control (Table 6). However, there was still a significant reduction (P<0.05) in the mean severity of leaf necrosis in each of the treatments, compared with the nil control, including the two YBCA5 treatments. The average efficacy of the YBCA5 was 58%, compared with the Grower standard and Kocide Opti treatments which had an efficacy of 91 and 73%, respectively.

The incidence of flower buds in the nil control with necrotic sepals was 61% and this was significantly (P<0.05) reduced by each of the treatments (Table 6). The two YBCA5 treatments had 39 and 37% incidence of buds with necrosis and an average efficacy of 38%. The Grower Standard treatment had significantly (P<0.05) less bud necrosis (13%) compared with each of the other treatments (efficacy 79%). The Kocide Opti treatment had an efficacy of 40%.

The mean severity of bud necrosis (number of necrotic sepals/bud) was 1.29 in the Nil control and similarly to the incidence of buds with necrosis, this was significantly (P<0.05) reduced by each of the treatments, with the Grower Standard treatment (0.21, efficacy=84%) providing the biggest reduction (Table 6). The average efficacy of the YBCA5 treatments was 46% and this was similar to the Kocide Opti treatment (efficacy 38%).

TABLE 6

Mean incidence and severity of leaf spotting and bud-browning on *Actinidia chinensis* var. *deliciosa* 'Hayward' vines in Block B and C following foliar application of YBCA5 in comparison to a Kasumin ® and Kocide ® Opti ™ based Grower standard foliar treatment and Kocide Opti only, assessed on Nov. 11, 2015.

| Treatment | % leaves with spotting (incidence) | Severity of spotting (% leaf area) | % buds with necrosis (incidence) | Severity of bud browning (No. sepals) |
|---|---|---|---|---|
| Nil control | 50 a | 0.24 a | 61 a | 1.29 a |
| Grower std | 13 c | 0.02 b | 13 c | 0.21 c |
| YBCA5 | 33 b | 0.11 b | 39 b | 0.68 b |
| Kocide Opti * | 27 b | 0.07 b | 45 b | 0.80 b |
| YBCA5 * | 34 b | 0.10 b | 37 b | 0.72 b |
| LSD | 8.0 | 0.099 | 9.9 | 0.226 |
| P value | <0.001 | <0.001 | <0.001 | <0.001 |

Grower std is one application Kasumin ® and three applications of Kocide ® Opti ™ applied in Du Wett ® (0.04% v/v)
YBCA5 is a formulated developmental biological control agent applied at 100 g/100 L in Nu-Film-17 ® (0.03% v/v)
Analysis performed by combining data from the two orchard trial sites
* Treatment where *Trichoderma* was soil applied to plots 1 day prior to these disease assessments
LSD is Least significant difference (P < 0.05)
Means followed by the same letters are not significantly different to each other (P < 0.05).

Field Trials 2016-17
Methods

During the winter months the grower applied his standard winter spray programme of Kocide Opti and in the spring the same treatments as above were applied to the same vines.

Spray applications commenced with the grower applying Kocide Opti across the trial block at early bud-burst (2 Oct. 2016) and this was then followed by the schedule outlined in Table 7, with the nil control plots receiving no spray applications. The *Trichoderma* treatments were also continued in these two field trials.

The YBCA5 yeast granules used this season were produced as a pre-commercial batch (YBCA5 e-nema-2) by the manufacturing company, e-nema GmbH, by liquid fermentation and fluidized bed drying. Granules of YBCA5 were imported to New Zealand on 23 Sep. 2016 and were stored in an air tight container at 4-6° C. until required for treatment application. These granules had a mean CFU/g of $3 \times 10^{10}$ on 26 Sep. 2016 and $2.6 \times 10^{10}$ when tested for viability on 2 Nov. 2016.

The application rate for YBCA5 this season was set at the likely commercial rate of 50 g/100 L (to achieve a minimum concentration of $1 \times 10^7$ CFU/mL) and was not adjusted for the actual viability in the granules, indicating that the actual application dose ranged from $1.25$-$1.5 \times 10^7$ CFU/mL. Disease assessments on leaves and buds were carried out as described for the previous season (above).

TABLE 7

Application dates in Blocks B and C for the Grower standard and YBCA5 treatment to kiwifruit against *Pseudomonas syringae* pv. *actinidiae* (Psa) from budburst to post flowering during the 2016-17 season.

| | Block B | | Block C | |
|---|---|---|---|---|
| Date Treatment | Grower standard | YBCA5 | Grower standard | YBCA5 |
| Oct. 11, 2016 | Kocide Opti[1] | YBCA5[2] | Kocide Opti | YBCA5 |
| Oct. 18, 2016 | Kasumin[3] | YBCA5 | Kasumin | YBCA5 |
| Oct. 27, 2016 | Kocide Opti | YBCA5 | Kocide Opti | YBCA5 |
| Nov. 8, 2016 | Kocide Opti | YBCA5 | Kocide Opti | YBCA5 |
| Nov. 14, 2016 | Nil (flowering) | YBCA5 | Nil (flowering) | YBCA5 |
| Dec. 5, 2016 | Nil (post fruit set) | YBCA5 | Nil (post fruit set) | YBCA5 |

[1]Kocide ® Opti ™ applied at 70 g/100 L with Du-Wett ® (0.04%)
[2]YBCA5 applied at 50 g/100 L with Bond ® Xtra (0.06%)
[3]Kasumin ® applied at 500 g/100 L (no adjuvant).

Psa disease assessments on flower buds were carried out in the 'Hayward' blocks just prior to flowering on 11 Nov. 2016 by visually assessing 100 buds/plot for the severity of bud-browning, as described above. Leaves were assessed for Psa spotting severity (% leaf area with necrosis) in these trial plots on 18 Nov. 2016. As described above, assessments were carried out on leaves positioned between the second and third wire out from the main cordon. Assessments were commenced after taking one step (i.e. 1 m) from the edge of the plot and a set of 25 leaves were scored. This process was repeated after taking another step down the plot. This was then repeated down the other side of the vine so that four sets of 25 leaves (total=100) were scored within each plot.

Results

In the second year of this field trial the incidence of leaf spotting was 31% in the nil control and this was significantly reduced in the two YBCA5 treatments (Table 8). The efficacy of the YBCA only treatment was 42%. The Grower standard treatment, which included the bactericide Kasumin, provided a significant further reduction in the incidence of leaf spotting, compared with the YBCA5 treatments (efficacy=74%).

The mean severity of leaf spotting was 0.19% in the nil control and this was significantly reduced in the YBCA5 treatments, compared with the nil control (Table 8). The efficacy of the YBCA only treatment was 53%. There was a further reduction in the Grower standard treatment, but in this case the Grower standard and YBCA5 treatments were not significantly different to each other.

In the nil control, the incidence of buds with necrosis was 18% and the severity of the necrosis was 0.27. The two YBCA5 treatments significantly reduced bud incidence and severity compared with the nil control (efficacy of YBCA5 only=56 and 59%, respectively). Although the Grower standard had less disease than the YBCA5 treatments these were not significantly different.

TABLE 8

Mean incidence and severity of leaf spotting and bud-browning on *Actinidia chinensis* var. *deliciosa* 'Hayward' vines in Block B and C following foliar spray application of YBCA5 in comparison to a Kasumin ® and Kocide ® Opti ™ based Grower standard foliar treatment and a *Trichoderma* treatment, assessed on Nov. 11, 2016 (buds) and Nov. 18, 2016 (leaves).

| Treatment | % leaves with spotting (incidence) | Severity of spotting (% leaf area) | % buds with necrosis (incidence) | Severity of bud browning (No. sepals) |
|---|---|---|---|---|
| Nil control | 31 a | 0.19 a | 18 a | 0.27 a |
| Grower std | 8 c | 0.02 c | 4 b | 0.05 b |
| YBCA5 | 18 b | 0.09 bc | 8 b | 0.11 b |
| *Trichoderma* | 29 a | 0.17 ab | 14 a | 0.20 a |
| YBCA5 * | 18 b | 0.08 bc | 8 b | 0.09 b |
| LSD | 8.4 | 0.092 | 5.1 | 0.085 |
| P value | <0.001 ** | 0.005 | <0.001 | <0.001 |

Grower std is one application Kasumin ® and three applications of Kocide ® Opti ™ applied in Du Wett ® (0.04% v/v)
YBCA5 is a formulated developmental biological control agent applied at 100 g/100 L in Bond ® Xtra (0.03% v/v)
Analysis performed by combining data from the two orchard trial sites
* YBCA5 treatment where *Trichoderma* had been applied to the soil of these plots on three occasions during the previous 12 months
** There was a significant site × treatment interaction (P = 0.016) for this variable, such that there was no significant treatment effects in Block C and in Block B there was a highly significant treatment effect (P < 0.001) with the treatment difference being the same as indicated in this combined analysis
LSD is Least significant difference (P < 0.05)
Means followed by the same letters are not significantly different to each other (P < 0.05).

Conclusion:

YBCA5 treatment showed significant reductions in incidence and severity of leaf spotting and bud browning in 'Hayward' vines.

It will be appreciated that the above description is provided by way of example only and that variations in both the materials and techniques used which are known to those persons skilled in the art are contemplated.

Although the invention has been described by way of example and with reference to particular embodiments, it is to be understood that modifications and/or improvements may be made without departing from the scope of the invention.

In addition, where features or aspects of the invention are described in terms of Markush groups, those skilled in the art will recognise that the invention is also thereby described in terms of any individual member or subgroup of members of the Markush group.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The following numbered paragraphs define particular aspects of the present invention:

1. Isolated *Aureobasidium pullulans* yeast strain YBCA5 (CBS Accession #141880).

2. A composition comprising YBCA5 and an agriculturally acceptable carrier.

3. A composition consisting essentially of YBCA5 and an agriculturally acceptable carrier.

4. The composition of paragraph 2 or paragraph 3, wherein YBCA5 is present in the form of reproductively viable cells.

5. The composition of any one of paragraphs 2 to 4, wherein the concentration of YBCA5 viable cells ranges from about $1 \times 10^3$ to about $1 \times 10^{14}$, preferably about $1 \times 10^5$ to about $1 \times 10^{11}$, preferably about $1 \times 10^6$ to about $1 \times 10^9$, preferably about $1 \times 10^7$ to about $1 \times 10^8$, preferably about $2 \times 10^7$ to about $2 \times 10^8$ CFU, preferably about $2 \times 10^9$ to about $2 \times 10^{10}$ CFU per gram for solid compositions, and about $1 \times 10^7$ to about $1 \times 10^8$ CFU per millilitre for liquid compositions.

6. The composition of any one of paragraphs 2 to 5, wherein the agriculturally acceptable carrier is water.

7. The composition of any one of paragraphs 2 to 6, further comprising at least one agriculturally acceptable adjuvant.

8. The composition of any one of paragraphs 2 to 7, wherein the agriculturally acceptable adjuvant is selected from the group consisting of an additional active agent and a formulation agent.

9. The composition of any one of paragraphs 2 to 7, wherein the agriculturally acceptable adjuvant is one or more additional active agents.

10. The composition of any one of paragraphs 2 to 7, wherein the agriculturally acceptable adjuvant is one or more formulation agents.

11. The composition of any one of paragraphs 2 to 7, wherein the agriculturally acceptable adjuvant comprises combination of one or more additional active agents and one or more formulation agents.

12. The composition of any one of paragraphs 2 to 11, wherein the composition is formulated as a solid or a liquid formulation.

13. The composition of any one of paragraphs 2 to 12 wherein the composition is a pre-prepared composition or wherein the composition is in a concentrated form.

14. A method of controlling *Pseudomonas* spp. bacteria on a plant or part thereof, the method comprising contacting the plant or part thereof with YBCA5, or a composition of any one of paragraphs 2 to 13.

15. The method of paragraph 14, wherein the at least one strain of *Pseudomonas* spp. bacteria is a strain of bacteria selected from the group consisting of *P. syringae, P. amygdalia, P. avellanae, P. caricapapayae, P. cichorii, P. coronafaciens, P. ficuserectae, P. helianthi, P. lemiae, P. savastanoi,* and *P. viridiflava*, or a pathovar thereof, or combinations thereof, preferably the at least one strain is *P. syringae* or a pathovar thereof, more preferably the at least one strain is *P. syringae* pv. *actinidiae* (Psa).

16. The method of paragraph 14 or 15, wherein the plant or part thereof is contacted for a time sufficient to control *Pseudomonas* spp. bacteria, preferably Psa bacteria.

17. The method of paragraph 16, wherein contacting is for a time sufficient to reduce the survival, growth and/or proliferation of *Pseudomonas* spp. bacteria, preferably Psa bacteria.

18. The method of any one of paragraphs 14 to 17, wherein contacting comprises applying YBCA5, or the composition of any one of paragraphs 2 to 13 to the plant leaves, stems, flowers, fruits, trunks and/or roots or part thereof.

19. The method of paragraph 18, wherein applying comprises dusting, spraying, dripping, sprinkling, or mixing, or combinations thereof.

20. The method of paragraph 18, wherein applying to the roots is by ground spraying, mechanical incorporation or by mixing with enriching agents or fertilizers prior to the application of said enriching agents or fertilizers.

21. The method of any one of paragraphs 14 to 20, wherein the plant or part thereof is selected from the group of monocotyledonous plants, dicotyledonous plants, annual, biannual and perennial plants, vegetable plants or harvested vegetables, fruit plants or trees or harvested fruits, flower bearing plants or trees or harvested flowers, cereal plants, oleaginous plants, proteinous plants, ligneous plants, and ornamental plants.

22. The method of any one of paragraphs 14 to 21, wherein the plant or part thereof is an agriculturally important plant, cultivar thereof, or product thereof selected from the group consisting of agriculturally important vines and agriculturally important fruit trees, and cultivars and products thereof, preferably wherein the agriculturally important fruit trees or cultivars thereof are selected from olive trees, apple trees, pear trees, citrus fruit trees, banana trees, pineapple trees, peach trees, apricot trees, cherry trees, walnut trees and hazelnut trees and the products thereof are olives, apples, pears, citrus fruits, bananas, pineapples, peaches, apricots, cherries, walnuts and hazelnuts respectively, preferably wherein the agriculturally important vines or cultivars thereof are selected from potato vines, beetroot vines, bean vines, pea vines, tomato vines, cucumber vines, melon vines, berry vines, grape vines and kiwifruit vines and the products thereof are potatoes, beetroots, beans, peas, tomatoes, cucumbers, melons, berries, grapes and kiwifruits respectively, preferably wherein the agriculturally important vine is a kiwifruit vine or cultivar thereof, and the product is kiwifruit.

23. The method of paragraph 22, wherein the kiwifruit vine is selected from the group consisting of species of fuzzy kiwifruit (*Actinidia deliciosa*), golden kiwifruit (*A. chinensis* var. *chinensis*), Chinese egg gooseberry (*A. coriacea*), baby kiwifruit (*A. arguta*), Arctic kiwifruit (*A. kolomikta*), red kiwifruit (*A. melanandra, A. chinensis* var. *chinensis*), silver vine (*A. polygama*), and purple kiwifruit (*A. purpurea*) or a cultivar thereof, preferably wherein the kiwifruit are selected from the group consisting of *A. chinensis* var. *deliciosa* and *A. chinensis* var. *chinensis* species or a cultivar thereof, preferably wherein the kiwifruit is a species of *A. chinensis*, preferably wherein the kiwifruit is *A. chinensis* var. *chinensis* Planch, preferably wherein the cultivar is a 'Hayward' or 'Hort16A' variety cultivar.

24. The method of paragraph 23, wherein the cultivar is *A. chinensis* var. *chinensis* Planch, 'Hort16A'.

25. The method of paragraph 23, wherein the cultivar is *A. chinensis* var. *deliciosa* 'Hayward'.

26. The method of any one of paragraphs 12 to 25, the plant or part thereof is an agriculturally important crop plant, cultivar or product thereof selected from corn plants, tobacco plants, wheat plants, sugar cane plants, rapeseed plants, barley plants, rice plants, sorghum plants, millet plants, soya bean plants, lettuce plants, and cabbage plants.

27. A method for controlling *P. syringae* pv. *actinidiae* (Psa) on a kiwifruit plant or part thereof, the method comprising contacting the kiwifruit plant or part thereof with YBCA5, or a composition of any one of paragraphs 2 to 13 to a species of *A. chinensis* var. *deliciosa* or *A. chinensis* var. *chinensis*, or a cultivar thereof, preferably a species of *A. chinensis* var. *chinensis*, or cultivar thereof, preferably wherein the kiwifruit plant is 'Hort16A' or 'Hayward'.

28. A method for increasing the yield of a kiwifruit plant infected, or susceptible to infection by *Pseudomonas* spp., preferably infected, preferably susceptible to infection with Psa, the method comprising applying YBCA5, or a composition of any one of paragraphs 2 to 13 to the kiwifruit plant or part thereof.

29. A method of controlling at least one phytopathogenic fungus on a plant or part thereof, the method comprising contacting the plant or part thereof with YBCA5, or a composition of any one of paragraphs 2 to 13.

30. A method for increasing the yield of a fruit or vegetable plant infected, or susceptible to infection by a phytopathogenic fungus, the method comprising applying YBCA5, or a composition of any one of paragraphs 2 to 13 to the fruit or vegetable plant or part thereof, and growing the plant or part thereof.

31. Use of YBCA5, or a composition of any one of paragraphs 2 to 13 for controlling *Pseudomonas* spp. bacteria on a plant or part thereof.

32. Use of YBCA5, or a composition of any one of paragraphs 2 to 13 for controlling Psa on a kiwifruit plant or part thereof.

33. Use of YBCA5, or a composition of any one of paragraphs 2 to 13 for controlling a phytopathogenic fungus on a fruit or vegetable plant or part thereof.

34. Use of YBCA5, or a composition of any one of paragraphs 2 to 13 for increasing the yield of a kiwifruit plant or part thereof infected, or susceptible to infection with Psa.

35. Use of YBCA5, or a composition of any one of paragraphs 2 to 13 for increasing the yield of a fruit or vegetable plant or part thereof infected with, or susceptible to infection by a phytopathogenic fungus.

36. YBCA5, or a composition of any one of paragraphs 2 to 13, for use in, or when used, for controlling *Pseudomonas* spp. bacteria on a plant or part thereof.

37. YBCA5, or a composition of any one of paragraphs 2 to 13, for use in, or when used, for controlling Psa on a kiwifruit plant or part thereof.

38. YBCA5, or a composition of any one of paragraphs 2 to 13, for use in, or when used, for controlling a phytopathogenic on a kiwifruit plant or part thereof.

39. YBCA5, or a composition of any one of paragraphs 2 to 13, for use in, or when used, for increasing the yield of a kiwifruit plant or part thereof infected, or susceptible to infection with *Pseudomonas* spp.

40. YBCA5, or a composition of any one of paragraphs 2 to 13, for use in, or when used, for increasing the yield of a kiwifruit plant or part thereof infected, or susceptible to infection with Psa.

41. YBCA5, or a composition of any one of paragraphs 2 to 13, for use in, or when used, for increasing the yield of a fruit or vegetable plant or part thereof infected with, or susceptible to infection by a phytopathogenic fungus.

42. At least one plant or part thereof treated with YBCA5, or a composition of any one of paragraphs 2 to 13 according to a method of any one of paragraphs 14 to 30 or according the uses of any one of paragraphs 31 to 35.

INDUSTRIAL APPLICATION

The isolated *Aureobasidium pullulans* yeast strain YBCA5 and compositions comprising or consisting essentially of YBCA5 of the present invention find a use in controlling phytopathogenic bacteria and fungi.

What we claim is:

1. A method of controlling phytopathogenic bacteria and/or phytopathogenic fungi on a plant or plant part, the method comprising contacting the plant or part thereof with *Aureobasidium pullulans* yeast strain YBCA5, which is on deposit under CBS Accession #141880, or a composition comprising said yeast.

2. The method of claim 1, wherein the composition further comprises an agriculturally acceptable carrier.

3. The method of claim 1, wherein the YBCA5 is present in the composition in the form of reproductively viable cells.

4. The method of claim 1, wherein the YBCA5 is present in the composition at a concentration ranging from about $1\times10^5$ to about $1\times10^{11}$ CFU per gram for solid compositions, and about $1\times10^7$ to about $1\times10^8$ CFU per millilitre for liquid compositions.

5. The method of claim 1, wherein the YBCA5 is present in the composition at a concentration ranging from about $2\times10^7$ to about $2\times10^8$ CFU per gram for solid compositions, and about $1\times10^7$ to about $1\times10^8$ CFU per millilitre for liquid compositions.

6. The method of claim 1, wherein the YBCA5 is present in the composition at a concentration ranging from about $2\times10^9$ to about $2\times10^{10}$ CFU per gram for solid compositions, and about $1\times10^7$ to about $1\times10^8$ CFU per millilitre for liquid compositions.

7. The method of claim 1, wherein the composition further comprises at least one agriculturally acceptable adjuvant.

8. The method of claim 1, wherein the composition further comprises an effective amount of a stabilizer.

9. The method of claim 1, wherein the phytopathogenic bacteria is a *Pseudomonas* spp. bacteria.

10. The method of claim 9, wherein the *Pseudomonas* spp. bacteria is selected from *P. syringae*, *P. amygdalia*, *P. avellanae*, *P. caricapapayae*, *P. cichorii*, *P. coronafaciens*, *P. ficuserectae*, *P. helianthi*, *P. lemiae*, *P. savastanoi*, *P. viridiflava*, a pathovar thereof, and a combination thereof.

11. The method of claim 10, wherein the *Pseudomonas* spp. bacteria is *P. syringae* or a pathovar thereof.

12. The method of claim 10, wherein the *Pseudomonas* spp. bacteria is *P. syringae* pv. *actinidiae* (Psa).

13. The method of claim 1, wherein the phytopathogenic fungi is selected from *Botrytis* spp., *Alternaria* spp., *Colletotrichum* spp., *Penicillium* spp., *Phomopsis* spp., *Cryptosporiopsis* spp., *Monilinia* spp., *Sclerotinia* spp., and a combination thereof.

14. The method of claim 13, wherein the phytopathogenic fungus is a *Monilinia* spp. fungus.

15. The method of claim 13, wherein the phytopathogenic is *Monilinia fruticola*.

16. The method of claim 1, wherein the plant or part thereof is an agriculturally important plant, cultivar thereof, or product thereof, selected from olive trees, apple trees, pear trees, citrus fruit trees, banana trees, pineapple trees, peach trees, apricot trees, cherry trees, walnut trees and hazelnut trees, wherein the products thereof are olives, apples, pears, citrus fruits, bananas, pineapples, peaches, apricots, cherries, walnuts, and hazelnuts, respectively.

17. The method of claim 1, wherein the plant or part thereof is an agriculturally important plant, cultivar thereof, or product thereof, selected from potato vines, beetroot vines, bean vines, pea vines, tomato vines, cucumber vines, melon vines, berry vines, grape vines and kiwifruit vines, and the products thereof are potatoes, beetroots, beans, peas, tomatoes, cucumbers, melons, berries, grapes and kiwifruits, respectively.

18. The method of claim 17, wherein the agriculturally important plant, cultivar thereof, or product thereof, is a kiwifruit vine or cultivar thereof, and the product is kiwifruit.

19. The method of claim 18, wherein the kiwifruit vine is selected from the group consisting of species of green-fleshed kiwifruit (*Actinidia chinensis* var. *deliciosa*), golden kiwifruit (*A. chinensis* var. *chinensis*), Chinese egg gooseberry (*A. coriacea*), baby kiwifruit (*A. arguta*), Arctic kiwifruit (*A. kolomikta*), red kiwifruit (*A. melanandra*, *A. chinensis* var. *chinensis*), silver vine (*A. polygama*), purple kiwifruit (*A. purpurea*) and a cultivar thereof.

20. The method of claim 18, wherein the kiwifruit vine is selected from the group consisting of *A. chinensis* var. *deliciosa A. chinensis* var. *chinensis* species and a cultivar thereof.

21. The method of claim 18, wherein the kiwifruit is a 'Hayward', 'Hort16A', or 'Hongyang' variety cultivar.

* * * * *